US012049625B2

(12) United States Patent
Krichevsky et al.

(10) Patent No.: US 12,049,625 B2
(45) Date of Patent: Jul. 30, 2024

(54) GENOME EDITING FOR TREATING GLIOBLASTOMA

(71) Applicant: The Brigham and Women's Hospital, Inc., Boston, MA (US)

(72) Inventors: Anna M. Krichevsky, Brookline, MA (US); Rachid El-Fatimy, Brighton, MA (US); Erik J. Uhlmann, Newton Center, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 1611 days.

(21) Appl. No.: 16/069,727

(22) PCT Filed: Jan. 13, 2017

(86) PCT No.: PCT/US2017/013386

§ 371 (c)(1),
(2) Date: Jul. 12, 2018

(87) PCT Pub. No.: WO2017/123910

PCT Pub. Date: Jul. 20, 2017

(65) Prior Publication Data

US 2019/0010496 A1 Jan. 10, 2019

Related U.S. Application Data

(60) Provisional application No. 62/278,732, filed on Jan. 14, 2016.

(51) Int. Cl.

| | |
|---|---|
| ***C12N 15/113*** | (2010.01) |
| ***A61K 9/00*** | (2006.01) |
| ***A61K 31/7088*** | (2006.01) |
| ***A61K 38/46*** | (2006.01) |
| ***A61K 48/00*** | (2006.01) |
| ***A61P 35/00*** | (2006.01) |
| ***C12N 9/22*** | (2006.01) |
| *C12Q 1/6886* | (2018.01) |

(52) U.S. Cl.

CPC .......... *C12N 15/113* (2013.01); *A61K 9/0019* (2013.01); *A61K 9/0085* (2013.01); *A61K 31/7088* (2013.01); *A61K 38/465* (2013.01); *A61K 48/0066* (2013.01); *A61P 35/00* (2018.01); *C12N 9/22* (2013.01); *C12N 2310/113* (2013.01); *C12N 2310/20* (2017.05); *C12N 2800/80* (2013.01); *C12Q 1/6886* (2013.01)

(58) Field of Classification Search

None

See application file for complete search history.

(56) References Cited

U.S. PATENT DOCUMENTS

| | | | |
|---|---|---|---|
| 9,150,928 | B2 | 10/2015 | Krichevsky et al. |
| 10,100,367 | B2 | 10/2018 | Krichevsky et al. |
| 2006/0105360 | A1 | 5/2006 | Croce et al. |
| 2010/0167948 | A1 | 7/2010 | Krichevsky et al. |
| 2010/0178653 | A1 | 7/2010 | Aharonov et al. |
| 2012/0277163 | A1 | 11/2012 | Gaur et al. |
| 2015/0118216 | A1 | 4/2015 | Liu et al. |
| 2015/0353927 | A1 | 12/2015 | Leake et al. |
| 2016/0115549 | A1 | 4/2016 | Krichevsky et al. |

FOREIGN PATENT DOCUMENTS

| | | |
|---|---|---|
| WO | WO 2008/153692 | 12/2008 |
| WO | WO 2012/068288 | 5/2012 |
| WO | 2014/197748 | 12/2014 |
| WO | 2015/162274 | 10/2015 |

OTHER PUBLICATIONS

El Fatimy, R. et al., Mol Ther 2017, vol. 25: pp. 368-378.*
Chen, M. et al., Cancer Lett., 2019, 8 pages.*
Ahmad et al., "Up-regulation of microRNA-10b is associated with the development of breast cancer brain metastasis," Am J Transl Res, 2014, 6: 384-90.
Baffa et al., "MicroRNA expression profiling of human metastatic cancers identifies cancer gene targets," J. Pathol., 219(2):214-221 (2009).
Baraniskin et al., "Identification of microRNAs in the cerebrospinal fluid as biomarker for the diagnosis of glioma," Neuro. Oncol., 14(1):29-33 (2012; Advance Access publication Sep. 21, 2011).
Baraniskin et al., "Identification of microRNAs in the cerebrospinal fluid as markers for primary diffuse large B-cell lymphoma of the central nervous system," Blood, 117:3140-3146 (2011).
Bayin et al., "Selective lentiviral gene delivery to CD133-expressing human glioblastoma stem cells," PLoS One, 2014, 9(12):e116114.
Biagioni et al., "The locus of microRNA-10b: a critical target for breast cancer insurgence and dissemination," Cell Cycle, 2013, 12(15):2371-5.
Birks et al., "Survey of MicroRNA expression in pediatric brain tumors," Pediatr. Blood Cancer, 56(2):211-216 (2011).
Chan et al., "MicroRNA-21 is an antiapoptotic factor in human glioblastoma cells," Cancer Res., 65(14):6029-6033 (2005).
Chen et al., "Characterization of microRNAs in serum: a novel class of biomarkers for diagnosis of cancer and other diseases," Cell Res., 18(10):997-1006 (2008).
Cogswell et al., "Identification of miRNA changes in Alzheimer's Disease Brain and CSF Yields Putative Biomarkers and Insights into Disease Pathways," Journal of Alzheimer's Disease, 14:27-41 (2008).
Cong et al., "Multiplex genome engineering using CRISPR/Cas systems," Science, 2013, 339(6121):819-23.

(Continued)

*Primary Examiner* — Michael D Burkhart

(74) *Attorney, Agent, or Firm* — Fish & Richardson P.C.

(57) ABSTRACT

A method of treating a subject who has a glioma, e.g., astrocytoma, oligodendroglioma, or glioblastoma multiforme tumor, the method comprising administering to the subject a therapeutically effective amount of a Clustered Regularly Interspaced Short Palindromic Repeats (CRISPR) microRNA-10b (miR-10b) editing complex comprising a CRISPR Associated Protein 9 (Cas9) and at least one guide RNA targeting a sequence encoding miR-10b.

15 Claims, 21 Drawing Sheets

Specification includes a Sequence Listing.

(56) References Cited

OTHER PUBLICATIONS

Davis and Maizels, "Homology-directed repair of DNA nicks via pathways distinct from canonical double-strand break repair," PNAS, 2014.
DePolo et al., "VSV-G pseudotyped lentiviral vector particles produced in human cells are inactivated by human serum," Mol Ther, 2000, 2(3):218-22.
Doudna and Charpentier, "Genome editing. The new frontier of genome engineering with CRISPR-Cas9," Science, 2014, 346(6213):125809.
Filippini et al., "Prognostic factors for survival in 676 consecutive patients with newly diagnosed primary glioblastoma," Neuro Oncol., 10(1):79-87 (2008).
Floyd and Purow, "Micro-masters of glioblastoma biology and therapy: increasingly recognized roles for microRNAs," Neuro Oncol, 2014, 16(5):622-7.
Gabriely et al., "Human glioma growth is controlled by microRNA-10b," Cancer Res., 2011, 71(10):3563-3572.
Gabriely et al., "MicroRNA 21 promotes glioma invasion by targeting matrix metalloproteinase regulators," Mol. Cell Biol., 28(17):5369-5380 (2008).
Gaur et al., "Downregulation of Pdcd4 by mir-21 facilitates glioblastoma proliferation in vivo," Neuro Oncol.13(6):580-590 (2011).
Gilad et al., "Serum microRNAs are promising novel biomarkers," PLoS One, 3(9):e3148 (2008).
Goldberg et al., Conditional tolerance of temperate phages via transcription-dependent CRISPR-Cas targeting. Nature, 2014, 514(7524):633-7.
Guessous et al., "Oncogenic effects of miR-10b in glioblastoma stem cells," J Neurooncol, 2013, 112(2):153-63.
Heneghan et al., "Systemic miRNA-195 differentiates breast cancer from other malignancies and is a potential biomarker for detecting noninvasive and early stage disease," Oncologist. 15(7):673-682 (2010).
Hudson et al., "International network of cancer genome projects," Nature, 464:993-998 (2010).
Huszthy et al., "Remission of invasive, cancer stem-like glioblastoma xenografts using lentiviral vector-mediated suicide gene therapy," PLOS One, 2009, 4(7):e6314.
Incontro et al., "Efficient, complete deletion of synaptic proteins using CRISPR," Neuron, 2014, 83(5):1051-7.
International Preliminary Report on Patentability in International Application No. PCT/US2017/013386, mailed on Jul. 26, 2018, 10 pages.
International Search Report issued in PCT/US2011/061047 on Jul. 9, 2012, 12 pages.
Jackman et al., "Response and resistance in a non-small-cell lung cancer patient with an epidermal growth factor receptor mutation and leptomeningeal metastases treated with high-dose gefitinib," J. Clin. Oncol., 24(27):4517-4520 (2006).
Keller et al., "miRNAs in lung cancer—studying complex fingerprints in patient's blood cells by micro array experiments," BMC Cancer, 9:353 (2009).
Kiani et al., "Cas9 gRNA engineering for genome editing, activation and repression," Nat Methods, 2015, 12(11): 1051-4.
Korpal et al., "The emerging role ofmiR-200 family of microRNAs in epithelial-mesenchymal transition and cancer metastasis," RNA Biol., 5(3):115-119 (2008).
Korpal et al., "The miR-200 Family Inhibits Epithelial-Mesenchymal Transition and Cancer Cell Migration by Direct Targeting of E-cadherin Transcriptional Repressors ZEB1 and ZEB2," The Journal of Biological Chemistry, 2008, 283(22):14910-14914.
Krichevsky et al., "miR-21: a small multi-faceted RNA," J. Cell Mol. Med., 2009, 13(1):39-53.
Lawrie et al., "Detection of elevated levels of tumour-associated microRNAs in serum of patients with diffuse large B-cell lymphoma," Br. J. Haematol., 141(5):672-675 (2008).
Li et al., "microRNA expression profiles in human colorectal cancers with brain metastases," Oncol Lett, 2012, 3: 346-50.
Liang et al., "Characterization of micro RNA expression profiles in normal human tissues," BMC Genomics, 8:166 (2007).
Lu et al., "MicroRNA expression profiles classify human cancers," Nature, 435(7043):834-838 (2005).
Lu et al., "The association between abnormal microRNA-10b expression and cancer risk: a meta-analysis," Sci Rep, 2014, 4: 7498.
Ma et al., "Tumour invasion and metastasis initiated by microRNA-10b in breast cancer," Nature, 449(7163):682-688 (2007).
Ma et al., "Therapeutic silencing of miR-10b inhibits metastasis in a mouse mammary tumor model," Nat Biotechnol, 2010, 28: 341-7.
Mitchell et al., "Circulating microRNAs as stable blood-based markers for cancer detection," Proc. Natl. Acad. Sci. USA, 105(30):10513-10518 (2008).
Murakami et al., "Comprehensive analysis of micro RNA expression patterns in hepatocellular carcinoma and non-tumorous tissues," Oncogene, 25(17):2537-2545 (2006).
Nass et al., "MiR-92b and miR-9/9* are specifically expressed in brain primary tumors and can be used to differentiate primary from metastatic brain tumors," Brain Pathol., 19(3):375-383 (2009).
Network CGAR, "Comprehensive genomic characterization defines human glioblastoma genes and core pathways," Nature, 455(7216):1061-1068 (2008).
Parrella et al., "Evaluation of microRNA-10b prognostic significance in a prospective cohort of breast cancer patients," Mol Cancer, 2014, 13: 142.
Ran et al., "In vivo genome editing using Staphylococcus aureus Cas9," Nature, 2015, 520(7546):186-91.
Ran et al., "Double nicking by RNA-guided CRISPR Cas9 for enhanced genome editing specificity," Cell, 2013, 154: 1380-9.
Ran et al., "Genome engineering using the CRISPR-Cas9 system," Nat Protoc, 2013, 8: 2281-308.
Sander and Joung, "CRISPR Cas systems for editing regulating and targeting," Nat Biotechnol, 2014, 32(4): 347-55.
Sanjana et al., "Improved vectors and genome-wide libraries for CRISPR screening," Nat Methods, 2014, 11: 783-4.
Sasayama et al., "MicroRNA-10b is overexpressed in malignant glioma and associated with tumor invasive factors, uPAR and RhoC," Int. J. Cancer., 125(6):1407-1413 (2009).
Schramedei et al., "MicroRNA-21 targets tumor 25 suppressor genes ANP32A and SMARCA4," Oncogene, 30(26):2975-2985 (2011).
Shalem et al., "Genome-scale CRISPR-Cas9 knockout screening in human cells," Science, 2014, 343: 84-7.
Skog et al., "Glioblastoma microvesicles transport RNA and proteins that promote tumour growth and provide diagnostic biomarkers," Nat. Cell. Biol., 10(12):1470-1476 (2008).
Straub et al., "CRISPR/Cas9-mediated gene knock-down in post-mitotic neurons," PLoS One, 2014, 9(8):e105584.
Sun et al., "MicroRNA-10b induces glioma cell invasion by modulating MMP-14 and uPAR expression via HOXD10," Brain Res, 2011, 1389:9-18.
Swiech et al., "In vivo interrogation of gene function in the mammalian brain using CRISPR-Cas9," Nat Biotechnol, 2015, 33(1):102-6.
Tehler et al., The miR-10 microRNA precursor family. RNA Biol, 2011, 8(5):728-34.
Teplyuk et al., "MicroRNA-10b inhibition reduces E2F1-mediated transcription and miR-15/16 activity in glioblastoma," Oncotarget, 2015, 6(6):3770-83.
Teplyuk et al., "MicroRNAs in cerebrospinal fluid identify glioblastoma and metastatic brain cancers and reflect disease activity," Neuro Oncol, 2012, 14: 689-700.
Teplyuk et al., "Therapeutic potential of targeting microRNA-10b in established intracranial glioblastoma: first steps toward the clinic," EMBO Mol Med, 2016,10.15252/emmm.201505495.
Tian et al., "MicroRNA-10b promotes migration and invasion through KLF4 in human esophageal cancer cell lines," J Biol Chem, 2010, 12;285(11):7986-94.
Volinia et al., "A microRNA expression signature of human solid tumors defines cancer gene targets," Proc. Natl. Acad. Sci. USA, 103(7):2257-2261 (2006).

(56) References Cited

OTHER PUBLICATIONS

Wakimoto et al., "Maintenance of primary tumor phenotype and genotype in glioblastoma stem cells," Neuro Oncol, 2012, 14(2): 132-44.
Weber et al., "The MicroRNA Spectrum in 12 Body Fluids," Clinical Chemistry, 56:1733-1741 (2010).
Wong et al., "The Cancer Genome Atlas Analysis Predicts MicroRNA for Targeting Cancer Growth and Vascularization in Glioblastoma," Mol Ther, 2015, 23(7):1234-47.
Zhang et al., "Expression profile of microRNAs in serum: a fingerprint for esophageal squamous cell carcinoma," Clin. Chem., 56(12):1871-1879 (2010).
Zhang et al., "Profiling alternatively spliced mRNA isoforms for prostate cancer classification," BMC Bioinformatics, 7:202 (2006).
Zhang et al., "Off-target Effects in CRISPR/Cas9-mediated Genome Engineering," Mol Ther Nucleic Acids, 2015, 4:e264.
International Search Report and Written Opinion mailed in international application No. PCT/US2017/013386, 16 pgs.
Kleinstiver et al., "Engineered CRISPR-Cas9 nucleases with altered PAM specificities," Nature 523(7561): 481-485 (Jul. 23, 2015).

* cited by examiner

GENOME EDITING FOR TREATING GLIOBLASTOMA

CLAIM OF PRIORITY

This application is a § 371 National Stage Application of PCT/US2017/013386, filed Jan. 13, 2017, which claims the benefit of U.S. Provisional Application Ser. No. 62/278,732, filed on Jan. 14, 2016. The entire contents of the foregoing are incorporated herein by reference.

FEDERALLY SPONSORED RESEARCH OR DEVELOPMENT

This invention was made with Government support under Grant No. RO1CA138734 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Jan. 5, 2017, is named 29618_5T25.txt and is 140,526 bytes in size.

TECHNICAL FIELD

The present invention relates, at least in part, to methods of treating glioma, e.g., astrocytoma, oligodendroglioma, or glioblastoma, using CRISPR/Cas mediated genome editing of one or both of microRNA 10b (miR-10b) and/or 10a (miR-10a).

BACKGROUND

A glioma is a primary central nervous system (CNS) tumor that arises from glial cells. Gliomas can include astrocytoma, oligodendroglioma, or glioblastoma multiforme (GBM) tumors. GBM, the most common malignant brain tumor, is a heterogeneous mixture of poorly- or un-differentiated neoplastic astrocytes typically present in the subcortical white matter of the cerebral hemispheres. GBM remains one of the most lethal human diseases as even patients treated with optimal therapy only have a median survival of about one year, a measure which has only marginally improved over the past 25 years. There is an urgent need for new molecular targets, concepts, and approaches to treating this disease.

SUMMARY

Gliomas such as glioblastoma (GBM) brain tumors remain among the most lethal and incurable human diseases. Oncogenic microRNA-10b (miR-10b) is strongly and universally up-regulated in GBM and other gliomas (see Gabriely et al., Cancer Res 71: 3563-72, 2011, Teplyuk et al., Oncotarget. 2015 Feb. 28; 6(6):3770-83), and its inhibition by antisense oligonucleotides (ASO) reduces the growth of heterogeneous glioma cells; miR-10b, therefore, represents a unique therapeutic target for treating gliomas including GBM. The present inventors explored the effects of miR-10b gene editing on gliomas such as GBM. Using Clustered Regularly Interspaced Short Palindromic Repeats (CRISPR)/Cas9 system, the effects of miR-10b gene editing on the growth of cultured human glioma cells, tumor-initiating stem-like cells, and mouse GBM xenografts as well as oncogene-induced transformation of normal astrocytes were investigated. As shown herein, glioma cells and GBM are strictly "addicted" to miR-10b, and miR-10b gene ablation is lethal for glioma cell cultures and established intracranial tumors. miR-10b loss-of-function mutations lead to the death of glioma but not other cancer cell lines. Escaped proliferative clones of GBM cells edited in the miR-10b locus were not detected. Finally, neoplastic transformation of normal astrocytes was abolished by the miR-10b-editing vectors. In addition, miR-10a can be targeted as well as miR-10b. There is a single nucleotide difference between miR-10b and 10a, therefore they are expected to target the same genes and be largely functionally redundant; thus the present methods can include targeting miR-10a as an alternative or in addition to miR-10b. The present data show that sgRNA-1 (targets both 10a and 10b) and sgRNA-3 (targets 10b more specifically) both kill glioma cells. This disclosure, therefore, demonstrates the feasibility of gene editing for brain tumors in vivo and provides virus-mediated miR-10a/10b gene ablation as a therapeutic approach that permanently eliminates the key regulator essential for tumor growth and survival.

Thus, provided herein are methods for treating a subject who has cancer, e.g., a glioma, e.g., an astrocytoma, oligodendroglioma, or glioblastoma multiforme (GBM) tumor. The methods include administering to the subject a therapeutically effective amount of a Clustered Regularly Interspaced Short Palindromic Repeats (CRISPR) microRNA-10a/microRNA-10b (miR-10a/10b) editing complex comprising a CRISPR Associated Protein 9 (Cas9) and at least one guide RNA targeting one or both of miR-10a or miR-10b.

In some embodiments, the methods include administering a Cas9 protein. In some embodiments, the Cas9 protein is in a complex with the guide RNA. In some embodiments, the Cas9 protein is administered with a nucleic acid encoding at least one guide RNA targeting one or both of miR-10a or miR-10b.

In some embodiments, the methods include administering a nucleic acid encoding the Cas9 protein. In some embodiments, the nucleic acid encoding the Cas9 protein is administered in a viral vector, e.g., a viral vector selected from the group consisting of recombinant retroviruses, adenovirus, adeno-associated virus, and lentivirus.

In some embodiments, the methods include administering a nucleic acid encoding at least one guide RNA targeting one or both of miR-10a or miR-10b. In some embodiments, the guide RNA targets only miR-10b, or specifically targets miR-10b. In some embodiments, the guide RNA targets both miR-10a.

In some embodiments, the nucleic acid encoding the guide RNA is administered in a viral vector, e.g., a viral vector selected from the group consisting of recombinant retroviruses, adenovirus, adeno-associated virus, and lentivirus.

In some embodiments, the nucleic acid encoding the Cas9 protein and the nucleic acid encoding the guide RNA are administered in and expressed from the same viral vector. In some embodiments, the viral vector is selected from the group consisting of recombinant retroviruses, adenovirus, adeno-associated virus, and lentivirus.

In some embodiments, the methods include administering a guide RNA targeting miR-10b, miR-10a, or both miR-10a and miR-10b, or a pool of guide RNAs targeting 10a and/or 10b.

In some embodiments, the Cas9 is *Streptococcus thermophilus* (ST) Cas9 (StCas9); *Treponema denticola* (TD) (TdCas9); *Streptococcus pyogenes* (SP) (SpCas9); *Staphylococcus aureus* (SA) Cas9 (SaCas9); or *Neisseria meningitidis* (NM) Cas9 (NmCas9), or a variant thereof.

In some embodiments, the Cas9 is SpCas9 or a variant of SpCas9 selected from the group consisting of SpCas9 D 1135E variant; SpCas9 VRER variant; SpCas9 EQR variant; and SpCas9 VQR variant.

In some embodiments, the guide RNA targeting miR-10b is complementary to 17-20 nucleotides of SEQ ID NO:1 or 24, and/or the guide RNA targeting miR-10a is complementary to 17-20 nucleotides of SEQ ID NO:25 or 26.

In some embodiments, the CRISPR miR-10a/10b editing complex is administered systemically, locally to a tumor, or locally to the site of a tumor after complete or partial surgical resection.

In some embodiments, the CRISPR miR-10a/10b editing complex is administered intrathecally.

In some embodiments, the CRISPR miR-10a/10b editing complex is administered in a composition comprising a biodegradable, biocompatible polymer.

In some embodiments, the biodegradable, biocompatible polymer is selected from the group consisting of collagen, ethylene vinyl acetate, polyanhydrides, polyglycolic acid, collagen, polyorthoesters, polyethyleneglycol-coated liposomes, and polylactic acid.

In some embodiments, the subject has a glioma, e.g., an astrocytoma, oligodendroglioma, or glioblastoma multiforme (GBM) tumor.

In some embodiments, the subject has breast cancer or colorectal cancer, and the therapeutically effective amount reduces risk of metastasis, e.g., reduces motility/migration of metastasis.

Also provided herein are Clustered Regularly Interspaced Short Palindromic Repeats (CRISPR) microRNA-10a/microRNA-10b (miR-10a/10b) editing complexes, comprising a CRISPR Associated Protein 9 (Cas9) and at least one guide RNA targeting one or both of miR-10a or miR-10b, for use in the treatment cancer, e.g., a glioma, e.g., an astrocytoma, oligodendroglioma, or glioblastoma multiforme (GBM) tumor. The complexes can comprise protein and nucleic acids, or just nucleic acids.

In some embodiments, the CRISPR miR-10a/10b editing complex is administered as, or formulated to be administered as, a Cas9 protein and guide RNA, e.g., wherein the Cas9 protein is in a complex with the guide RNA, or wherein the Cas9 protein is administered with a nucleic acid encoding at least one guide RNA targeting one or both of miR-10a or miR-10b.

In some embodiments, the Cas9 protein is administered as, or formulated to be administered as, a nucleic acid comprising a sequence encoding a Cas9 protein, e.g., in a viral vector, e.g., a viral vector selected from the group consisting of recombinant retroviruses, adenovirus, adeno-associated virus, and lentivirus.

In some embodiments, the CRISPR miR-10a/10b editing complex is administered as, or formulated to be administered as, a nucleic acid comprising a sequence encoding at least one guide RNA targeting one or both of miR-10a or miR-10b.

In some embodiments, the nucleic acid comprising a sequence encoding the guide RNA is administered, or formulated to be administered, in a viral vector, e.g., a viral vector selected from the group consisting of recombinant retroviruses, adenovirus, adeno-associated virus, and lentivirus.

In some embodiments, the CRISPR miR-10a/10b editing complex is administered as, or formulated to be administered as, a single nucleic acid, preferably a viral vector, comprising a sequence encoding the Cas9 protein and a sequence encoding the guide RNA, and the Cas9 protein and the guide RNA are expressed from the same nucleic acid. In some embodiments, the nucleic acid is a viral vector selected from the group consisting of recombinant retroviruses, adenovirus, adeno-associated virus, and lentivirus.

In some embodiments, the complex is administered as, or formulated to be administered as, a guide RNA targeting miR-10b.

In some embodiments, the Cas9 is *Streptococcus thermophilus* (ST) Cas9 (StCas9); *Treponema denticola* (TD) (TdCas9); *Streptococcus pyogenes* (SP) (SpCas9); *Staphylococcus aureus* (SA) Cas9 (SaCas9); or *Neisseria meningitidis* (NM) Cas9 (NmCas9), or a variant thereof. In some embodiments, the Cas9 is SpCas9 or a variant of SpCas9 selected from the group consisting of SpCas9 D1135E variant; SpCas9 VRER variant; SpCas9 EQR variant; and SpCas9 VQR variant.

In some embodiments, the guide RNA targeting miR-10b is complementary to 17-20 nucleotides of SEQ ID NO:1 or 24, and/or the guide RNA targeting miR-10a is complementary to 17-20 nucleotides of SEQ ID NO:25 or 26.

In some embodiments, the CRISPR miR-10a/10b editing complex is formulated to be administered systemically, locally to a tumor, or locally to the site of a tumor after complete or partial surgical resection.

In some embodiments, the CRISPR miR-10a/10b editing complex is formulated to be administered intrathecally.

In some embodiments, the CRISPR miR-10a/10b editing complex is formulated to be administered in a composition comprising a biodegradable, biocompatible polymer. In some embodiments, the biodegradable, biocompatible polymer is selected from the group consisting of collagen, ethylene vinyl acetate, polyanhydrides, polyglycolic acid, collagen, polyorthoesters, polyethyleneglycol-coated liposomes, and polylactic acid.

In some embodiments, the subject has a glioma, e.g., an astrocytoma, oligodendroglioma, or glioblastoma multiforme (GBM).

In some embodiments, the subject has metastatic cancer, e.g., breast cancer or colorectal cancer, and the present methods reduce risk of metastasis.

As used herein, a sgRNA (Single guide RNA) is a RNA, preferably a synthetic RNA, composed of a targeting sequence and scaffold sequence derived from endogenous bacterial crRNA and tracrRNA; it is used to target Cas9 to a specific genomic locus in genome engineering experiments. The sgRNA can be administered or formulated, e.g., as a synthetic RNA, or as a nucleic acid comprising a sequence encoding the gRNA, which is then expressed in the target cells. "Cas9" refers to CRISPR Associated Protein; the Cas9 nuclease is the active enzyme for the Type II CRISPR system. "nCas9" refers to a Cas9 that has one of the two nuclease domains inactivated, i.e., either the RuvC or HNH domain. nCas9 is capable of cleaving only one strand of target DNA (a "nickase"). "PAM" is a Protospacer Adjacent Motif and is necessary for Cas9 to bind target DNA; Must immediately follow the target sequence. The Cas9 can be administered or formulated, e.g., as a protein (e.g., a recombinant protein), or as a nucleic acid comprising a sequence encoding the Cas9 protein, which is then expressed in the target cells.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

Figure 1A:
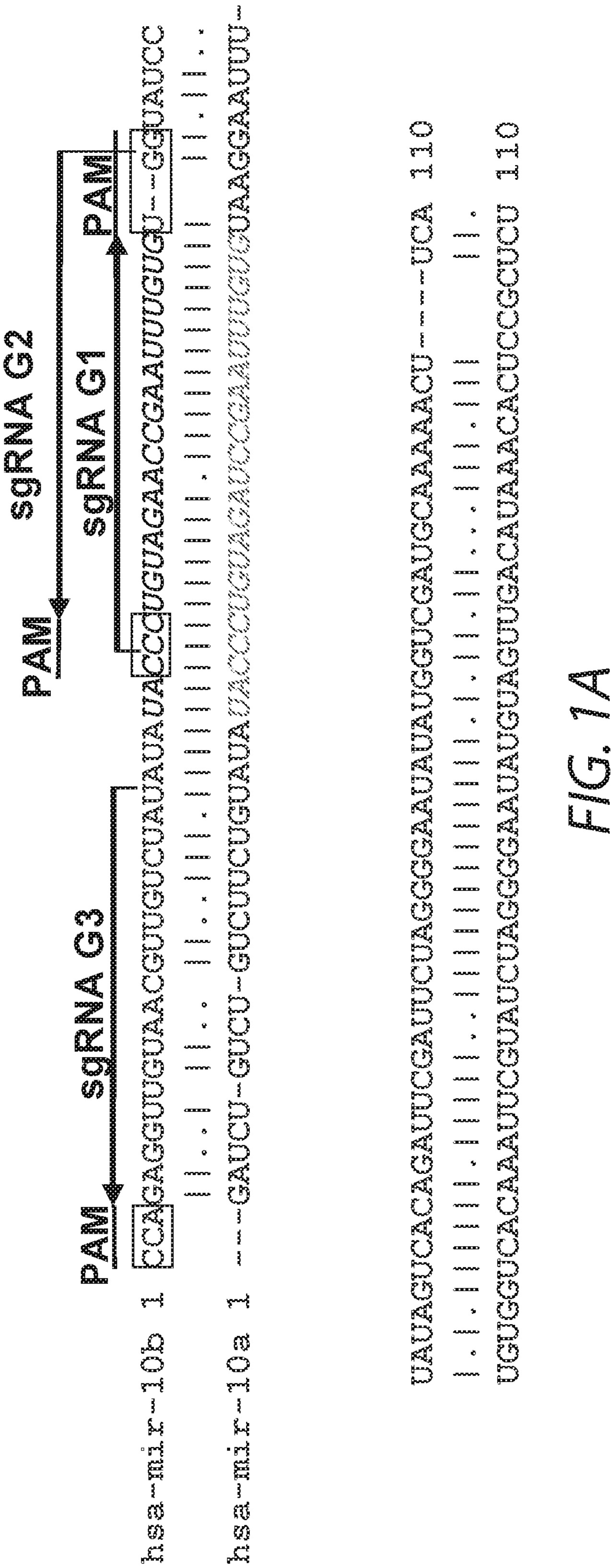
FIG. 1A-C. miR-10b gene is specifically edited by CRISPR-Cas9

(A) Design of alternative sgRNA guides for CRISPR/Cas9 miR-10b editing. The closely related hsa-pre-miR-10b (SEQ ID NO:96) and hsa-pre-miR-10a (SEQ ID NO:97) are aligned. The respective mature sequences are marked in Italic. sgRNA G1-G3 are marked by horizontal arrows, and the corresponding PAMs are shown in boxes. sgRNA G1 and G2 were designed to target the mature miR-10b, and G3—its precursor pre-miR-10b. (B) CRISPR-Cas9 mediated editing of miR-10b locus in LN229 glioma cells, 48 hours post-transfection. The efficiency of miR-10b gene editing with alternative sgRNAs was estimated by Surveyor cleavage assay and bands densitometry (left panel). Cleavage products, indicative of the edited gene, are marked with an arrowhead. miR-10b editing results in a significant down-regulation of mature miR-10b expression (right panel). miR-10b/a levels were analyzed by Taqman qRT-PCR and normalized to the geometrical mean of unaffected miR-99a, miR-125a, and miR-148a. Error bars depict SEM, n=6, *P<0.01, **P<0.005, Student's t test. (C) Assessment of putative off-target effects. Bioinformatically predicted off-targets with a maximum of 3 mismatches for sgRNA G1, G2, and G3 (Table 1). miR-10a represents the major off-target as it differs from miR-10b by a single nucleotide. Surveyor cleavage assay depicts miR-10a editing by sgRNA G1 but not G2 or G3, and the lack of editing of other top predicted genes.

FIGS. 2A-G CRISPR-Cas9 targeting reveals that miR-10b expression is essential for glioma viability (A) miR-10b is efficiently edited in heterogeneous human glioma cell lines and GSC, but not in the non-expressing normal astrocytes and MCF7 cells, as determined by Surveyor assay. Efficient editing of other miRNAs in MCF7 cells is shown as a control. (B) Editing of miR-21, miR-139 and miR-107 results in significant down-regulation of the corresponding mature miRNAs, as analyzed by qRT-PCR. The data was normalized to the geometrical mean of three unaffected miRNAs (miR-99a, miR-125a, and miR-148a). Error bars depict SEM, n=6, *P<0.005, Student's t test. (C) miR-10b gene editing reduces viability of glioma cells, as determined by WST1 assays 48 hours post-transfections for glioma lines, and 5 days post-transfections for GSCs. n=6, *P<0.001, Student's t test. (D) Viability of miR-10b-edited glioma LN229 and U251 cells (edited by lentiviral CRISPR/Cas9, guided by either G1 or G3 sgRNAs) is rescued by the miR-10b mimic transfected at 25 nM, as monitored by WST1 assays 48 hours post-transfection, n=6, *P<0.05. (E) miR-10b does not affect the viability of breast cancer cell lines MDA-MB-231 and MCF7, as determined by WST1 assays. n=6, *P<0.001. (F) qRT-PCR analysis demonstrates negligible miR-10b expression in primary astrocytes and MCF7 cells. The data was normalized to the geometrical mean of unaffected miR-99a, miR-125a, and miR-148a. Error bars depict SEM, n=6, *P<0.05, **P<0.001, Student's t test (G) qRT-PCR analysis of established miR-10b targets BIM, CDKN1A/p21 and CDKN2A/p16, PTBP2, and DGCR14 demonstrates their de-repression in edited LN229 cells. mRNA expression levels were normalized to the geometrical mean of three unaffected genes (GAPDH. 18S rRNA and SERAC1). Error bars depict SEM, n=6, *P<0.05, Student's t test.

Figure 3A:
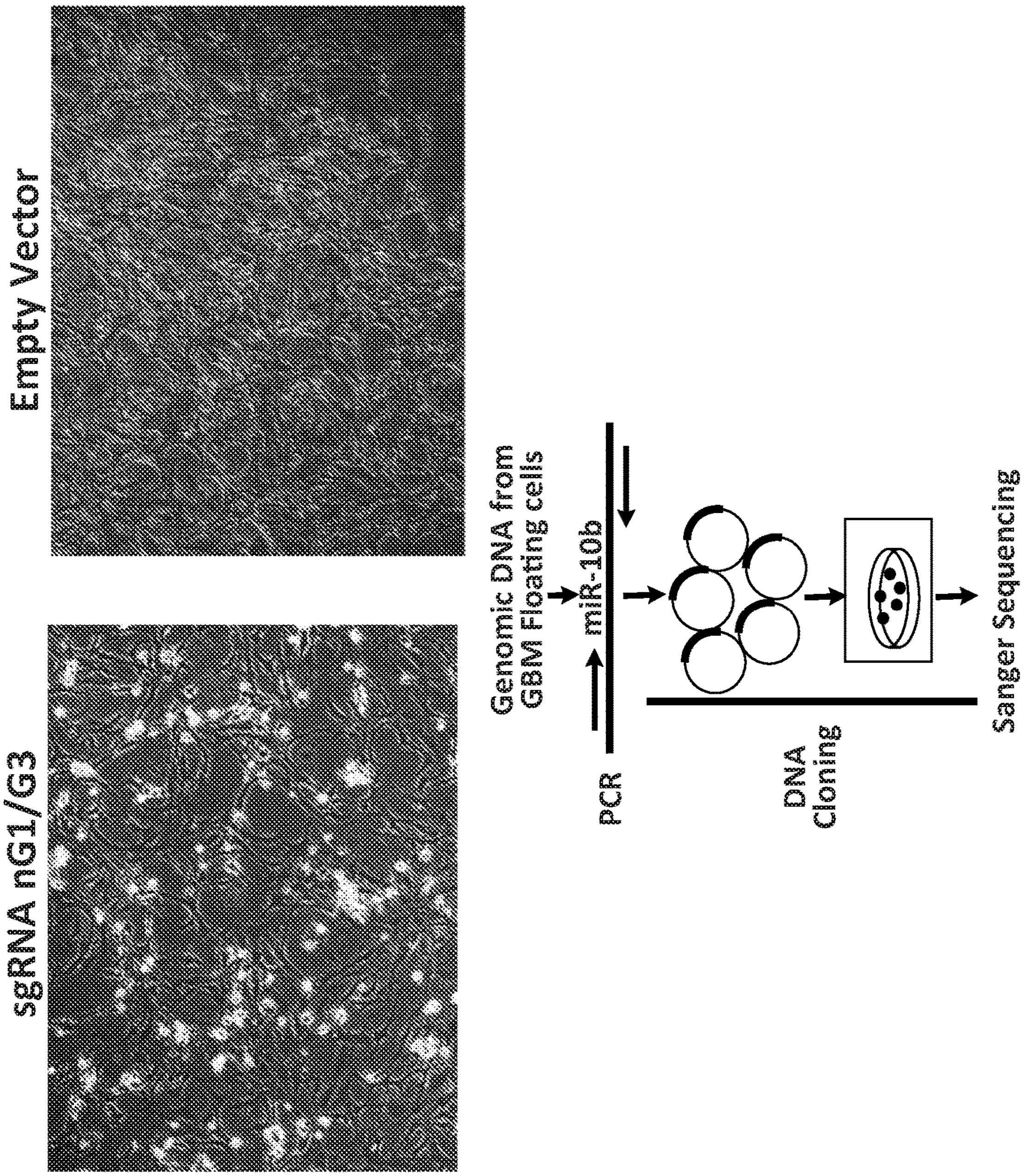
Figure 3B:
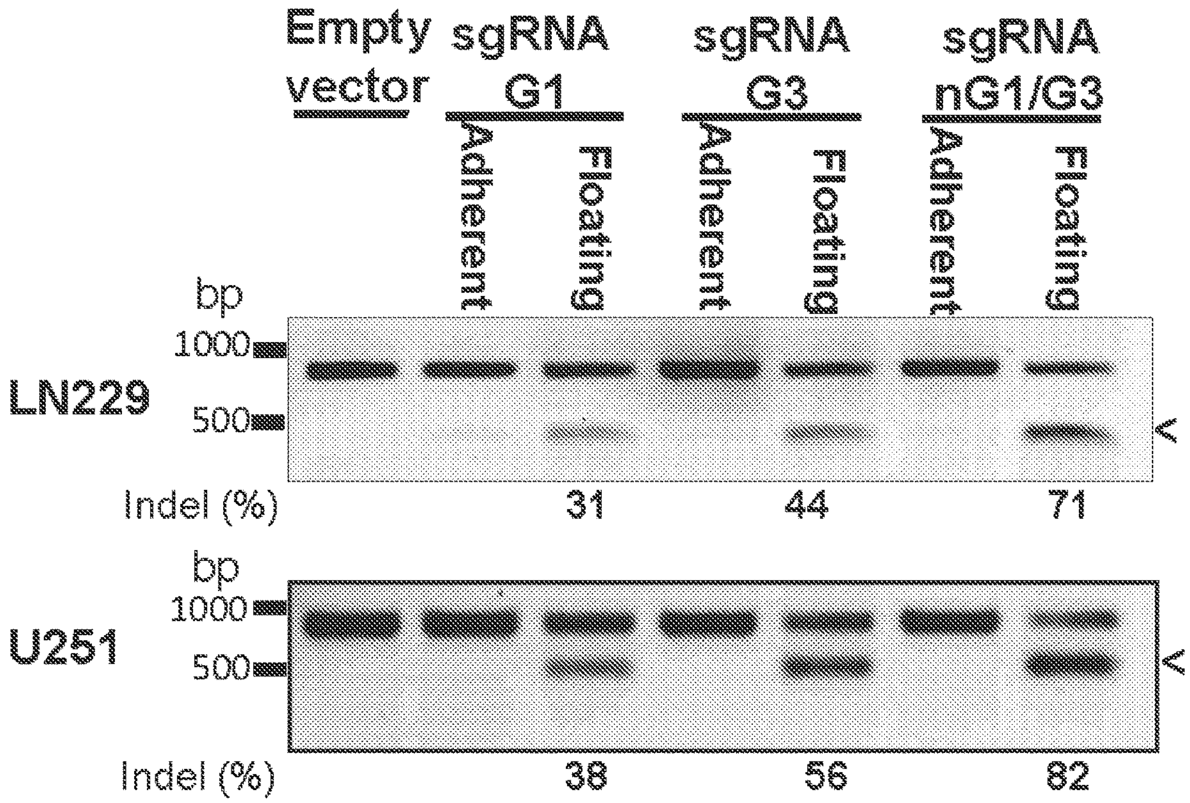
Figure 3C:
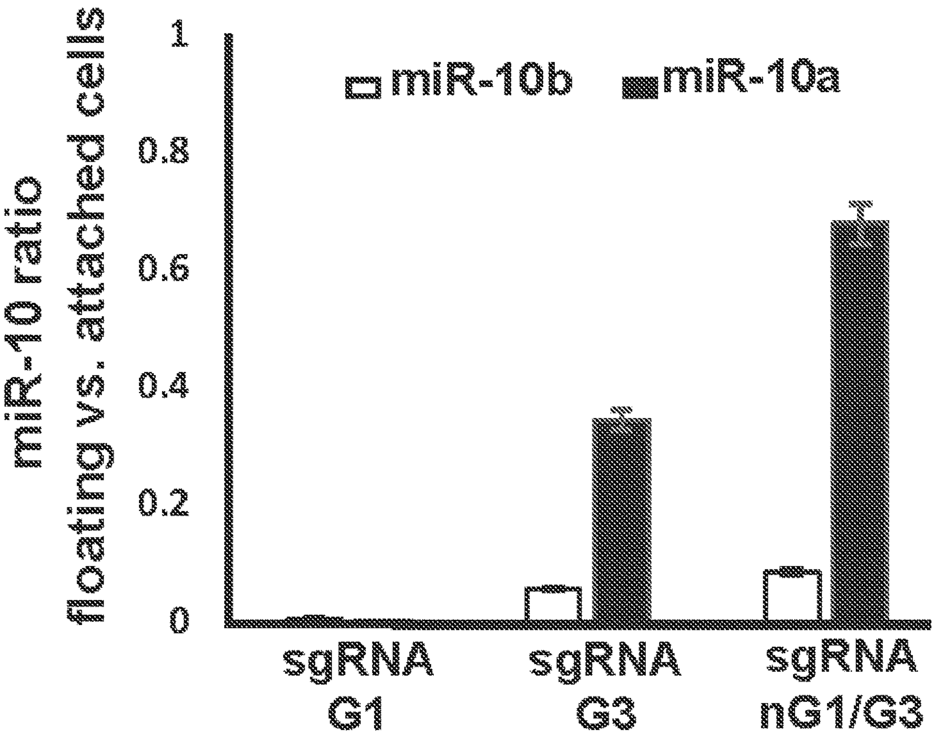

FIGS. 3A-C. CRISPR-Cas9 editing reveals that miR-10b expression is essential for glioma viability (A) Light microscopy images of glioma cells transfected either with the control empty vector or miR-10b targeting vectors demonstrate the appearance of floating apoptotic cells in the edited cultures (upper panels). Schematic view of the analysis of miR-10b DNA locus in the floating cells. The DNA was isolated from the sgRNA nG1/G3-targeted cultures and the miR-10b genomic locus amplified and sequenced. The sequencing results reveal a range of miR-10b mutants, with 17 out of 20 clones mutated in miR-10b locus. (B) Surveyor cleavage assay of the attached and floating populations of LN229 and U251 glioma cells demonstrates that miR-10b is edited preferentially in floating cells, whereas the unedited cells remain attached. (C) miR-10b levels are reduced in the floating apoptotic but not in the attached viable LN229 cells.

FIGS. 4A-E. Intratumoral injections of lentiviral miR-10b editing vectors ($10^5$ TU) strongly impair tumor growth of established orthotopic LN229 GBM (A) Immunohistochemistry of brain sections exhibits specific Cas9 staining in the tumor areas, marked by the mCherry fluorescence. (B) Western blot analysis (top panel) and Surveyor cleavage assay (bottom panel) demonstrate, correspondingly, Cas9 expression and efficient miR-10b editing in infected tumor xenografts but not control tumors 3 days after infections with G1 and G3 sgRNAs. Cleavage products, indicative of the edited miR-10b gene, are marked with an arrowhead. (C) Tumor growth was monitored by luciferase imaging in vivo. There were 6-7 mice per group at the treatment initiation, and each dot represents an animal/tumor. The insert illustrates tumor imaging in representative animals. *P<0.005 by unpaired ANOVA test. (D) H&E histology and mCherry fluorescence of the LN229 intracranial GBM demonstrate markedly reduced tumors in G1 and G3 sgRNAs-targeted groups. Scale bar=500 μm for H&E, 200 μm for IF. "T" indicates tumor and "B"—brain tissue. (E) miR-10b gene editing helps maintain the body weight in mice bearing intracranial tumors. N=6 animals per group. *P<0.005, Student's t test.

FIGS. 5A-H. Lentivirus-mediated miR-10b gene editing abolishes neoplastic transformation of oncogene-induced astrocytes (A) Transductions of human and mouse primary astrocytes and neurons with miR-10b editing lentivirus at the MOI levels that led to similar levels of Cas9 expression, as assessed by Western blot with Cas9 antibody (low panel), does not cause miR-10b gene editing. 100% of glioma LN229 cells were Cas9-positive in these conditions. Human Brain Microvascular Endothelial Cells (HBMECs) were edited in miR-10b gene by high-titer virus with low efficiency (11% versus 53% in glioma cells, at 10-fold higher viral titer). The relative MOI required for similar Cas9 expression in these cells is indicated. (B) miR-10b gene editing reduces the viability of glioma cells but not human and mouse primary astrocytes, neurons, and HBMEC, as determined by WST1 assays 48 hours post-transduction. Transduction conditions and MOI match those utilized in panel A. n=6, *P<0.001, Student's t test. (C) miR-10b levels in mouse primary astrocytes induced for transformation by H-RasG12V/Ad-E1, and subsequently transduced with miR-10b-editing vectors for two weeks, as determined by qRT-PCR and normalized to the geometrical mean of unaffected miR-99a, miR-125a, and miR-148a. (D) Transformed primary astrocytes exhibit the reduced levels of miR-10b targets p21, p16, BIM, and PTBP2, relative to the corresponding naive cultures. qRT-PCR data was normalized to the geometrical mean of three unaffected genes (GAPDH. 18S rRNA and SERAC1).Error bars depict SEM, n=3, *P<0.05 Student's t test. (E) miR-10b editing reduces the number of transformed colonies. Crystal violet staining and quantification of the colonies are shown two weeks after infections with miR-10b-editing vectors. (F) Transformed, miR-10b-expressing mouse astrocytes become editable in miR-10b locus. (G) miR-10b editing of transformed astrocytes induces cell death, similarly to the effect on glioma cell lines. The scale bar=20 μm (H) Relative miR-10b levels in glioma and various brain-derived cell types were assessed by qRT-PCR analysis and the data was normalized to the geometrical mean of unaffected miR-99a, miR-125a, and miR-148a n=6, *P<0.001 Student's t test.

Figure 6:
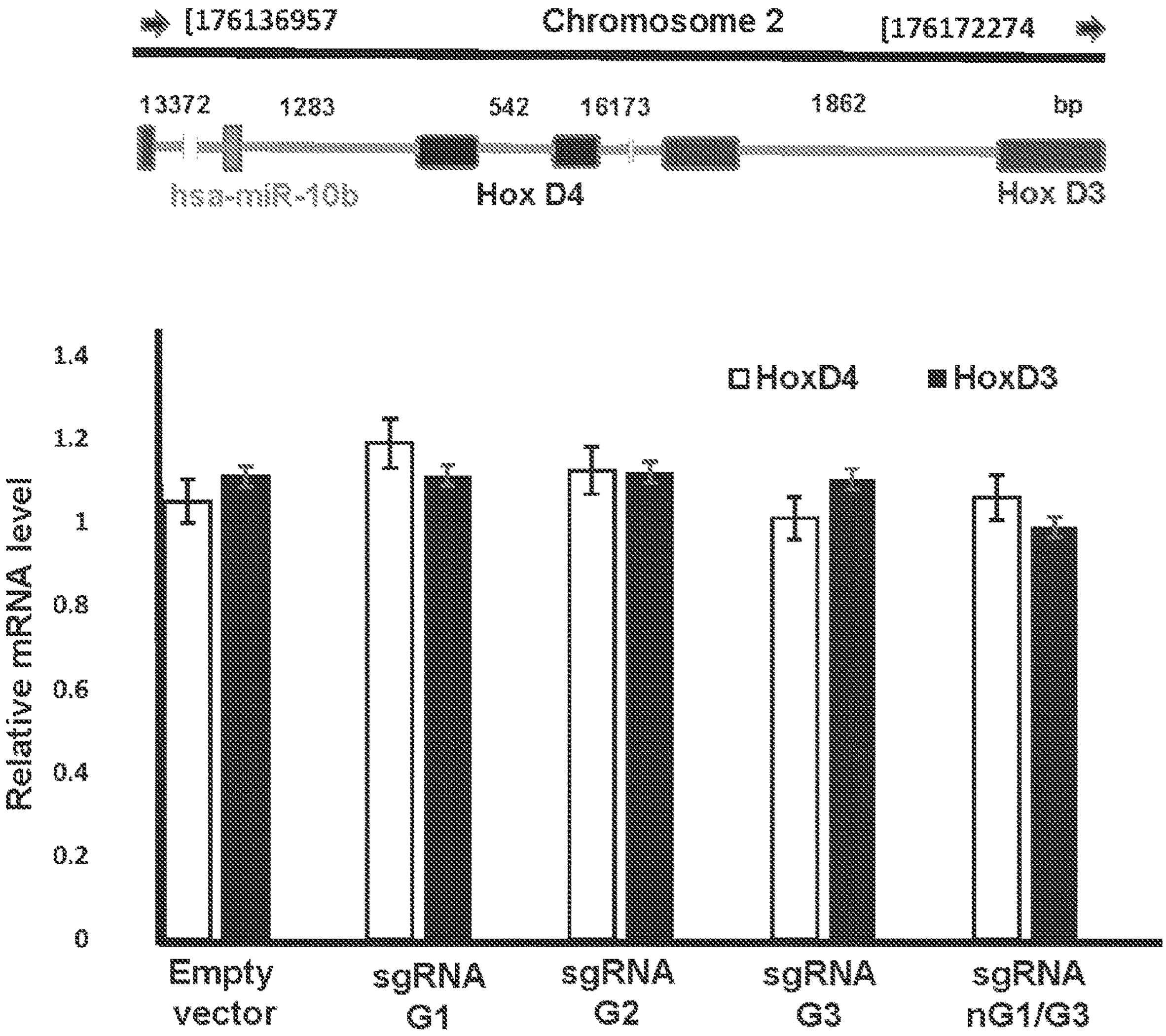

FIG. 6: miR-10b editing with G1-G3 sgRNAs does not affect the expression of adjacent HOXD4 and HOXD3 genes. Schematic presentation of miR-10b located upstream of the HOXD4 and embedded in the first intron separating two non-coding exons of HOXD3. Expression levels of HOXD3 and HOXD4 mRNAs were examined in LN229 glioma cells 48 hours after transfections with G1-G3 sgRNAs or double sgRNA guide nG1/G3.

Figure 7:
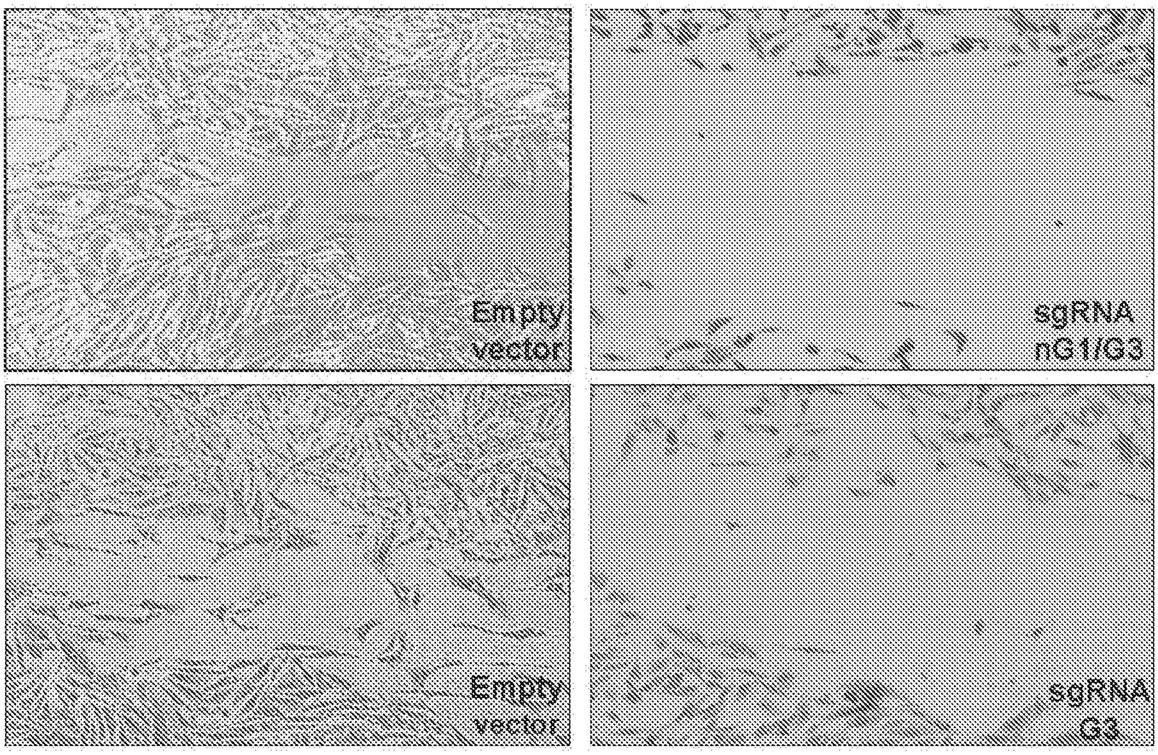

FIG. 7. CRISPR-Cas9/G3 mediated editing of miR-10b reduces migration of MDA-MB-231 cells as indicated by the scratch motility assay. The cell viability was not affected.

Figure 8A:
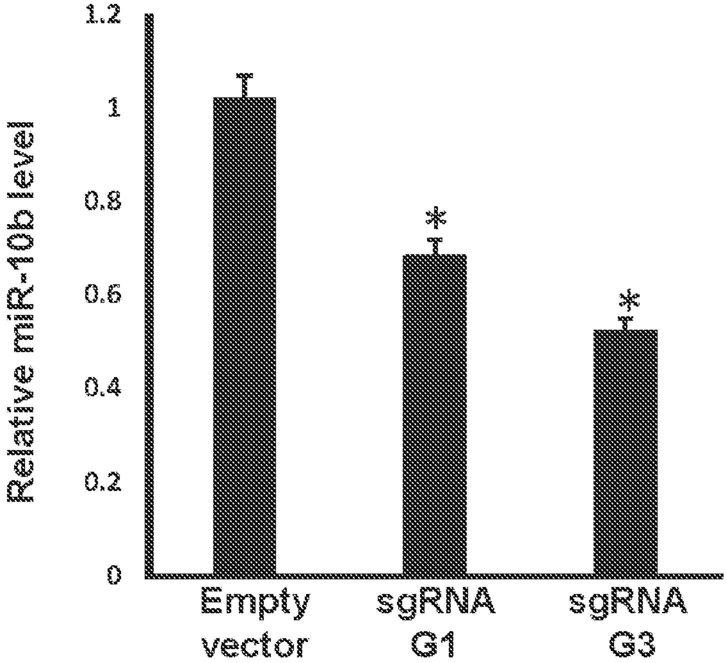
Figure 8B:
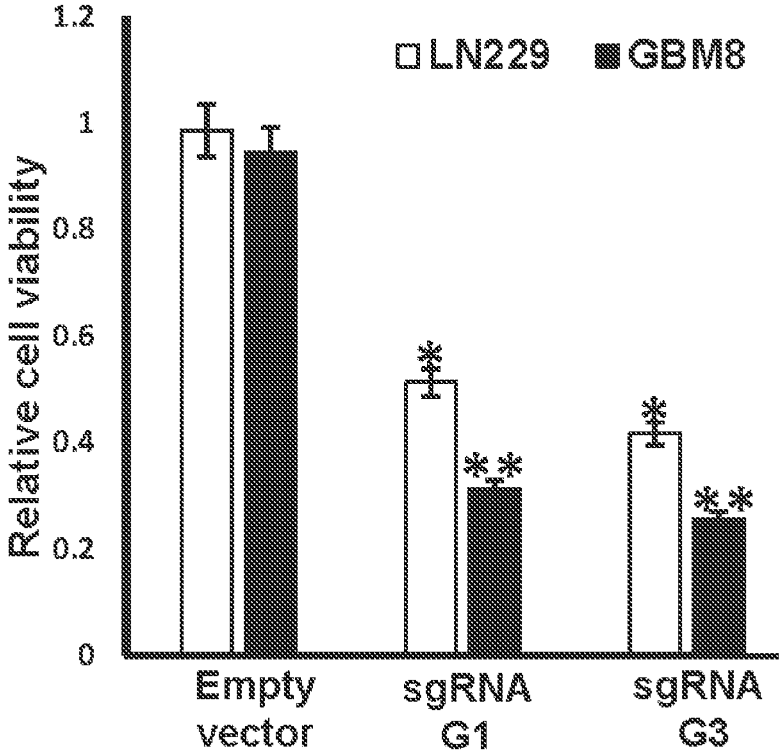

FIGS. 8A-8B. Lentivirus-mediated miR-10b CRISPR-Cas9 editing reduces (A) miR-10b levels and (B) glioma cell viability as monitored by qRT-PCR and WST1 assays, respectively.

Figure 9:

FIG. 9. Functional validation of lentivirus nCas9 in LN229 cells demonstrates efficient editing guided by a pair of sgRNAs targeting both strands (sgRNA nG1/G3), but not individual G1 or G3 sgRNAs.

Figure 10A:
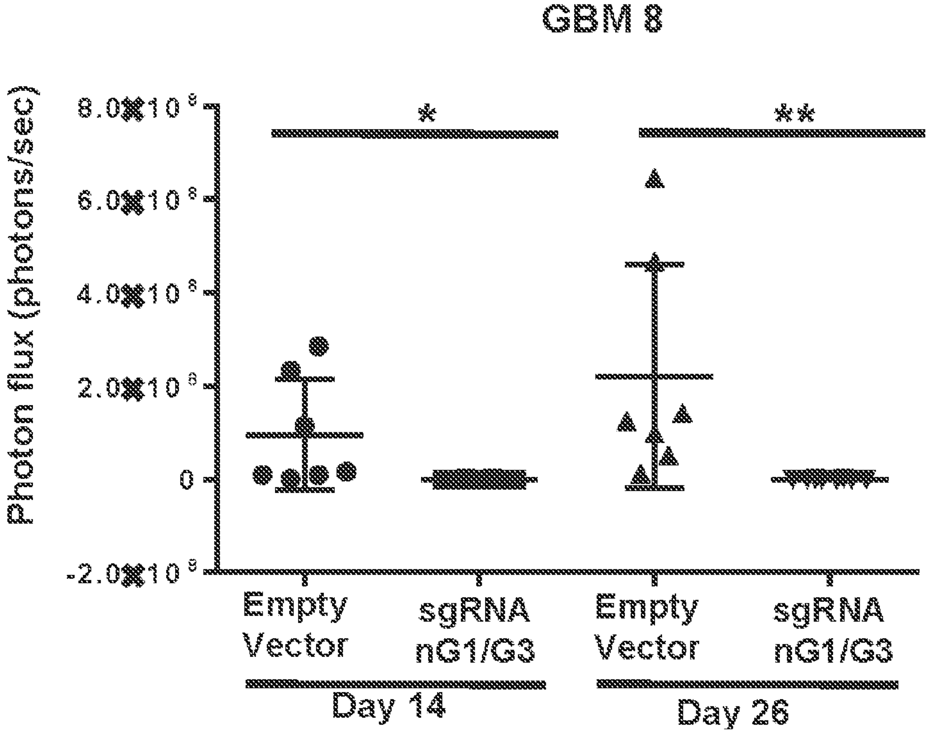
Figure 10B:
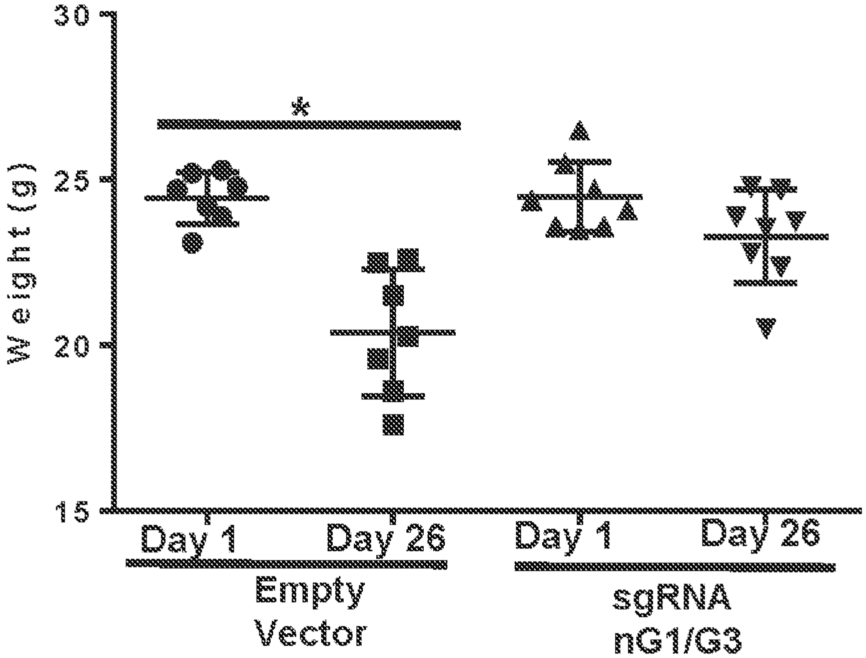

FIGS. 10A-B. Intratumoral injections of lentiviral miR-10b editing nCas9 "nickase" vectors ($3\times10^5$ TU) strongly impair the growth of established orthotopic GBM8. A. Tumor growth was monitored by luciferase imaging in vivo. There were 7-8 mice per group at the treatment initiation, and each dot represents an animal. The insert illustrates tumor imaging in representative animals. *P<0.05, **P<0.005 by Student's t-test. B. miR-10b gene editing helps maintain the body weight in mice bearing intracranial tumors. n=7-8 animals per group. *P<0.005.

Figure 11:
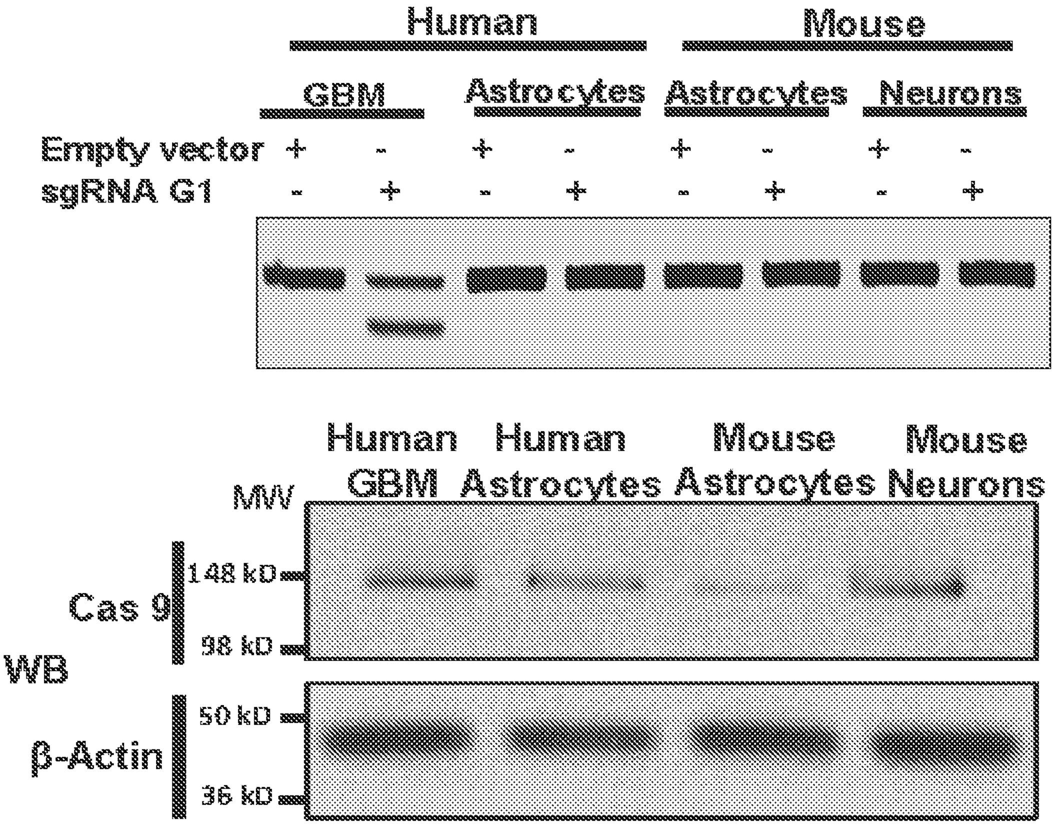

FIG. 11. Transduction of normal mouse and human primary neuroglial cultures with lentiviral miR-10b editing CRISPR/Cas9 vectors at $3\times10^5$ TU does not result in miR-10b gene editing. Western blot analysis (lower panel) demonstrates the corresponding Cas9 expression at 48 h post-transduction.

Figure 12:
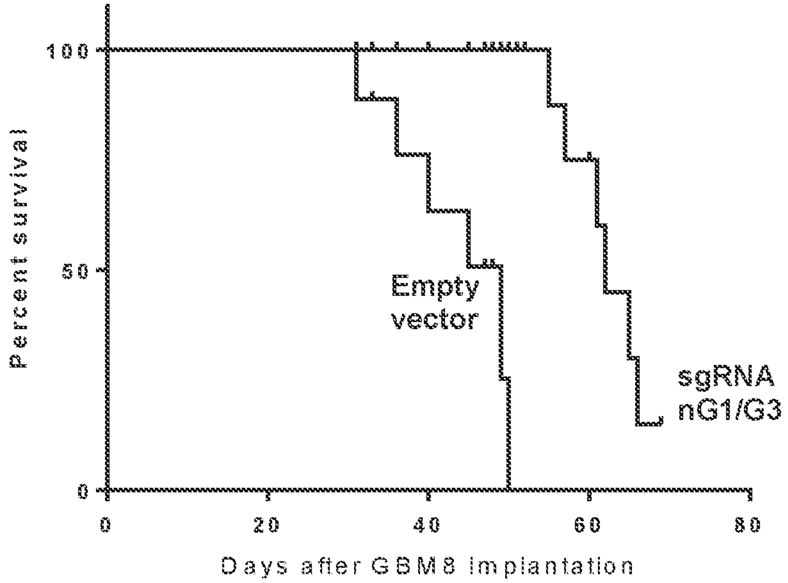

FIG. 12. miR-10b editing significantly extends animal survival in orthotopic GBM models. miR-10b editing (by lentivirus) significantly extended animal survival, analyzed by Kaplan-Meier plot. N=8 mice per group. P=0.0001 by log-rank (Mantel-Cox) test.

Figure 13:
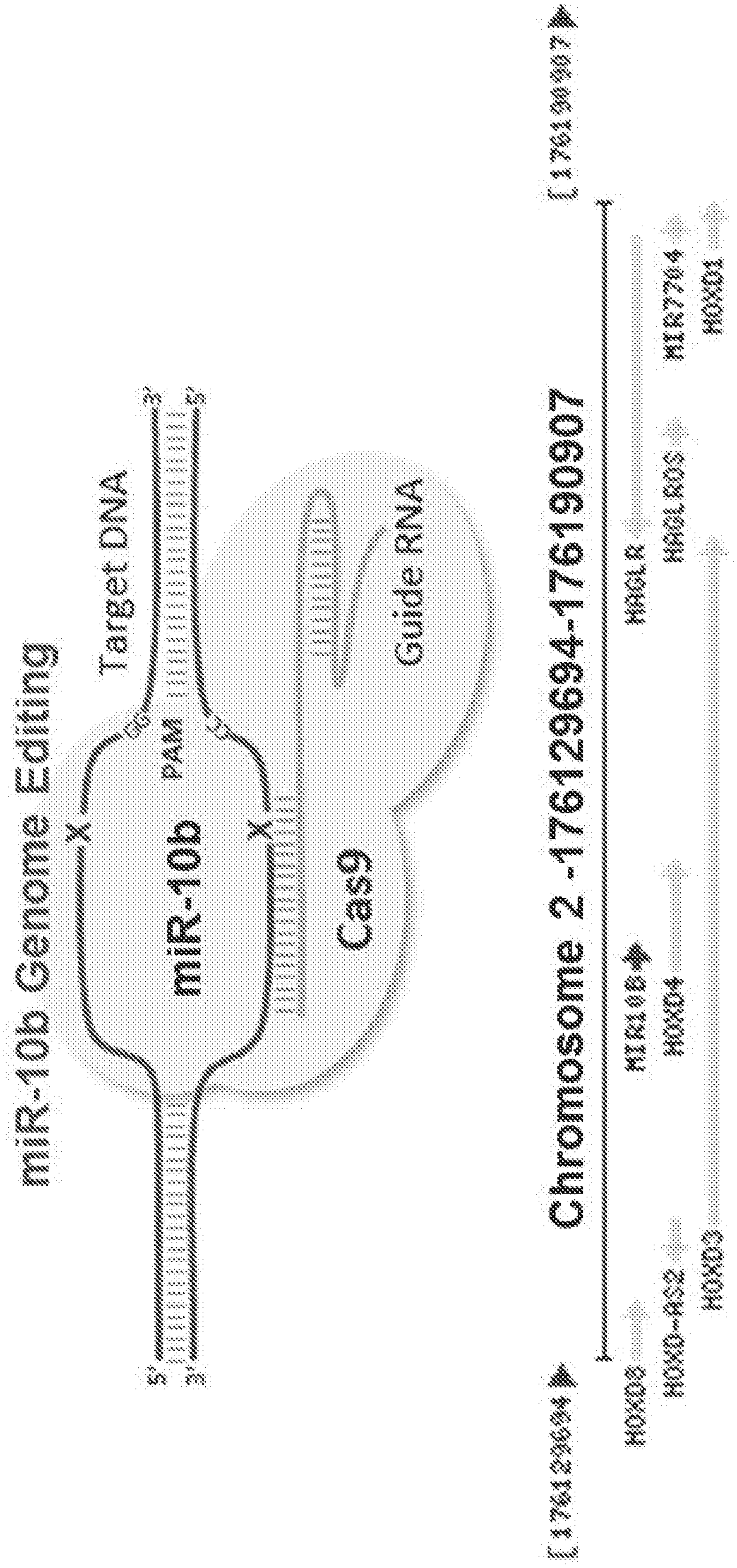

FIG. 13. miR-10b editing as therapeutic approach for human Glioblastoma. An exemplary illustration showing miR-10b editing using CRISPR Cas9. miR-10b gene ablation leads to eradication of GBM, but is uneditable in and thus does not affect normal brain cells.

DETAILED DESCRIPTION

Mounting evidence indicates that glioma and GBM growth and invasiveness are closely regulated by miRNAs (reviewed in 1). Micro RNA 10b (miR-10b) is embedded within the HOXD genomic locus and implicated in proliferation, invasion, and metastasis of various types of malignancies including gliomas such as GBM (reviewed in 2, 3). miR-10b is especially notable in brain tumors due to its unique expression pattern: while virtually undetectable in the normal brain, it becomes extremely abundant in the majority of low and high-grade gliomas across all subtypes, as well as metastatic brain tumors (3-6). Breast cancer patients with brain metastases have significantly higher miR-10b levels compared to patients with metastases in other organs (7, 8). Inhibition of miR-10b by chemically modified antisense oligonucleotides (ASO) reduces growth and invasion of cultured glioma cells (4, 9), and metastasis in aggressive cancer models (10, 11). Recent work on highly invasive and aggressive intracranial glioma models demonstrated that ASO inhibitors of miR-10b reduce GBM growth in mice (12). However, the effects observed in the orthotopic GBM models were transient, with disease relapse due to both low-efficiency uptake and non-uniform distribution of the ASO in intracranial GBM.

There are only a few examples of true onco-miR dependencies known for cancer cells. The present data indicates that high expression of the WT miR-10b gene is essential for glioma, whereas loss-of-function mutations lead to the lethality of heterogeneous glioma cells and tumor-initiating GSC. Alternative sgRNA guides targeting either miR-10b alone or together with its closely related paralog miR-10a produced a diverse range of mutants, none of which were viable. The loss-of-function mutations in miR-10b alone were sufficient to cause the lethality, validating the key role of miR-10b in the sustained growth and survival of glioma. Specifically, mutated nCas9 guided by the G1/G3 sgRNAs had detrimental effects on glioma cells by reducing the levels of miR-10b and without affecting the levels of miR-10a gene, suggesting the efficacy of the miR-10b single-gene targeting approach for GBM. Since miR-10a and miR-10b differ in one nucleotide and are largely functionally redundant, the relative efficacy of miR-10a targeting remains to be evaluated. Of note, miR-10b is expressed in normal extracranial tissues; nevertheless, its activity in these tissues seems to be dispensable as the initial analysis of miR-10b knock-out mice has no apparent pathological phenotype (Mir10b$^{tm1Mtm}$/Mmjax; MMRRC Stock No: 36061-JAX). Glioma addiction to miR-10b appears, therefore, truly as a tumor-specific trait, probably associated with de-repression of the gene in the brain microenvironment where it is normally silenced. A unique onco-miR-dependence of glioma and GBM also suggests that the tumor could be eradicated by targeting a single miRNA gene.

Administration of synthetic miR-10b inhibitors caused potent but transient effects on orthotopic GBM in aggressive GSC-based models (12). This may have been due to both poor uptake and distribution of the ASO in intracranial GBM, and dilution of the drug in the actively growing tumor. Gene editing, based on permanent miR-10b inactivation, may provide an alternative strategy, eliminating the need for continuous delivery of anti-miRs to intracranial brain tumors and improving the efficacy of tumor cell destruction. Interestingly, even moderately efficient miR-10b gene editing of GBM8 glioma stem cells led to disaggregation and massive death of glioma spheres, suggesting that disruption of this core cell population may have detrimental effects on the tumor growth. Using lentiviral CRISPR-Cas9 targeting, the effects of miR-10b ablation were examined on highly aggressive human GBM xenografts. Remarkably efficient Cas9 expression and miR-10b editing throughout the tumor resulted in the permanent ablation of miR-10b and near-eradication of orthotopic GBM tumors. The data suggest that less-than-100% efficient editing and miR-10b ablation is sufficient for potent inhibition of GBM growth. The lentiviral editing vector used herein caused strong effects on glioma growth both in vitro and in vivo. The effects may appear stronger in vivo due to the longer duration of the experiment; however, miR-10b editing in cultures also resulted in death of the entire population, when analyzed over longer time. Overall, these data provide proof-of-principle for the single-target gene editing based therapeutic strategy for malignant gliomas, and may also apply to other miR-10b dependent metastatic cancers (11, 21).

Figure 2A:
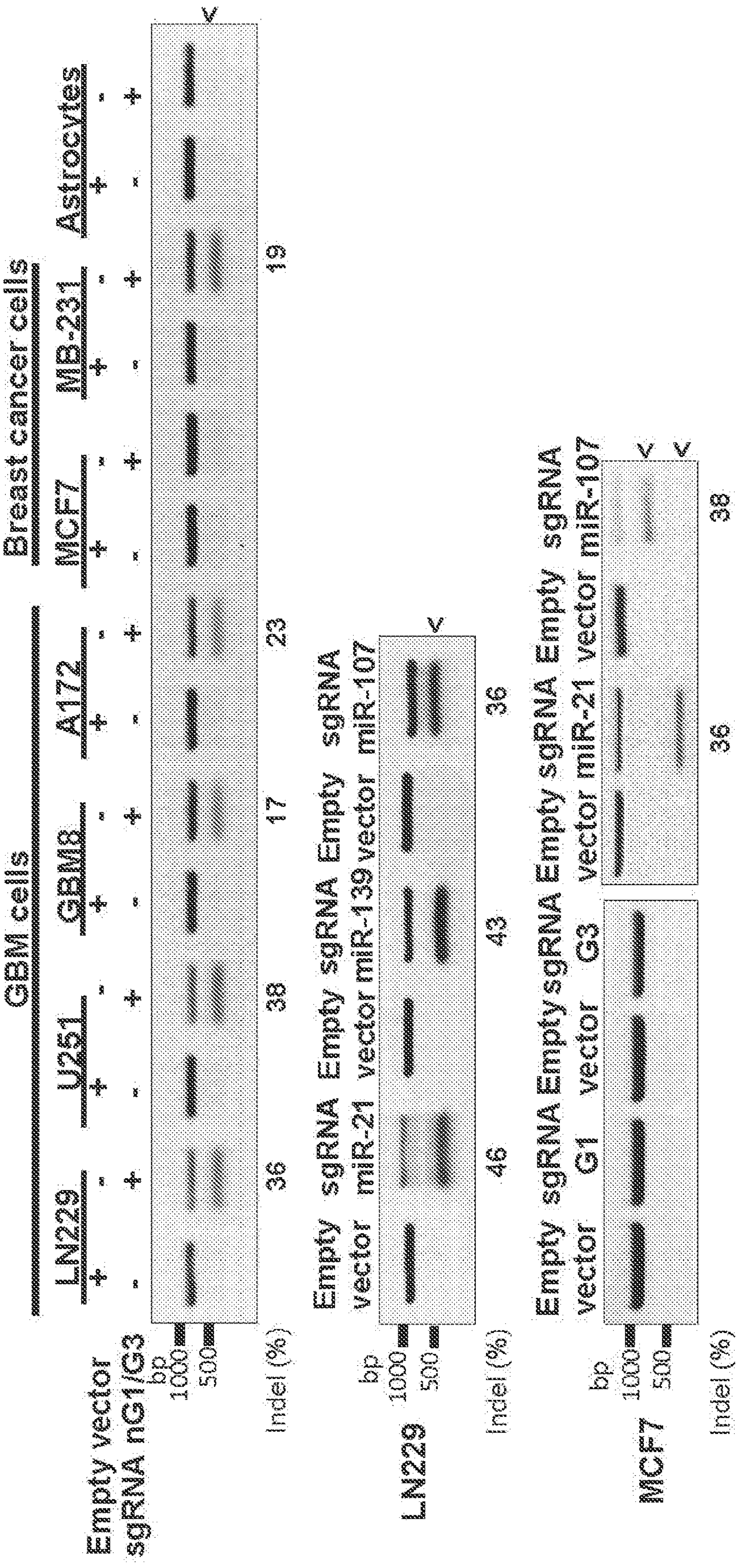
Figure 2B:
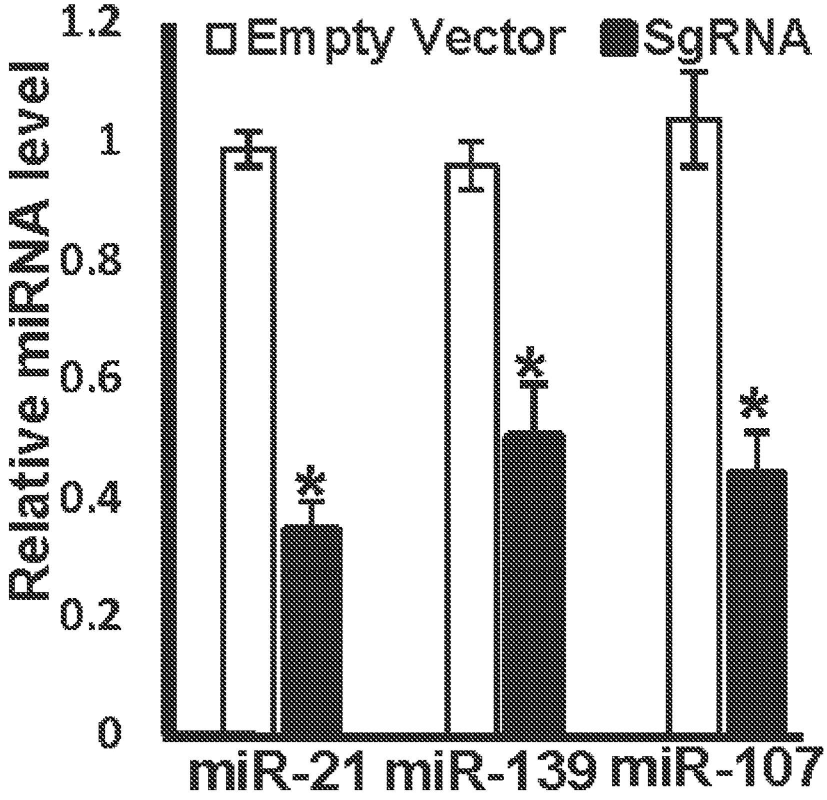

A limitation of the CRISPR-Cas9 technology, and particularly its clinical application, is associated with its restricted specificity (reviewed in 22). Bioinformatics analysis suggested only a few potential high-ranked protein-coding off-targets (mismatched target sites) for the designed miR-10b SpCas9 sgRNAs (FIG. 1C and Table 1); none of them appeared to be actually edited in the present experiments.

efficient editing of other highly expressed miRNAs in these cells (FIG. 2A). This data suggested that miR-10b is not edited in normal neuroglial and other non-expressing cells due to the compact chromatin structure of the locus, and not merely lower efficiency of transfection or transduction. Of note, human brain-derived microvascular endothelial cells do express substantial levels of miR-10b. While the functional role of miR-10b in these cells requires further investigation, the present results demonstrate that miR-10b gene editing (which is less efficient than in glioma cells) does not affect their phenotype. Importantly, the lack of toxicity for normal brain cells suggests a reasonable therapeutic window for miR-10b editing in glioma in vivo, further validates the high targeting specificity, and paves the way for its clinical development.

The present methods of miR-10b-editing viral therapy for glioma, e.g., GBM, patients can include at least a one-time treatment with local administration of the viral vector to the surgical bed, immediately after tumor resection. The lentiviral vectors utilized in the present experiments in vivo transduce dividing as well as quiescent cells. This can be viewed as a major advantage for cancer gene therapy in general, as within a short treatment window most tumor cells (and especially GSC) do not divide. Since miR-10b editing prevents neoplastic transformation of astrocytes and selectively eradicates the transforming cells (FIG. 5), in addition to malignant tumor cells this approach may target the brain cells undergoing early stages of gliomagenesis. Therapeutic gene editing using high viral titers applied locally to the surgical cavity, may also prove to be effective for targeting infiltrating tumor cells (26, 27).

TABLE 1

Predicted Off-Targets for the Designed miR-10b SpCas9 sgRNAs

| | Top predicted off-targets | mismatche(s) & position(s) | Locus |
|---|---|---|---|
| | miRNA-10a | 1 MMs [11] | Chr16: +64668475 |
| sgRNA G1 | Asparagine amidohydrolase (NTAN1) | 3 MMs [9:11:12] | Chr16: −15151834 |
| | Sulfotransferase (ST1A3) | 3 MMs [5:9:13] | Chr2: +108886423 |
| | miRNA-10a | 3 MMs [1:2:15] | Chr16: +64668475 |
| sgRNA G2 | Cytosolic purine 5'-nucleotidase (5NTC) | 3 MMs [2:6:13] | Chr10: +104928080 |
| | Phosphodiesteras eta-1 (PLCH1) | 3 MMs [4:11:13] | Chr3: +155214975 |
| sgRNA G3 | Leucine-rich repeat transmembrane protein (FLRT2) | 3 MMs [2:7:9] | Chr14: −87587093 |
| | Collagen alpha-a1 (III) chain preportein (COL3A1) | 3 MMs [4:10:15] | Chr2: −189649274 |

To start evaluating the therapeutic potential of miR-10b editing in the brain and assess its safety, the effects of miR-10b ablation were tested in the normal cells of brain tumor microenvironment in vitro. Major cell types of the brain, including neurons, astrocytes, microglia, and neuroprogenitors express very low, or undetectable levels of miR-10b, while exhibiting low levels of miR-10a (4). Although CRISPR-Cas9 system can target genes in any cell type including postmitotic neurons (23, 24), the efficacy of editing genes that are not actively transcribed in a specific cellular context, and might be less accessible by Cas9-sgRNA due to their epigenetic state and chromatin structure, is presently unknown and expected to be low (25). The present data indicated that CRISPR-Cas9 plasmid- and virus-mediated miR-10b targeting did not cause locus editing in normal brain cells and did not affect the viability of mouse primary astrocytes or neurons (FIGS. 2A and 5A); neither did the miR-10b ASO inhibitors (4). Additional experiments on human MCF7 cells that express only negligible miR-10b levels also demonstrated the lack of miR-10b editing and no visible phenotypic effects, despite the An advantage of a locally applied lentivirus pseudotyped with the VSV-G glycoprotein is its inactivation by human serum (28) that would reduce systemic effects. Although the application of human lentiviral gene therapy is hampered by the risk of carcinogenesis by random proviral integration into the genome of normal somatic cells, future studies should determine if this risk is acceptable for local glioma treatment, given the lack of efficacious drugs and poor life expectancy of patients with the disease. Importantly, the identification of *Staphylococcus aureus* (SaCas9) and other smaller Cas9 enzymes that can be packaged into adeno-associated viral vectors highly stable and effective in vivo (29-31), easily produced, approved by FDA for other applications, and tested in multiple clinical trials, paves new avenues for therapeutic gene editing. Further optimization of the targeting vectors with increased tropism for glioma cells, as well as in-depth investigation of potential neurotoxic effects have to be performed before clinical applications of this promising new strategy.

Methods of Treatment

The methods described herein include methods for the treatment of glioma, e.g., GBM, astrocytoma or oligodendroglioma, e.g., a glioma that has increased levels of miR-10b expression (increased as compared to normal tissue or to other gliomas). Generally, the methods include administering a therapeutically effective amount of a miR-10b gene editing complex as described herein, to a subject who is in need of, or who has been determined to be in need of, such treatment.

As used in this context, to "treat" means to ameliorate at least one clinical parameter of the glioma; thus, in some embodiments, administration of a therapeutically effective amount of a compound described herein for the treatment of glioma results in a reduction in tumor size; a reduction in tumor growth rate; a reduction in risk of tumor regrowth or recurrence; an improved prognosis; or an increase in survival time. In some embodiments, the treatment improves one or more symptoms of the glioma.

In some embodiments, the subject has a cancer that may become metastatic, e.g., breast cancer or colorectal cancer, e.g., wherein metastasis is associated with miR-10b. Metastasis has been shown to be linked to miR-10b in a number of cancers; see, e.g., Ma et al., Tumour invasion and metastasis initiated by microRNA-10b in breast cancer. Nature 449: 682-8 (2007); Li et al., microRNA expression profiles in human colorectal cancers with brain metastases. Oncol Lett 3: 346-50 (2012); Ahmad et al., Up-regulation of microRNA-10b is associated with the development of breast cancer brain metastasis. Am J Transl Res 6: 384-90 (2014); Parrella et al., Evaluation of microRNA-10b prognostic significance in a prospective cohort of breast cancer patients. Mol Cancer 13: 142 (2014); Lu et al., The association between abnormal microRNA-10b expression and cancer risk: a meta-analysis. Sci Rep 4: 7498 (2014). The methods described herein can be used to reduce the risk or likelihood that the subject who has cancer, e.g., breast or colorectal cancer, will develop metastatic disease, e.g., a brain metastasis.

A diagnosis of a glioma (e.g., identification of a subject with glioma, e.g., GBM, astrocytoma or oligodendroglioma) can be made based on methods known in the art. Gliomas such as GBM commonly presents with symptoms that include the following: progressive neurologic deficit; motor weakness; headache; generalized symptoms of increased intracranial pressure or neurologic symptoms including headaches, nausea and vomiting, memory loss, personality changes, confusion, and cognitive impairment; and seizures. Focal signs can include hemiparesis, sensory loss, visual loss, and aphasia. A diagnosis is typically made based on imaging studies including computed tomography (CT), magnetic resonance imaging (MRI), with and/or without contrast; positron emission tomography (PET); and/or magnetic resonance spectroscopy (MRS); a biopsy can be done to confirm the diagnosis, usually during surgical resection or using a stereotactic needle biopsy.

Presently, standard therapy includes maximal surgical resection (preferably gross total resection), radiotherapy, and concomitant and adjuvant chemotherapy, e.g., with temozolomide, nitrosoureas (e.g., carmustine [BCNU]), MGMT inhibitors (e.g., O6-benzylguanine); platinum-containing agents, e.g., cisplatin; anti-VEGF agents, e.g., bevacizumab (alone or with irinotecan); and tyrosine kinase inhibitors (e.g., gefitinib, erlotinib).

CRISPR miR-10a/10b Gene Editing Complexes

The present methods include the use of CRISPR miR-10b gene editing complexes. The methods can include the use of expression vectors for in vivo transfection and expression of a Cas9 protein and suitable guide RNAs targeting miR-10b. Alternatively, or in addition, the methods can include the use of purified Cas9 proteins complexed with suitable guide RNAs targeting miR-10b.

In addition, miR-10a can be targeted as well as miR-10b. There is a single nucleotide difference between miR-10b and 10a, therefore they are expected to target the same genes and be largely functionally redundant; thus the present methods can include targeting miR-10a as an alternative or in addition to miR-10b. The present data show that sgRNA-1 (targets both 10a and 10b) and sgRNA-3 (targets 10b more specifically) both kill glioma cells.

Nucleic Acids Encoding a CRISPR miR-10a/10b Gene Editing Complex

The present methods include the delivery of nucleic acids encoding a CRISPR miR-10b gene editing complex. The gene editing complex includes a Cas9 editing enzyme and one or more guide RNAs directing the editing enzyme to miR-10b. In some embodiments, the guide RNA may also direct the editing enzyme to miR-10a, e.g., to miR-10a/10b (i.e., one or both of miR-10a and miR-10b).

Guide RNAs Directing the Editing Enzyme to miR-10a/10b

The gene editing complex also includes guide RNAs directing the editing enzyme to one or both of miR-10a and miR-10b, i.e., comprising a sequence that is complementary to the sequence of a nucleic acid encoding miR-10a or miR-10b, and that include a PAM sequence that is targetable by the co-administered Cas9 editing enzyme. In some embodiments, the precursor sequence is targeted by the guide RNA., i.e., comprising a sequence that is complementary to the sequence of a nucleic acid encoding miR-10a or miR-10b. In some embodiments, the precursor sequence is targeted by the guide RNA.

The gene encoding the human miR-10b precursor is at nucleotides 176,150,303-176,150,412 of chromosome 2 (see GenBank Acc. No. NC_000002.12). The sequence of human gene coding for pre-microRNA-10b (MIR10B) (GenBank Acc. No. NR_029609.1) is 110 nucleotides, as follows: CCAGAGGTTGTAACGTTGTC-TATATATACCCTGTAGAACCGAATTTGTGTGG TATCCGTATAGTCACAGATTCGATTCTAGGG-GAATATATGGTCGATGCAAAA ACTTCA (SEQ ID NO:1). Exemplary miR10b target sequences are shown in Tables A-C. An exemplary miR-10b primary transcript (pri-miR-10b), *Homo sapiens* chromosome 2: position start 176136921-End 176173102, is provided as SEQ ID NO:24 and can also be targeted. This is an exemplary sequence as the primary transcript of miR-10b (pri-miR-10b) is not well defined. Most likely, based on unpublished RNA sequencing data, it starts close to the HoxD antisense RNA2 and ends at the HOXD antisense growth-associated long non-coding RNA, transcript variant 10. SEQ ID NO: 24 can be considered as a single pri-miR-10b transcript, e.g., HOXD cluster antisense RNA 2>pri-miR-10b<HOXD antisense growth-associated long non-coding RNA, transcript variant 10. Additional sgRNAs targeting the sequence of pri-miR-10b (e.g., SEQ ID NO:24) and its promoter could be designed and utilized.

The gene encoding the human miR-10a precursor is at nucleotides 48,579,947-48,579,838 of chromosome 17 (see GenBank Acc. No. NC_000017.11). The sequence of human gene coding for pre-microRNA-10b (MIR10B) (GenBank Acc. No. NR_029609.1) is 110 nucleotides, as follows: GATCTGTCTGTCTTCTGTATATACCCTGTA- GATCCGAATTTGTGTAAGGAATT TTGTGGT-CACAAATTCGTATCTAGGGGAATATGTAGTTGACAT-AAACACTCC GCTCT (SEQ ID NO:25). An exemplary miR-10a primary transcript (pri-miR-10a), *Homo sapiens* chromosome 17: position start 48,548,870 to 48,590,369, provided in SEQ ID NO:26 can also be targeted. This is an exemplary sequence as the primary transcript of miR-10a (pri-miR-10a) is not well defined. Most likely, based on RNA sequencing data, it starts close to the HOXB cluster antisense RNA 3 transcript and ends at the HOXB cluster antisense RNA 1. SEQ ID NO:26 can be considered as a single pri-miR-10a transcript, and additional sgRNAs targeting the sequence of pri-miR-10a and its promoter could be designed and utilized.

Therefore, additional sgRNAs targeting the sequence of pri-miR-10a (e.g., SEQ ID NO:26) and its promoter could be designed and utilized. In some embodiments, sgRNAs targeting sequence that is identical, or at least 80%, 85%, 90%, 95%, or 99% identical between miR-l0a and miR-10b are used, e.g., sgRNAs that target both miR-l0a and miR-10b encoding sequences.

TABLE A miR10b target sequences, genome editing by SpCas9 from *Streptococcus pyogenes* (PAM: 5'-NGG-3')

| sgRNA Target (5' to 3') | SEQ ID NO: | Position | Cleavage Position (%) | Direction | GC Contents (%, w/o PAM) |
|---|---|---|---|---|---|
| ATAGACAACGTTACAACCTCTGG | 2 | 1 | 5.5 | − | 40.0 |
| CACACAAATTCGGTTCTACAGGG | 3 | 29 | 31.2 | − | 40.0 |
| CCTGTAGAACCGAATTTGTGTGG | 4 | 30 | 42.2 | + | 45.0 |
| CCACACAAATTCGGTTCTACAGG | 5 | 30 | 32.1 | − | 45.0 |
| ATACGGATACCACACAAATTCGG | 6 | 39 | 40.4 | − | 35.0 |
| GAATCGAATCTGTGACTATACGG | 7 | 56 | 56.0 | − | 35.0 |
| ATAGTCACAGATTCGATTCTAGG | 8 | 60 | 69.7 | + | 35.0 |
| TAGTCACAGATTCGATTCTAGGG | 9 | 61 | 70.6 | + | 35.0 |
| AGTCACAGATTCGATTCTAGGGG | 10 | 62 | 71.6 | + | 40.0 |
| TTCGATTCTAGGGGAATATATGG | 11 | 71 | 79.8 | + | 35.0 |

TABLE B miR10b target sequences, genome editing by SpCas9 from *Staphylococcus aureus* (PAM: 5'-NNGRRT-'3, (R = A or G)

| sgRNA Target (5' to 3') | SEQ ID NO: | Position | Cleavage Position (%) | Direction | GC Contents (%, w/o PAM) |
|---|---|---|---|---|---|
| TCTATATATACCCTGTAGAACCGAAT | 12 | 19 | 32.1 | + | 30.0 |
| ACCACACAAATTCGGTTCTACAGGGT | 13 | 28 | 33.0 | − | 40.0 |
| AGAATCGAATCTGTGACTATACGGAT | 14 | 54 | 56.9 | − | 35.0 |
| AGTCACAGATTCGATTCTAGGGGAAT | 15 | 62 | 71.6 | + | 40.0 |
| GACCATATATTCCCCTAGAATCGAAT | 16 | 70 | 71.6 | − | 40.0 |
| GCATCGACCATATATTCCCCTAGAAT | 17 | 75 | 76.1 | − | 50.0 |

TABLE C

| miR10b target sequences, genome editing by SpCas9 from *Neisseria meningitides* (PAM: 5'-NNNNGMTT-3' (M = A or C) | | | | | |
|---|---|---|---|---|---|
| sgRNA Target (5' to 3') | SEQ ID NO: | Position | Cleavage Position (%) | Direction | GC Contents (%, w/o PAM) |
| GAATTTGTGTGGTATCCGTATAGTCACAGATT | 18 | 41 | 56.0 | + | 37.5 |
| TGTGTGGTATCCGTATAGTCACAGATTCGATT | 19 | 46 | 60.6 | + | 45.8 |
| TTGTGTGGTATCCGTATAGTCACAGATT | 20 | 45 | 56.0 | + | 40.0 |
| TGGTATCCGTATAGTCACAGATTCGATT | 21 | 50 | 60.6 | + | 45.0 |

Other Cas9s from other species can also be used, including those shown in Table D. Suitable target sequences for use with those Cas9s can readily be determined using known methods.

TABLE D

| Additional Cas9s from various species | |
|---|---|
| Species/Variant of Cas9 | PAM Sequence |
| SpCas9 D1135E variant | NGG (reduced NAG binding) |
| SpCas9 VRER variant | NGCG |
| SpCas9 EQR variant | NGAG |
| SpCas9 VQR variant | NGAN or NGNG |
| *Streptococcus thermophilus* (ST) | NNAGAAW |
| *Treponema denticola* (TD) | NAAAAC |
| *Streptococcus pyogenes* (SP); SpCas9 | NGG |
| *Staphylococcus aureus* (SA); SaCas9 | NNGRRT or NNGRR(N) |
| *Neisseria meningitidis* (NM) | NNNNGATT |

Cas9 Editing Enzymes

The methods include the delivery of Cas9 editing enzymes to the cancer cells. The editing enzymes can include one or more of SpCas9 D1135E variant; SpCas9 VRER variant; SpCas9 EQR variant; SpCas9 VQR variant; *Streptococcus thermophilus* (ST) Cas9 (StCas9); *Treponema denticola* (TD) (TdCas9); *Streptococcus pyogenes* (SP) (SpCas9); *Staphylococcus aureus* (SA) Cas9 (SaCas9); or *Neisseria meningitidis* (NM) Cas9 (NmCas9), as well as variants thereof that are at least 80%, 85%, 90%, 95%, 99% or 100% identical thereto that retain at least one function of the parent case, e.g., the ability to complex with a gRNA, bind to target DNA specified by the gRNA, and alter the sequence of the target DNA.

To determine the percent identity of two sequences, the sequences are aligned for optimal comparison purposes (gaps are introduced in one or both of a first and a second amino acid or nucleic acid sequence as required for optimal alignment, and non-homologous sequences can be disregarded for comparison purposes). The length of a reference sequence aligned for comparison purposes is at least 80% (in some embodiments, about 85%, 90%, 95%, or 100% of the length of the reference sequence) is aligned. The nucleotides or residues at corresponding positions are then compared. When a position in the first sequence is occupied by the same nucleotide or residue as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. For example, the percent identity between two amino acid sequences can be determined using the Needleman and Wunsch ((1970) J. Mol. Biol. 48:444-453) algorithm which has been incorporated into the GAP program in the GCG software package, using a Blossum 62 scoring matrix with a gap penalty of 12, a gap extend penalty of 4, and a frameshift gap penalty of 5.

The PAM sequences of these Cas9s are listed in Table D, above. The sequences of the Cas9s are known in the art; see, e.g., Kleinstiver et al., Nature. 2015 Jul. 23; 523(7561): 481-485; WO 2016/141224; U.S. Pat. No. 9,512,446; US-2014-0295557; WO 2014/204578; and WO 2014/144761. The methods can also include the use of the other previously described variants of the SpCas9 platform (e.g., truncated sgRNAs (Tsai et al., Nat Biotechnol 33, 187-197 (2015); Fu et al., Nat Biotechnol 32, 279-284 (2014)), nickase mutations (Mali et al., Nat Biotechnol 31, 833-838 (2013); Ran et al., Cell 154, 1380-1389 (2013)), FokI-dCas9 fusions (Guilinger et al., Nat Biotechnol 32, 577-582 (2014); Tsai et al., Nat Biotechnol 32, 569-576 (2014); WO2014144288).

The SpCas9 wild type sequence is as follows:

(SEQ ID NO: 22)

MDKKYSIGLDIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKERGHFLIEGDLNPDNSDVDKLFIQLVQTYNQLFEENP

INASGVDAKAILSARLSKSRRLENLIAQLPGEKKNGLFGNLIALSLGLTP

NEKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECEDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

-continued

```
MGRHKPENIVIEMARENQTTQKGQKNSRERMKRIEEGIKELGSQILKEHP

VENTQLQNEKLYLYYLQNGRDMYVDQELDINRLSDYDVDHIVPQSFLKDD

SIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLI

REVKVITLKSKLVSDFRKDFQFYKVREINNYHHAHDAYLNAVVGTALIKK

YPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEV

QTGGFSKESILPKRNSDKLIARKKDWDPKKYGGFDSPTVAYSVLVVAKVE

KGKSKKLKSVKELLGITIMERSSFEKNPIDFLEAKGYKEVKKDLIIKLPK

YSLFELENGRKRMLASAGELQKGNELALPSKYVNFLYLASHYEKLKGSPE

DNEQKQLFVEQHKHYLDEIIEQISEFSKRVILADANLDKVLSAYNKHRDK

PIREQAENIIHLFTLTNLGAPAAFKYFDTTIDRKRYTSTKEVLDATLIHQ

SITGLYETRIDLSQLGGD
```

The SaCas9 wild type sequence is as follows:

```
                                            (SEQ ID NO: 23)
MKRNYILGLDIGITSVGYGIIDYETRDVIDAGVRLFKEANVENNEGRRSK

RGARRLKRRRRHRIQRVKKLLFDYNLLTDHSELSGINPYEARVKGLSQKL

SEEEFSAALLHLAKRRGVHNVNEVEEDTGNELSTKEQISRNSKALEEKYV

AELQLERLKKDGEVRGSINRFKTSDYVKEAKQLLKVQKAYHQLDQSFIDT

YIDLLETRRTYYEGPGEGSPFGWKDIKEWYEMLMGHCTYFFEELRSVKYA

YNADLYNALNDLNNLVITRDENEKLEYYEKFQIIENVFKQKKKPTLKQIA

KEILVNEEDIKGYRVTSTGKPEFTNLKVYHDIKDITARKEIIENAELLDQ

IAKILTIYQSSEDIQEELTNLNSELTQEEIEQISNLKGYTGTHNLSLKAI

NLILDELWHTNDNQIAIFNRLKLVPKKVDLSQQKEIPTTLVDDFILSPVV

KRSFIQSIKVINAIIKKYGLPNDIIIELAREKNSKDAQKMINEMQKRNRQ

TNERIEEIIRTTGKENAKYLIEKIKLHDMQEGKCLYSLEAIPLEDLLNNP

FNYEVDHIIPRSVSFDNSFNNKVLVKQEENSKKGNRTPFQYLSSSDSKIS

YETFKKHILNLAKGKGRISKTKKEYLLEERDINRFSVQKDFINRNLVDTR

YATRGLMNLLRSYFRVNNLDVKVKSINGGFTSFLRRKWKFKKERNKGYKH

HAEDALIIANADFIFKEWKKLDKAKKVMENQMFEEKQAESMPEIETEQEY

KEIFITPHQIKHIKDFKDYKYSHRVDKKPNRELINDTLYSTRKDDKGNTL

IVNNLNGLYDKDNDKLKKLINKSPEKLLMYHHDPQTYQKLKLIMEQYGDE

KNPLYKYYEETGNYLTKYSKKDNGPVIKKIKYYGNKLNAHLDITDDYPNS

RNKVVKLSLKPYRFDVYLDNGVYKFVTVKNLDVIKKENYYEVNSKCYEEA

KKLKKISNQAEFIASFYNNDLIKINGELYRVIGVNNDLLNRIEVNMIDIT

YREYLENMNDKRPPRIIKTIASKTQSIKKYSTDILGNLYEVKSKKHPQII

KKG
```

See also Hou, Z. et al. Efficient genome engineering in human pluripotent stem cells using Cas9 from *Neisseria meningitidis.* Proc Natl Acad Sci USA (2013); Fonfara, I. et al. Phylogeny of Cas9 determines functional exchangeability of dual-RNA and Cas9 among orthologous type II CRISPR-Cas systems. Nucleic Acids Res 42, 2577-2590 (2014); Esvelt, K. M. et al. Orthogonal Cas9 proteins for RNA-guided gene regulation and editing. Nat Methods 10, 1116-1121 (2013); Cong, L. et al. Multiplex genome engineering using CRISPR/Cas systems. Science 339, 819-823 (2013); Horvath, P. et al. Diversity, activity, and evolution of CRISPR loci in *Streptococcus thermophilus.* J Bacteriol 190, 1401-1412 (2008).

As noted above, the Cas9 can be delivered as a purified protein (e.g., a recombinantly produced purified protein, prefolded and optionally complexed with the sgRNA) or as a nucleic acid encoding the Cas9, e.g., an expression construct. Purified Cas9 proteins can be produced using methods known in the art, e.g., expressed in prokaryotic or eukaryotic cells and purified using standard methodology. See, e.g., Liang et al., Journal of Biotechnology 208:44-53 (2015); Kim et al., Genome Res. 2014 June; 24(6): 1012-1019. Efficiency of protein delivery can be enhanced, e.g., using electroporation (see, e.g., Wang et al., Journal of Genetics and Genomics 43(5):319-327 (2016)); cationic or lipophilic carriers (see, e.g., Yu et al., Biotechnol Lett. 2016; 38: 919-929; Zuris et al., Nat Biotechnol. 33(1):73-80 (2015)); or even lentiviral packaging particles (see, e.g., Choi et al., Gene Therapy 23, 627-633 (2016)).

Expression Constructs

Expression constructs encoding one or both of guide RNAs and/or Cas9 editing enzymes can be administered in any effective carrier, e.g., any formulation or composition capable of effectively delivering the component gene to cells in vivo. Approaches include insertion of the gene in viral vectors, including recombinant retroviruses, adenovirus, adeno-associated virus, lentivirus, and herpes simplex virus-1, or recombinant bacterial or eukaryotic plasmids. Viral vectors transfect cells directly; plasmid DNA can be delivered naked or with the help of, for example, cationic liposomes (lipofectamine) or derivatized (e.g., antibody conjugated), polylysine conjugates, gramacidin S, artificial viral envelopes or other such intracellular carriers, as well as direct injection of the gene construct or $CaPO_4$ precipitation carried out in vivo.

A preferred approach for in vivo introduction of nucleic acid into a cell is by use of a viral vector containing nucleic acid, e.g., a cDNA. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells that have taken up viral vector nucleic acid.

Retrovirus vectors and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, *Blood* 76:271 (1990)). A replication defective retrovirus can be packaged into virions, which can be used to infect a target cell through the use of a helper virus by standard techniques. Protocols for producing recombinant retroviruses and for infecting cells in vitro or in vivo with such viruses can be found in Ausubel, et al., eds., *Current Protocols in Molecular Biology,* Greene Publishing Associates, (1989), Sections 9.10-9.14, and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include ΨCrip, ΨCre, Ψ2 and ΨAm. Retroviruses have been used to introduce a variety of genes into many different cell types, including epithelial cells, in vitro and/or in vivo (see for example Eglitis, et al. (1985) Science 230:1395-1398; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad. Sci. USA 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J. Immunol. 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

As demonstrated herein, a lentiviral CRISPR-Cas9 targeting system provided high and tumor-specific expression of Cas9, the corresponding high miR-10a/10b editing efficacy in tumor tissues, while lacking general toxicity or neurotoxicity. Lentiviral vectors transduce dividing as well as quiescent cells. This can be viewed as a major advantage with respect to gene therapy for tumors in general, as within a short treatment window most tumor cells (and especially GSC) do not divide. Therapeutic use of the lentiviral editing approach can be a legitimate alternative to other viral systems, as high viral titers can be produced, nonproliferating cells that are especially abundant in the walls of the tumor cavity after surgery can be transduced, and transduction efficacies are very high. An additional advantage of a locally applied vesicular stomatitis virus glycoprotein (VSV-G) pseudotyped lentivirus is its inactivation by human serum that would reduce systemic effects. To further reduce neurotrophism, and enhance selective tropism for glioma and GSC, the commonly bound envelope glycoprotein of VSV can be replaced with a more selective variant glycoprotein of lymphocytic choriomeningitis virus (LCMV-GP). LCMV-GP is not cytotoxic when injected locally or systemically, can be packaged with other components of the CRISPR-Cas9 system, and efficiently transduces solid glioma tissues as well as infiltrating tumor cells.

Another viral gene delivery system useful in the present methods utilizes adenovirus-derived vectors. The genome of an adenovirus can be manipulated, such that it encodes and expresses a gene product of interest but is inactivated in terms of its ability to replicate in a normal lytic viral life cycle. See, for example, Berkner et al., BioTechniques 6:616 (1988); Rosenfeld et al., Science 252:431-434 (1991); and Rosenfeld et al., Cell 68:143-155 (1992). Suitable adenoviral vectors derived from the adenovirus strain Ad type 5 dl324 or other strains of adenovirus (e.g., Ad2, Ad3, or Ad7 etc.) are known to those skilled in the art. Recombinant adenoviruses can be advantageous in certain circumstances, in that they are not capable of infecting non-dividing cells and can be used to infect a wide variety of cell types, including epithelial cells (Rosenfeld et al., (1992) supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ, where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham, J. Virol. 57:267 (1986).

miR-10a/10b genome-editing vectors based on recombinant Adenovirus-5 (Ad5): Ad5 have many advantages for this purpose, including non-integration, lack of insertional mutagenesis, high-efficiency transduction, and accommodation of large expression cassettes; these vectors have also been utilized in multiple clinical trials. In some embodiments, an Ad5-CRISPR/Cas9nD10A-10b (or 10a) vector expressing a pair of G1 and G3 sgRNAs under the control of a U6 promoter and containing the expression system for CRISPR/Cas9nD10A can be used. Other combinations of CRISPR/Cas9 systems (enzymes and corresponding sgRNAs) could be utilized based on Ad5; for example, the vectors can be replication-defective, wherein E1A and E1B genes are replaced by an expression cassette. In addition to E1A, E1B, the vectors can be deleted for E3 and E4, to avoid leaky expression of other early as well as late adenoviral genes, thus avoiding an inflammatory response. These vectors can be produced in complementing cell lines that express E1A, E1B, and E4 proteins.

Helper-dependent (HDAd) vectors can also be produced with all adenoviral sequences deleted except the origin of DNA replication at each end of the viral DNA along with packaging signal at 5-prime end of the genome downstream of the left packaging signal. HDAd vectors are constructed and propagated in the presence of a replication-competent helper adenovirus that provides the required early and late proteins necessary for replication.

Yet another viral vector system useful for delivery of nucleic acids is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al., Curr. Topics in Micro. and Immunol. 158:97-129 (1992). It is also one of the few viruses that may integrate its DNA into non-dividing cells, and exhibits a high frequency of stable integration (see for example Flotte et al., Am. J. Respir. Cell. Mol. Biol. 7:349-356 (1992); Samulski et al., J. Virol. 63:3822-3828 (1989); and McLaughlin et al., J. Virol. 62:1963-1973 (1989). Vectors containing as little as 300 base pairs of AAV can be packaged and can integrate. Space for exogenous DNA is limited to about 4.5 kb. An AAV vector such as that described in Tratschin et al., Mol. Cell. Biol. 5:3251-3260 (1985) can be used to introduce DNA into cells. A variety of nucleic acids have been introduced into different cell types using AAV vectors (see for example Hermonat et al., Proc. Natl. Acad. Sci. USA 81:6466-6470 (1984); Tratschin et al., Mol. Cell. Biol. 4:2072-2081 (1985); Wondisford et al., Mol. Endocrinol. 2:32-39 (1988); Tratschin et al., J. Virol. 51:611-619 (1984); and Flotte et al., J. Biol. Chem. 268:3781-3790 (1993). The identification of *Staphylococcus aureus* (SaCas9) and other smaller Cas9 enzymes that can be packaged into adeno-associated viral (AAV) vectors that are highly stable and effective in vivo, easily produced, approved by FDA, and tested in multiple clinical trials, paves new avenues for therapeutic gene editing. Of high relevance to gliomas like GBM, better tissue distribution of AAV provides an additional advantage for invasive and recurrent tumors. miR-10b-targeting AAV vectors of various serotypes, including AAV1, AAV2, AAV8, AAV9, and AAVrh.10, can be used, all of which were previously tested in clinical trials. A miR-10a/10b targeting AAV plasmid [based on Addgene Plasmids #61592, #61594], a single vector expressing SaCas9, gRNA, and Ampicillin selection marker can be utilized. Since PAM consensus sequence is different between SpCas9 and SaCas9 (the late cleaves genomic targets most efficiently with NNGRRT or NNGRR (R=A or G), as also the length required for SaCas9 gRNAs (21-23 nt), several targeting constructs have been designed.

In some embodiments, nucleic acids encoding a CRISPR miR-10b gene editing complex (e.g., Cas9 or gRNA) are entrapped in liposomes bearing positive charges on their surface (e.g., lipofectins), which can be tagged with antibodies against cell surface antigens of the target glioblastoma cells, e.g., CD133, CD15, CD44, CXCR4, and/or integrin alpha 6 (see, e.g., Friedman et al., "Pediatric glioma stem cells: biologic strategies for oncolytic HSV virotherapy," Front. Oncol. 3:28 (2013); Mizuno et al., No Shinkei Geka 20:547-551 (1992); PCT publication WO91/06309; Japanese patent application 1047381; and European patent publication EP-A-43075). These delivery vehicles can also be used to deliver Cas9 protein/gRNA complexes.

In clinical settings, the gene delivery systems for the nucleic acids encoding a CRISPR miR-10b gene editing complex can be introduced into a subject by any of a number of methods, each of which is familiar in the art. For instance, a pharmaceutical preparation of the gene delivery system can be introduced systemically, e.g., by intravenous injection, and specific transduction of the protein in the target cells will occur predominantly from specificity of transfection, provided by the gene delivery vehicle, cell-type or tissue-type expression due to the transcriptional regulatory sequences controlling expression of the receptor gene, or a combination thereof. In other embodiments, initial delivery of the nucleic acids encoding a CRISPR miR-10a/10b gene editing complex is more limited, with introduction into the subject being quite localized. For example, the nucleic acids encoding a CRISPR miR-10a/10b gene editing complex can be introduced by catheter (see U.S. Pat. No. 5,328,470) or by stereotactic injection (e.g., Chen et al., PNAS USA 91: 3054-3057 (1994)). In some embodiments, the nucleic acids encoding a CRISPR miR-10a/10b gene editing complex are administered during or after surgical resection of a tumor; in some embodiments, a controlled-release hydrogel comprising the nucleic acids encoding a CRISPR miR-10a/10b gene editing complex is administered at the conclusion of resection before closure to provide a steady dose of the nucleic acids encoding a CRISPR miR-10a/10b gene editing complex over time.

A pharmaceutical preparation of the nucleic acids encoding a CRISPR miR-10a/10b gene editing complex can consist essentially of the gene delivery system (e.g., viral vector(s)) in an acceptable diluent, or can comprise a slow release matrix in which the gene delivery vehicle is embedded. Alternatively, where the complete gene delivery system can be produced intact from recombinant cells, e.g., retroviral vectors, the pharmaceutical preparation can comprise one or more cells, which produce the gene delivery system.

Preferably, the CRISPR miR-10a/10b editing complex is specific, i.e., induces genomic alterations preferentially at the target site (miR-10a/10b), and does not induce alterations at other sites, or only rarely induces alterations at other sites.

Pharmaceutical Compositions and Methods of Administration

The methods described herein include the use of pharmaceutical compositions comprising CRISPR miR-10a/10b editing complexes as an active ingredient.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions, e.g., chemotherapeutic agents.

Pharmaceutical compositions are typically formulated to be compatible with its intended route of administration. Examples of routes of administration to the brain include parenteral, e.g., intravenous, intrathecal, intratumoral injection, or intranasal (e.g., inhalation). In some embodiments, the compositions are administered during or after surgical resection of a tumor, to the surgical site.

Methods of formulating suitable pharmaceutical compositions are known in the art, see, e.g., *Remington: The Science and Practice of Pharmacy,* 21st ed., 2005; and the books in the series Drugs and the *Pharmaceutical Sciences: a Series of Textbooks and Monographs* (Dekker, NY). For example, solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, NJ) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Therapeutic compounds that are or include nucleic acids can be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al., Clin. Immunol. Immunopathol., 88(2), 205-10 (1998). Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as collagen, ethylene vinyl acetate, polyanhydrides (e.g., poly[1,3-bis(carboxyphenoxy)propane-co-sebacic-acid] (PCPP-SA) matrix, fatty acid dimer-sebacic acid (FAD-SA) copolymer, poly(lactide-co-glycolide)), polyglycolic acid, collagen, polyorthoesters, polyethyleneglycol-coated liposomes, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811. Semisolid, gelling, soft-gel, or other formulations (including controlled release) can be used, e.g., when administration to a surgical site is desired. Methods of making such formulations are known in the art and can include the use of biodegradable, biocompatible polymers. See, e.g., Sawyer et al., Yale J Biol Med. 2006 December; 79(3-4): 141-152;

The pharmaceutical compositions can be included in a container, pack, or dispenser together with instructions for administration.

EXAMPLES

The invention is further described in the following examples, which do not limit the scope of the invention described in the claims.

Materials & Methods

The following materials and methods were used in the Examples set forth herein.

CRISPR-CAS9 plasmid construction and lentivirus production. sgRNA guide sequences were designed and cloned into plasmids PX330, PX335, and lentiCRISPR v2 (a gift from Feng Zhang, Addgene plasmids #42230, #42335, #52961), based on (20, 32). LentiCRISPR v2 plasmid was used as a template for site-directed mutagenesis by inverse PCR to generate LentiCRISPR V2 nCas9 (D10A mutant Cas9, A changed to C at the position 146 from the ATG). The sequences used for miRNA targeting are listed in Table 2. For lentivirus production, the lentiCRISPR v2 plasmids were co-transfected with packaging psPAX2 plasmids and VSV-G envelope expressing plasmid (Addgene plasmids #12259 and #12260) as described (20), and viruses concentrated by additional ultracentrifugation at 25,000 rpm. Lentivirus functional titer was determined by serial dilution in LN229 cells using immunofluorescence for Cas9 with Novusbio 7A9-3A3 antibody. Positive cells were counted and the titer estimated using the following formula: Titer (TU/ml)=number of transduced cells in day 1× percent of fluorescent-positive cells×1,000/volume of lentivirus used (μl).

TABLE 2

A list of sgRNAs and PCR primers.

| sgRNA guides | Sequence 5' to 3' | SEQ ID NO: |
|---|---|---|
| miR-10b-G1 sgRNA | CCTGTAGAACCGAATTTGTG | 27 |
| miR-10b-G2 sgRNA | CACACAAATTCGGTTCTACA | 28 |
| miR-10b-G3 sgRNA | ATAGACAACGTTACAACCTC | 29 |
| miR-21 sgRNA | TCATGGCAACACCAGTCGA | 30 |
| miR-107 sgRNA | GAGTTCAAGCAGCATTGTAC | 31 |
| miR-139 sgRNA | GTGTCTCCAGTGTGGCTCGG | 32 |

| PCR primers | Sequence 5' to 3' | SEQ ID NO: |
|---|---|---|
| miR-10b-F | GACCCTGGCAGAAGAATGAG | 33 |
| miR-10b-R | TGAGGAGCTTCTGGAGAGGA | 34 |
| miR-10a-F | GCGCGGAAAGTAGGAGAACT | 35 |
| miR-10a-R | CTAACCATGGGTCCGAGACG | 36 |
| miR-21-F | GGTTCGATCTTAACAGGCCAG | 37 |
| miR-21-R | GAGATGAACCACGACTAGAGG | 38 |
| miR-107-F | TTACAGTGTTGCCTTGTGGC | 39 |
| miR-107-R | GAATCTTGCAATGCTTCAAAAC | 40 |
| miR-139-F | CACCTCTACAGTGCACGTGTCTC | 41 |
| miR-139-R | CTCCGAGCCACACTGGAGACACG | 42 |
| NTAN1-F | CCTGTAGACCAAAATTTGTGGAG | 43 |
| NTAN1-R | CCTGTAGACCAAAATTTGTGGAG | 44 |
| 5NTC-F | CTACAGAAATTCTGTTCTACTGG | 45 |
| 5NTC-R | CTACAGAAATTCTGTTCTACTGG | 46 |
| FLRT2-F | AAAGACCATGTTACAACCTCAGG | 47 |
| FLRT2-R | AAAGACCATGTTACAACCTCAGG | 48 |
| ST1A3-F | CCTGAAGATCCGTATTTGTGAAG | 49 |
| ST1A3-R | CCTGAAGATCCGTATTTGTGAAG | 50 |
| PLCH-1-F | CATAAAGGGCAGCATGAGC | 51 |
| PLCH-1-R | TGCCAGCATGCAAATTCTAC | 52 |
| COL3A1-F | ATATACAACATTACTACCTCCAG | 53 |
| COL3A1-R | ATATACAACATTACTACCTCCAG | 54 |
| HoxD4-F | TGGTCT ACC CCT GGA TGA AG | 55 |
| HoxD4-R | AGATGAGGACGATGACCTGC | 56 |
| HoxD3-F | CAGCCTCCTGGTCTGAACTC | 57 |
| HoxD3-R | ATCCAGGGGAAGATCTGCTT | 58 |
| P21-F | TCC TCA TCC CGT GTT CTC CTT | 59 |
| P21-R | AGG AGG AAG TAG CTG GCA TGA A | 60 |
| P16-F | GCC CAA CGC ACC GAA TAG | 61 |
| P16-R | CGC TGC CCA TCA TCA TGA | 62 |

TABLE 2-continued

| A list of sgRNAs and PCR primers. | | |
|---|---|---|
| BIM-F | CAGTTTCCCTGGCTTACTTGTGTT | 63 |
| BIM-R | GTATTGCACAAG TAA AGTGGC AAT TAC | 64 |
| PTBP2-F | CAGTTGGCGTGAAGAGAGGA | 65 |
| PTBP2-R | AGTACACGAGAAGGAGCACC | 66 |
| DGCR14-F | AGCCGAGGAGAATGGAGACT | 67 |
| DGCR14-R | TTCTCCTCCTCCTCTCCAGC | 68 |
| SERAC1-F | ACTGCGGAATCCATTTGCTG | 69 |
| SERAC1-R | AGCAATCAAGAGCCAGCTGA | 70 |
| GAPDH-F | ATGTTCGTCATGGGTGTGAA | 71 |
| GAPDH-R | TGTGGTCATGAGTCCTTCCA | 72 |
| Cas9 D10A-F | GCATCGGCCTGGCCATCGGCACCAAC | 73 |
| Cas9 D10A-R | GTTGGTGCCGATGGCCAGGCCGATGC | 74 |

Surveyor assay for genome editing. Genomic regions surrounding the CRISPR/Cas9 target sites were amplified using Q5 polymerase (NEB) and SURVEYOR nuclease assay was performed as described (32). Efficiency of editing was estimated based on relative band intensities as % gene modification: Indels $\%=100\times(1-(1-\text{fraction cleaved})^{1/2})$. PCR primers used for genomic amplification are listed in Table 2.

Cell cultures and transfections. Human glioma LN229, U251, A172 and breast cancer MCF7 and MDA-MB-231 cell lines were maintained as described (4). Patient-derived low-passage GBM8 cells growing as neurospheres were maintained in Neurobasal medium as previously described (33). HBMEC were cultured in human endothelial culture medium with Complete Growth Medium supplement kit (Cell Biologics). Primary mouse and human astrocytes were maintained in DMEM-F12 supplemented with 10% FBS. Primary mouse neurons were maintained in Neurobasal supplemented with B27 (Invitrogen). The cells were seeded in 24-well plates at 60% confluence and transfected next day with 800 ng of plasmids, with/without 20 nM of oligo mimics (Ambion), using the NeuroMag transfection protocol, according to the manufacturer's instructions (OZ Bioscience). RNA isolation, qRT-PCR, and protein analysis by western blotting were performed as previously described (34). Cell viability has been assessed using WST1 (Roche), according to the manufacturer's instructions, 2 days post-transfection for the monolayer cultures, and 5 days post-transfection for neurospheres. Wound healing assay was performed as described (35).

Transformation assay. Primary P1 mouse astrocytes plated at 10% density in 25 $cm^2$ flasks were transfected with 10 μg of RasG12V/Ad-E1 plasmids or infected by SV40 large T antigen lentivirus, and 24 h later infected by Lentivirus expressing CRISPR-Cas9. Total RNA was extracted and supplemental cultures plates were fixed with 4% formaldehyde and stained with crystal violet two weeks post-transformation.

Stereotaxic injections of tumor cells, whole body imaging (WBI), and lentivirus injection. LN229 and GBM8 cells ($10^5$) expressing firefly luciferase and mCherry were stereotactically implanted into the striatal area (coordinates: P-A 0.5; C-L 1.7; D-V 2.3 mm) of 8 weeks old athymic nu/nu mice (Jackson Laboratory) and the growth of intracranial tumors was monitored by Fluc bioluminescence imaging (34). When bioluminescence reached the exponential phase with signal of $10^6$ photons/sec (10 days after LN229 and 19 days after GBM8 implantation), the lentival CRISPR-Cas9 constructs ($3\times10^5$ TU) were injected intratumorally to the same coordinates. The animals were randomized to the "treatment" and "control" groups based on the WBI, with similar average bioluminescence signal and tumor growth rates per group. All animal studies have been approved and performed in accordance with Harvard Medical Area Standing Committee guidelines.

Immunohistochemistry and H&E staining. Intracranial tumors were fixed with 4% formaldehyde, embedded, and cryo-sectioned. Staining of 20 μm-thick sections was performed using Cas9 antibody (7A9-3A3, Novus Biologicals), DAPI, and Hematoxylin & Eosin as described (34).

Statistical analysis. The unpaired, two-tailed Student's t-test was used for comparison between two groups and unpaired ANOVA test for comparison of three groups. All values were presented as mean±SEM. The adequate sample sizes were calculated based on Resource equation method (36).

Example 1.1

The Design of RNA Guides (sgRNA) and Validation of miR-10b Targeting

We utilized the Type II CRISPR-Cas9 system derived from *Streptococcus pyogenes* that induces site-directed double strand breaks in DNA, leading to disruption or mutation of a targeted site through non-homologous end joining (reviewed in 16). The system requires the Protospacer Adjacent Motif (PAM) sequence of 5'-NGG-3', located at the immediate 3' end of the sgRNA recognition sequence (17). Alternative sequence-specific sgRNAs (G1-G3) targeting either mature human miR-10b or its precursor pre-miR-10b and thereby disrupting the pre-miR-10b structure and processing were designed using the CRISPRtool (crispr.mit.edu) and selected to minimize potential off-target effects (FIG. 1A). The CRISPR-Cas9 system was used with G1-G3 sgRNAs for mutating miR-10b in tumorigenic glioma LN229 cells. We also utilized a mutated "nickase" version of the Cas9 enzyme (Cas9n D10A) that, guided by a pair of adjacent, opposite strand sgRNAs G1 and G3 (nG1/G3), produces double nicks that can be repaired by NHEJ and potentially introduces indels. Double nicking has a potential to reduce unwanted off-target effects greatly (18). Using magnetofection (NeuroMag Bioscience), we achieved plasmid transfection efficiency of 60% in glioma cells. Surveyor cleavage assay indicated that the sgRNAs tested produced 8-36% editing efficiencies at the miR-10b locus (FIG. 1B, left panel), resulting in the measurable down-regulation of mature miR-10b expression (FIG. 1B, right panel). sgRNA G1 and G3-guided editing that was more efficient than that of G2 also led to the more efficient miR-10b reduction.

Figure 1B:
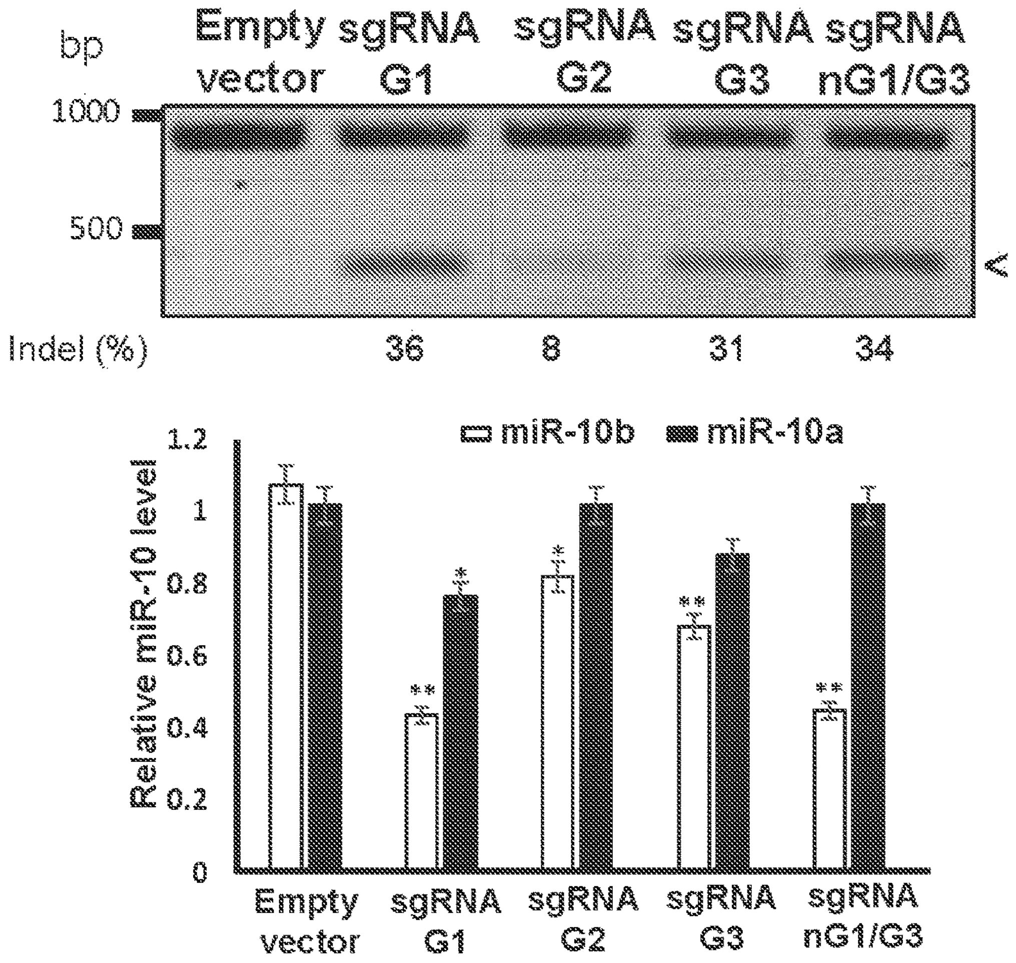
Figure 1C:
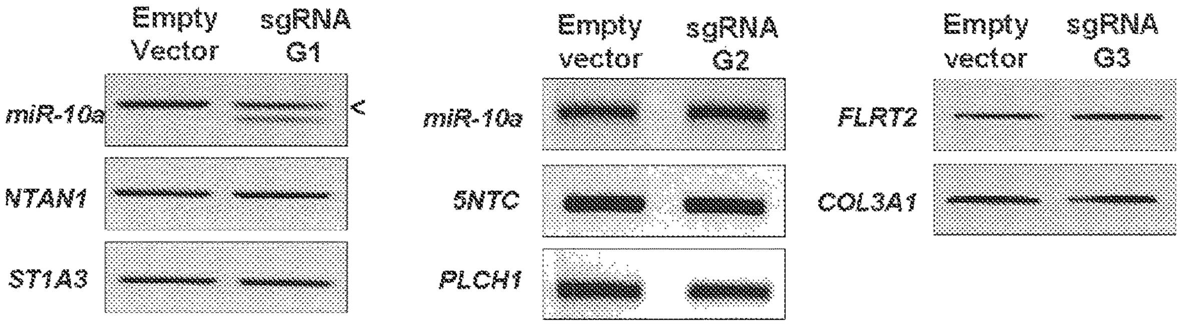

As off-target effects of the Cas9 activity represent the major concern for the use of the CRISPR-Cas9 system, we assessed potential off-targets for G1-G3 sgRNAs by employing several computational algorithms. miR-10a, the most closely related miR-10 family member that differs from miR-10b by a single nucleotide, represents the top off-target for both G1 and G2-directed targeting (FIGS. 1A, C). As expected, despite the strong similarity between the mature miR-10a and miR-10b, miR-10a locus was not targeted by CRISPR-Cas9 with G3 sgRNA that was designed for less similar pre-miR-10b precursor (FIG. 1B). Additional predicted top protein-coding off-targets were not edited (FIG. 1C). Also, expression of the adjacent HOXD3 and HOXD4 genes was unaffected by CRISPR-Cas9 with G1-G3 sgRNAs (FIG. 6).

Example 1.2 miR-10b Expression is Essential for Viability of Glioma Cells

Figure 2C:
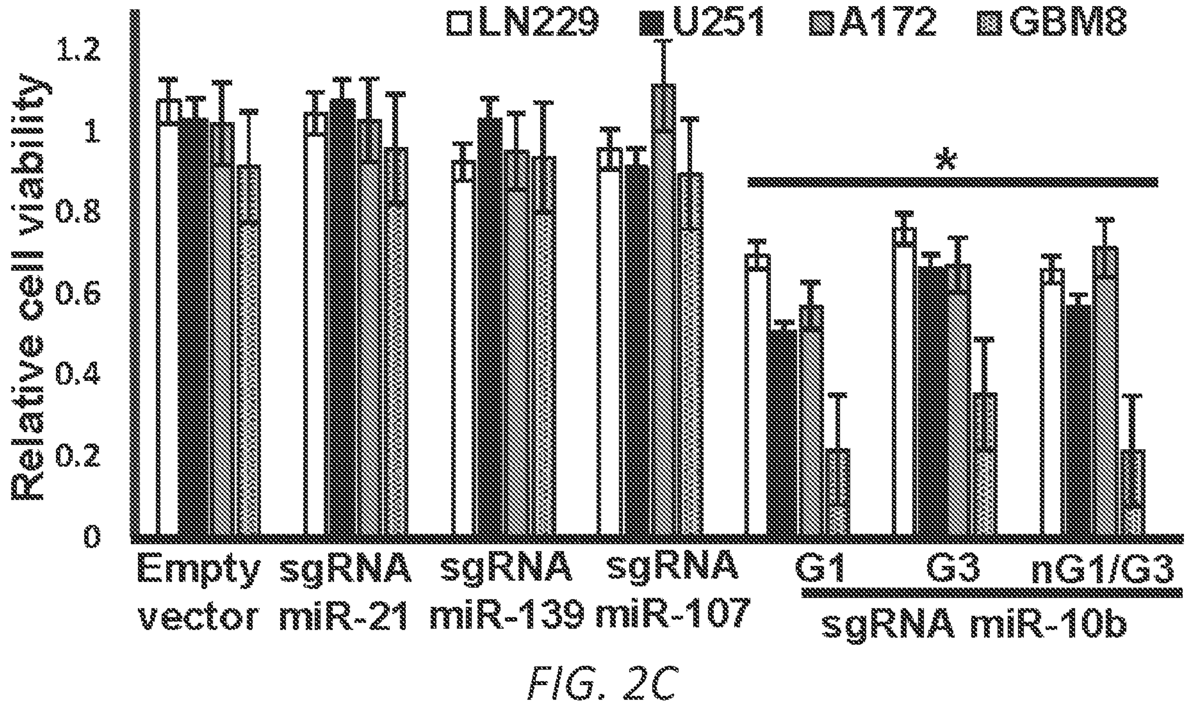
Figure 2D:
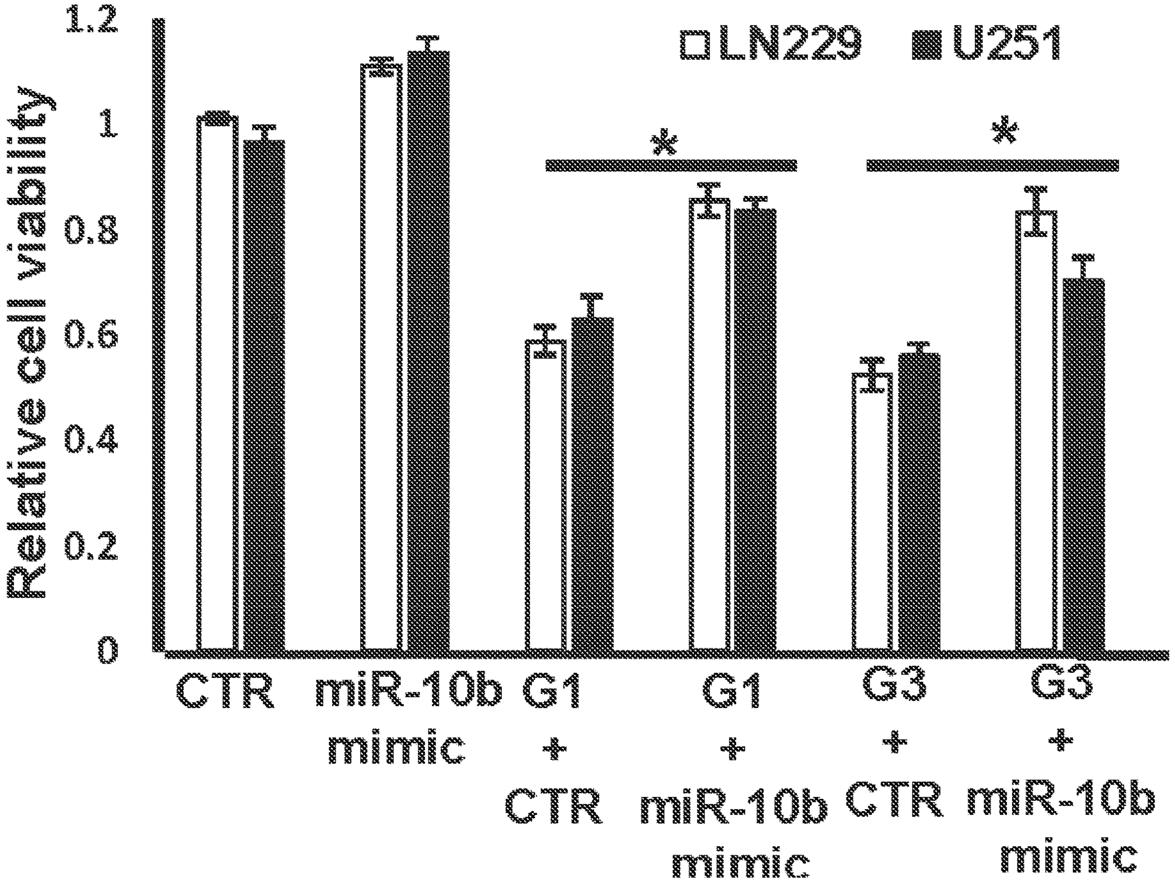
Figure 2E:
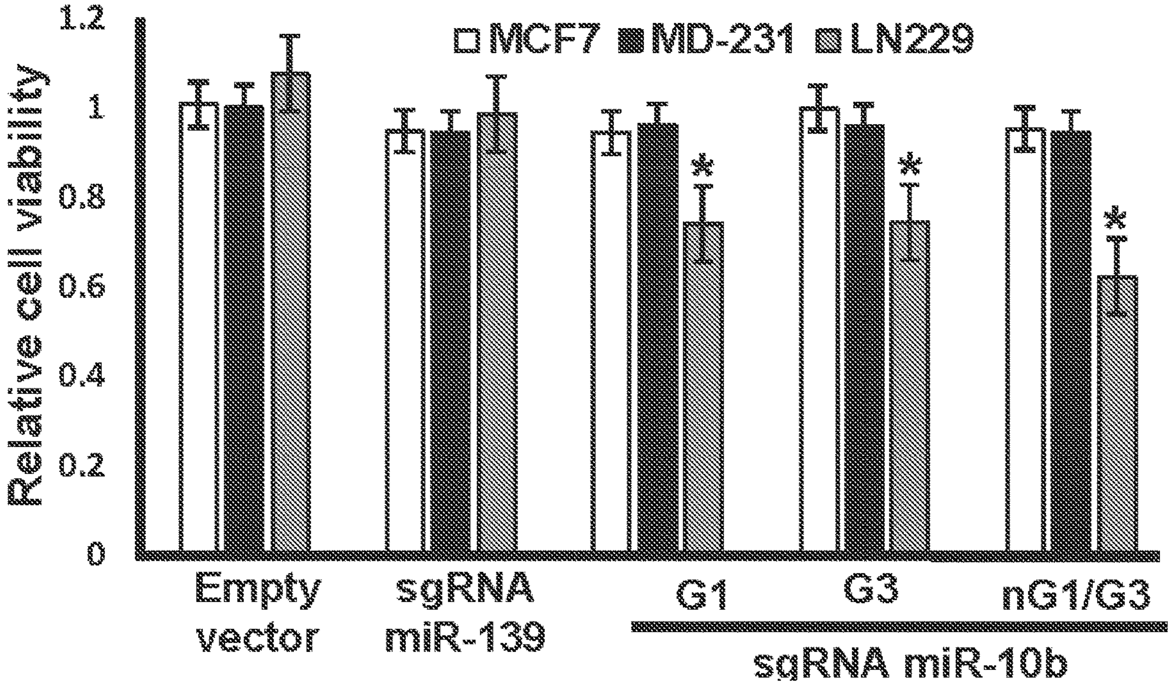
Figure 2F:
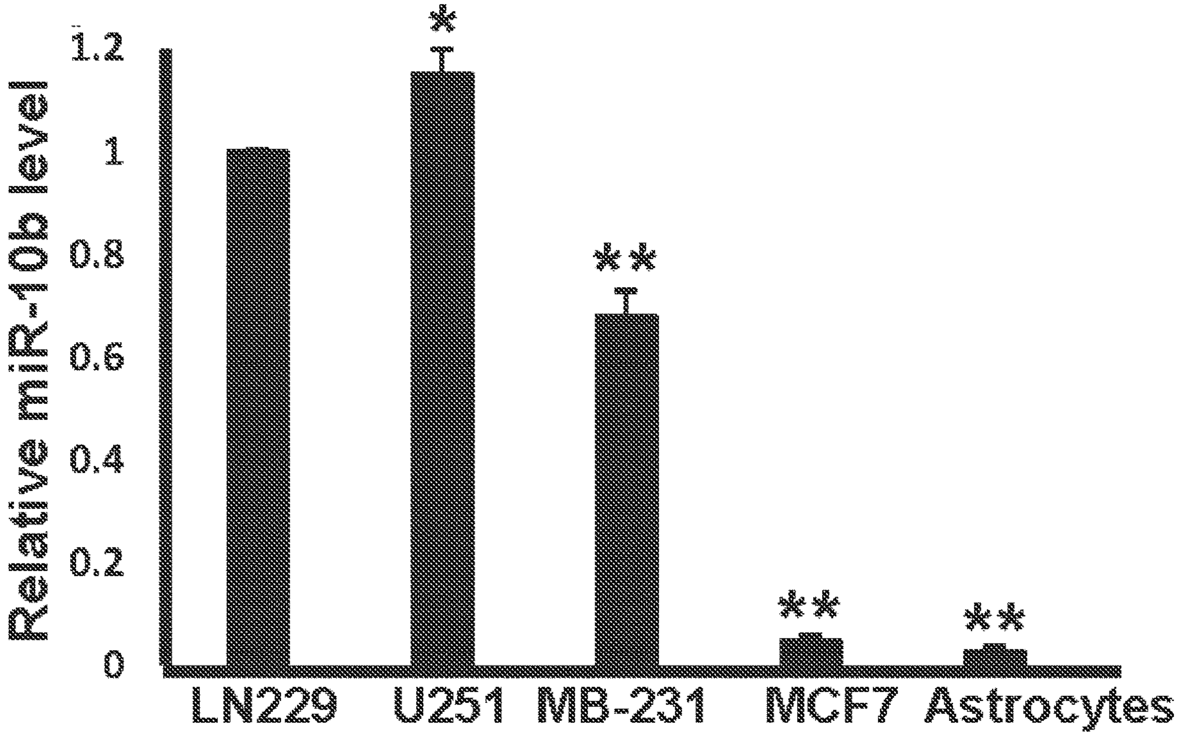
Figure 2G:
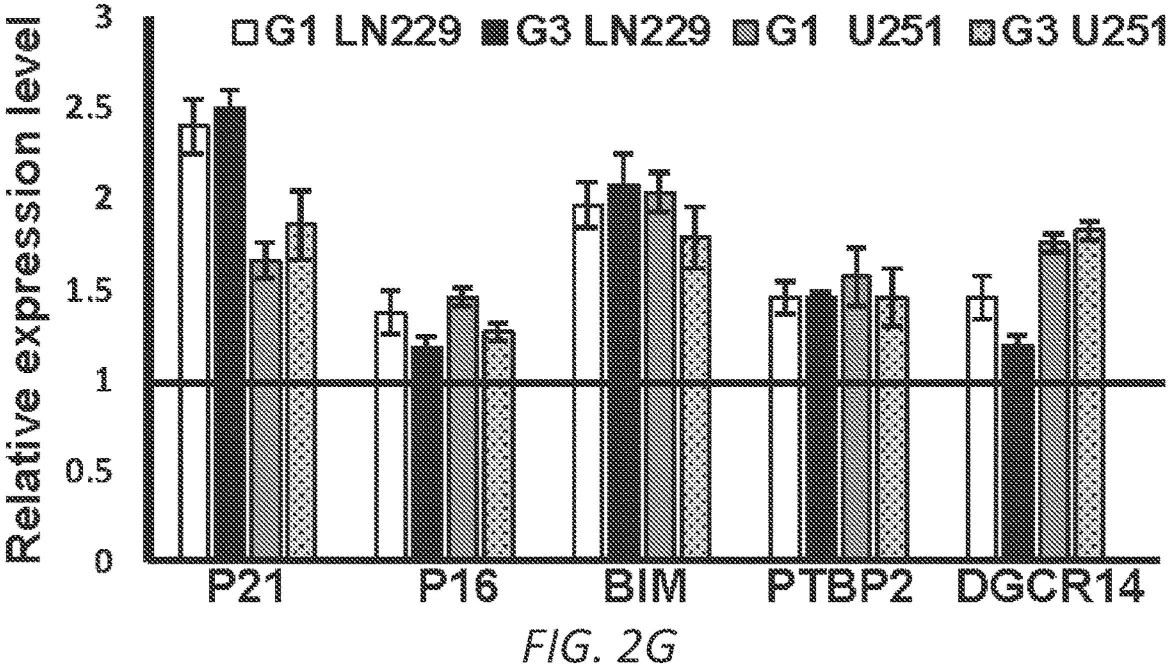

Although the CRISPR-Cas9 editing of miR-10b, and other highly expressed glioma miRNA genes such as miR-21, miR-139, and miR-107 proved efficient and reduced the levels of the respective miRNAs, only miR-10b editing impaired the viability of all tested glioma cell lines and GSC cultures (FIGS. 2A, B, C). Overall, we observed correlation between the efficacy of miR-10b gene editing and the viability of monolayer GBM cell lines, with the exception of low-passage GSC (GBM8) cells cultured in neurospheres, which were extremely sensitive to even less-efficient miR-10b editing (FIG. 2C). Importantly, reduced viability was rescued by sequential transfections with the miR-10b synthetic mimic, indicating that the phenotype observed in miR-10b-targeted cultures was, indeed, caused by its loss (FIG. 2D). This rescue was partial, possibly due to the "imperfect" intracellular trafficking and incorporation of the synthetic mimic to the functional RISC complex, not fully mimicking the endogenous miR-10b activity, as well as additional unknown off-target effects. Efficient miR-10b gene editing in metastatic triple negative ($ER^-/PR^-/HER2^{low}$) breast carcinoma line MDA-MB-231 reduced cell migration but not viability (FIG. 2E and FIG. 7), consistent with the established role of miR-10b in breast cancer metastasis but not survival (10, 11). Of note, a similar CRISPR-Cas9 strategy failed to edit miR-10b gene in the cell types not expressing miR-10b, such as non-metastatic breast carcinoma MCF7 and primary astrocytes (FIGS. 2A, F). Although miR-10b editing affected only a part of cells in targeted cultures, it led to the elevated expression of the previously validated miR-10b targets including the mediator of apoptosis Bim, cell cycle inhibitors p21 and p16, and splicing regulator PTBP2 (FIG. 2G).

Due to the imperfect efficacy of the CRISPR/Cas9 editing, the G1-G3 targeted glioma cultures were expected to contain a variety of miR-10b mutants and indels, as well as the cells with wild type miR-10b gene. Correspondingly, miR-10b editing of glioma cell lines that normally grew in a monolayer resulted in a production of mixed cell population containing distinctly apoptotic round floating cells, as well as unaffected attached cells with normal morphology (FIG. 3A, Table 3). To investigate whether miR-10b editing indeed leads to glioma cell death, we analyzed the cells of these mixed cultures. Glioma cells from the miR-10b-targeted cultures were plated as single cells in 96 individual wells, which led to the growth of 53 single-cell-derived clones. The DNA was extracted from these clones and miR-10b gene was sequenced. Strikingly, no mutations were found among the viable clones examined (0/53). In contrast, clonal analysis of the DNA collected from the floating apoptotic cells in the targeted parental cultures revealed 85% mutation rate in the miR-10b locus (FIG. 3A). Consistent with these findings, in the parental cultures the miR-10b gene was efficiently edited in the floating pro-apoptotic cells but unedited in the attached viable cells (FIG. 3B). Correspondingly, miR-10b levels were 20-30-fold lower in floating pro-apoptotic cells than in attached viable cells (FIG. 3C). Collectively, these results indicate that glioma cells are addicted to miR-10b, and expression of this molecule is essential for glioma viability and survival.

TABLE 3

| | Sequence | SEQ ID NO: |
|---|---|---|
| Wt | TTGTCTATATATACCCT-------- GTAGAACCGAATTTGTGTGGTATCCGTATAGTCACAGATTCGA | 75 |
| 1 | TTGTCT-----TGTCCGGAATTTGTG---------------- TGGTATCCGTATAGTCACAGATTCGA | 76 |
| 2 | -TGTGT-----CGTC--GAATTTGTG---------------- TGGTATCCGTATAGTCACAGATTCGA | 77 |
| 3 | TTGTCTATATATACCCT-------- GTAGAACCGAATTTGTGTGGTATCCGTATAGTCACAGATTCGA | 78 |
| 4 | --------------------------------------------------- TAGTCACAGATTCGA | 79 |
| 5 | TTGT--------------------- GTAGAACCGAATTTGTGTGGTATCCGTATAGTCACAGATTCGA | 80 |
| 6 | ---------------------TTGTG---------------- TGGTATCCGTATAGTCACAGATTCGA | 81 |
| 7 | TTGTCT-----A------------- GTAGAACCGAATTTGTGTGGTATCCGTATAGTCACAGATTCGA | 82 |
| 8 | TTGTCTATATA---------------------------------------- -------------- | 83 |
| 9 | TTGTCTATATA---------------------------------------- -------------- | 84 |
| 10 | TTGTCTATATAC--------------------- GAATTTGTGTGGTATCCGTATAGTCACAGATTCGA | 85 |
| 11 | TTGTCTATATATACCCT-------- GTAGAACCGAATTTGTGTGGTATCCGTATAGTCACAGATTCGA | 86 |

TABLE 3-continued

| Sequence | SEQ ID NO: |
|---|---|
| 12 ------------------ TTGTCTATATGAACCGAATTTGTGTGGTATCCGTATAGTCACAGATTCGA | 87 |
| 13 TTGTCTATATATACCCT-------- GTAGAACCGAATTTGTGTGGTATCCGTATAGTCACAGATTCGA | 88 |
| 14 TTGTCTATATATACCCT--------GTA------------- GTGGTATCCGTATAGTCACAGATTCGA | 89 |
| 15 -TGT-------------------G---------------- TGGTATCCGTATAGTCACAGATTCGA | 90 |
| 16 TTGTCTATATATACCCT--------GTAGAACCGAAT-- GTGTGGTATCCGTATAGTCACAGATTCGA | 91 |
| 17 TTGTCTAT------------------------------------ GTATCCGTATAGTCACAGATTCGA | 92 |
| 18 TTGTCTATATATACCT----------------------- GTGTGGTATCCGTATAGTCACAGATTCGA | 93 |
| 19 TTGTCTATATATATTT----------------------- GTGTGGTATCCGTATAGTCACAGATTCGA | 94 |
| 20 TTGTCTATATATACCCT--------GTAGAACCGAA-G- GTGTGGTATCCGTATAGTCACAGATTCGA | 95 |

Example 1.3 miR-10b Editing Impairs Tumor Growth in Intracranial GBM Models

Figure 4A:
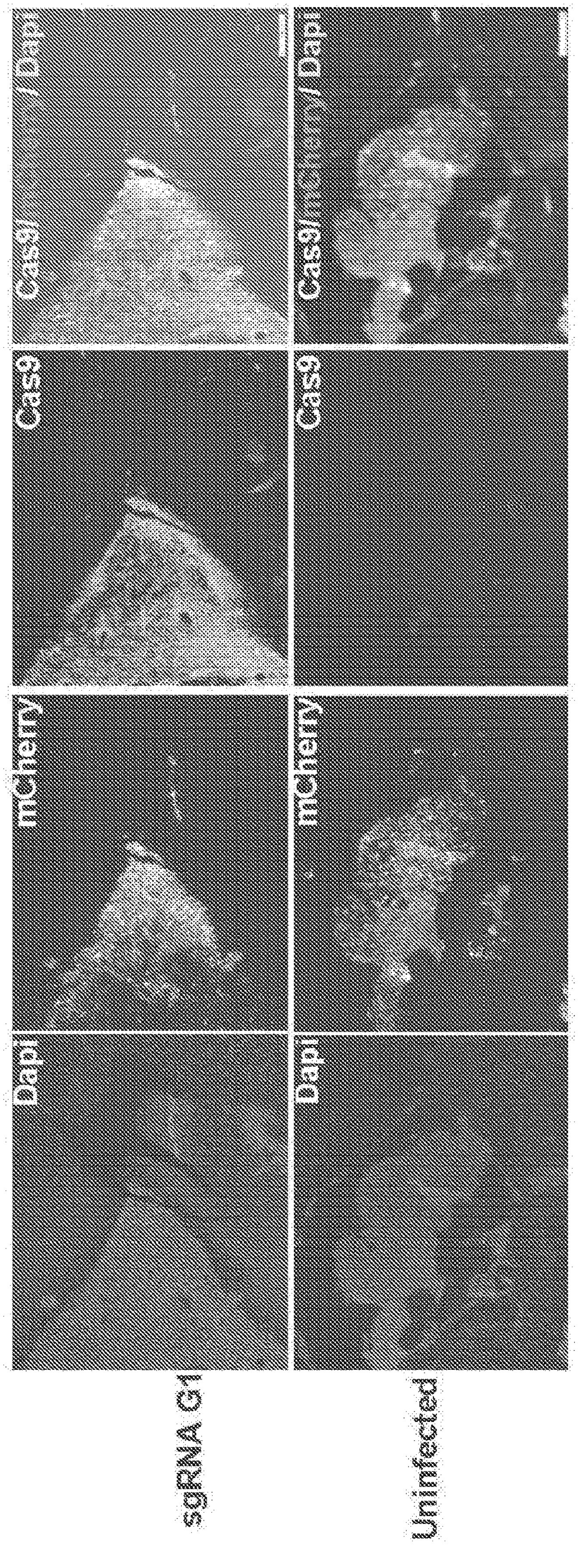
Figure 4B:
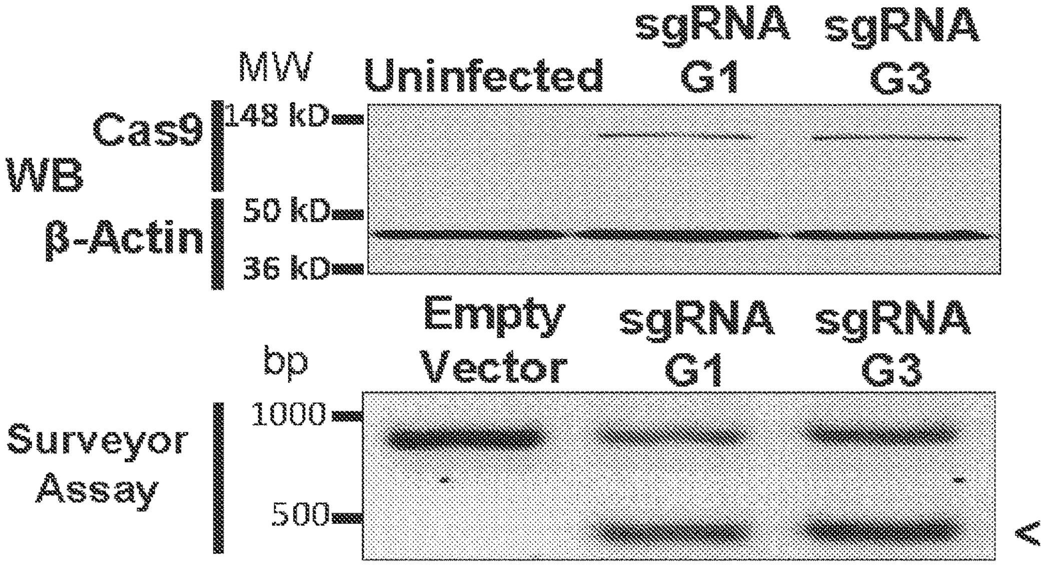
Figure 4C:
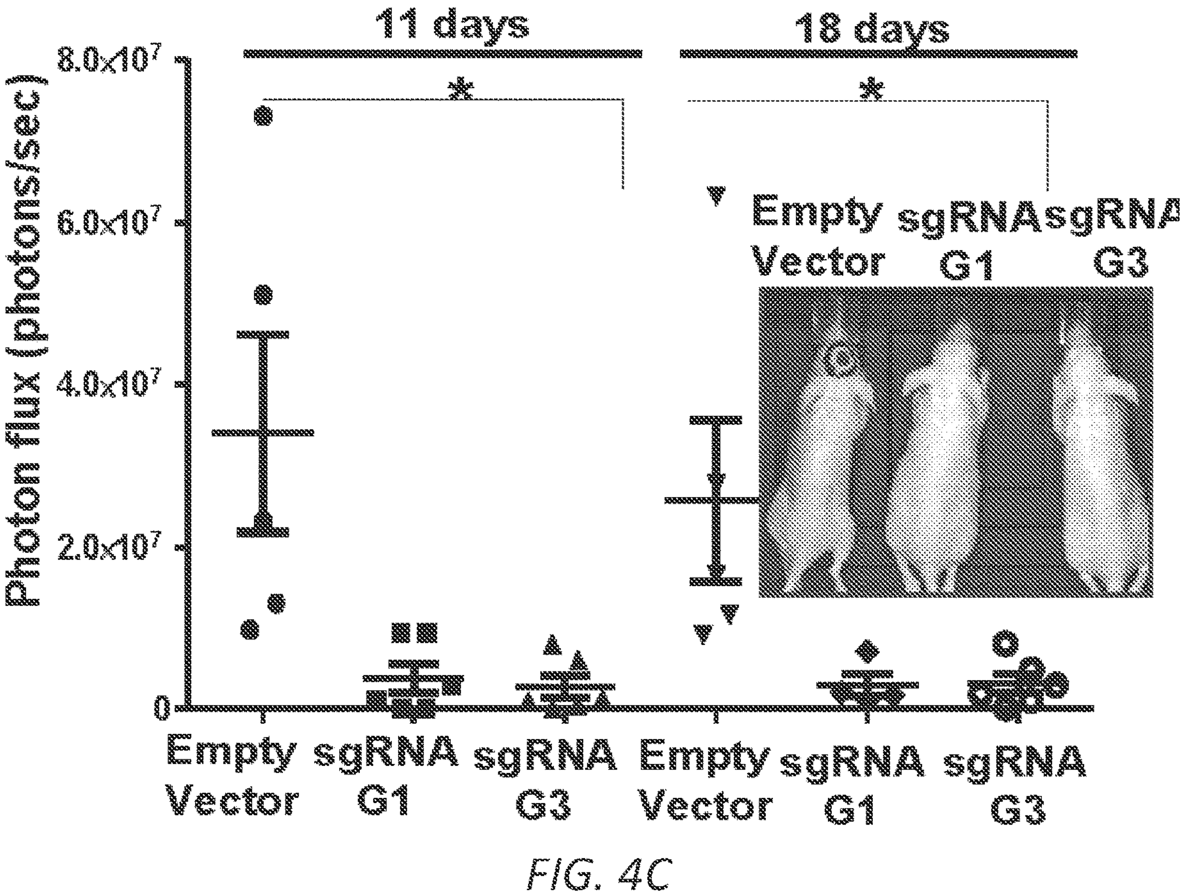
Figure 4D:
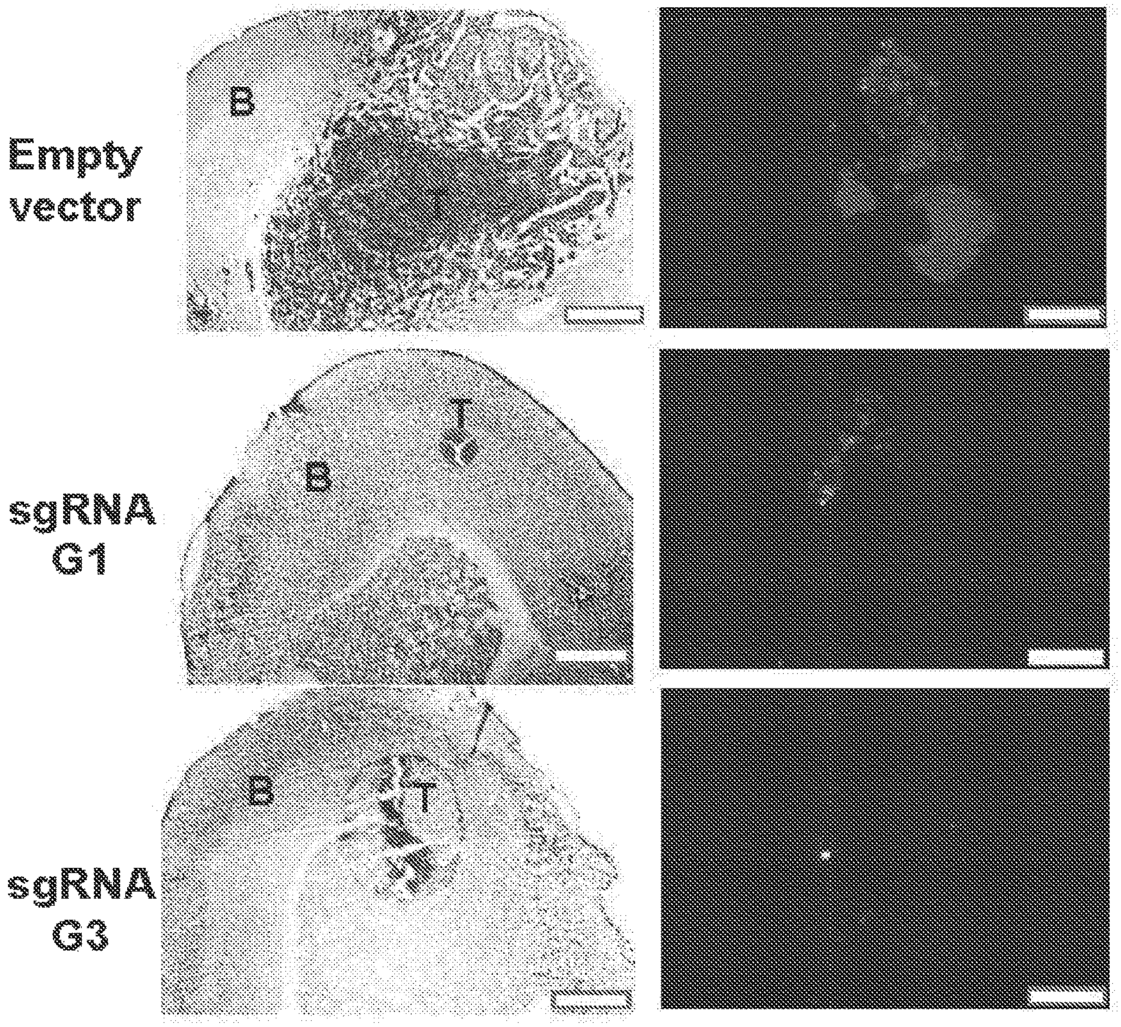
Figure 4E:
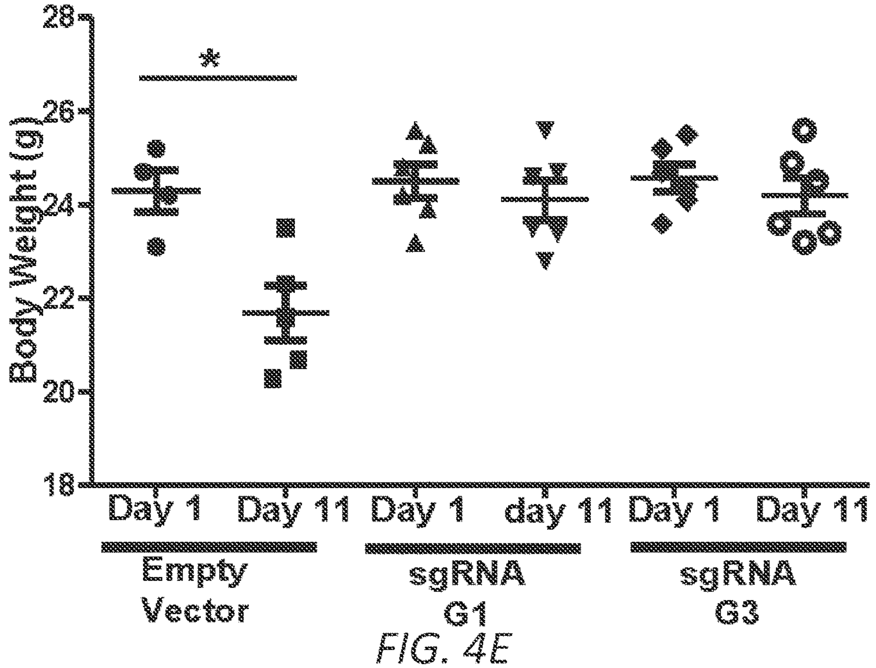

To investigate the effects of miR-10b gene editing in orthotopic GBM models in vivo, we produced a miR-10b-targeting lentiCrisprv2 plasmid, based on (19, 20), a single vector expressing Cas9, either G1 or G3 sgRNA, a puromycin selection marker, and packaged it to a VSV-G protein-pseudotyped lentivirus. High-titer ($10^8$ TU/ml) viral miR-10b-targeting resulted in efficient editing and reduced cell viability of various genetically distinct glioma cell lines and GSC cultures (FIG. 8A-B). Intratumoral injections of miR-10b targeting virus to established exponentially growing orthotopic LN229-formed GBM xenografts resulted in a tumor-specific Cas9 expression and efficient miR-10b editing in the tumor tissue, with very little Cas9 immunostaining in surrounding brain parenchyma (FIGS. 4A, B). Tumor growth, monitored by in vivo imaging, was strongly reduced in miR-10b targeted G1 and G3 groups relative to the control group injected with the corresponding empty virus that expresses Cas9 but lacks miR-10b-targeting sgRNA (FIG. 4C). Histological analysis of the brains harvested on day 18 after a viral injection revealed barely visible tumors in both G1 and G3 treatment groups while large tumors were found in controls (FIG. 4D). Both treatment groups also had better maintenance of body weight compared with controls (FIG. 4E). Similar results were obtained on a highly invasive GBM8 xenograft model treated with the mutated "nickase" version of the virus-encoded Cas9n D10A enzyme, and guided by the pair of G1 and G3 sgRNAs (nG1/G3; FIGS. 9 and 10A, B). Single injection of the miR-10b editing vector effectively blocked the growth of orthotopic GBM8, and rescued body weight of the animals. In addition, miR-10b editing significantly extended animal survival in these orthotopic GBM models (FIG. 12).

Example 1.4 miR-10b Editing Abolishes Transformation of Normal Astrocytes

Figure 5A:
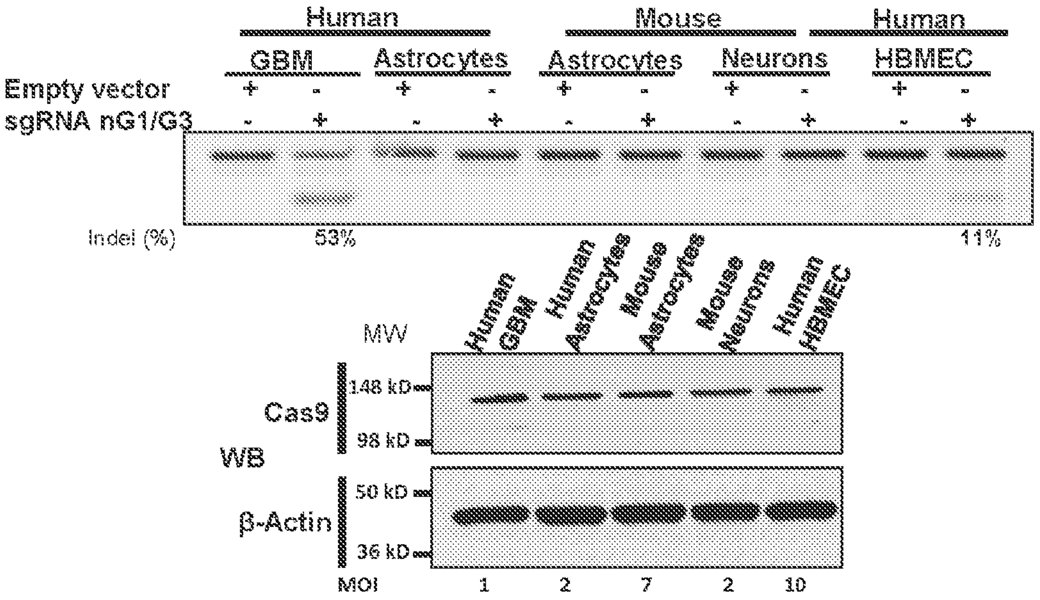
Figure 5B:
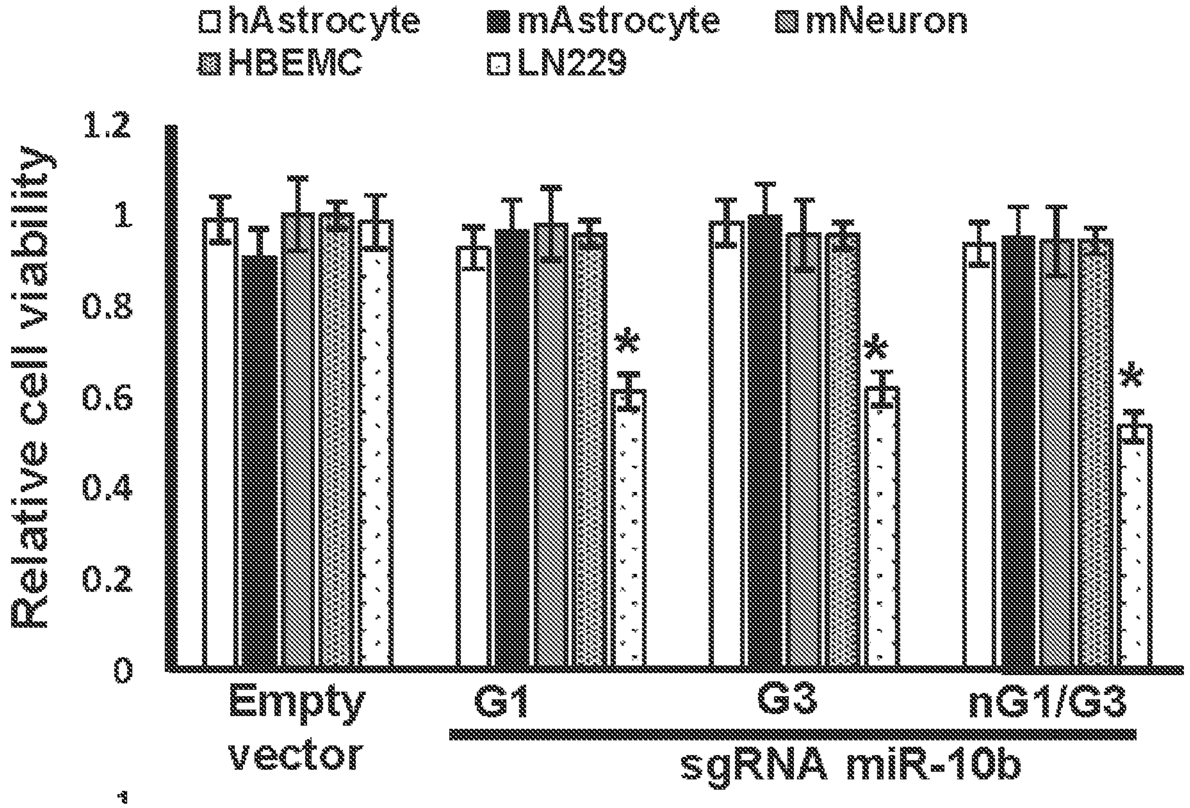
Figure 5C:
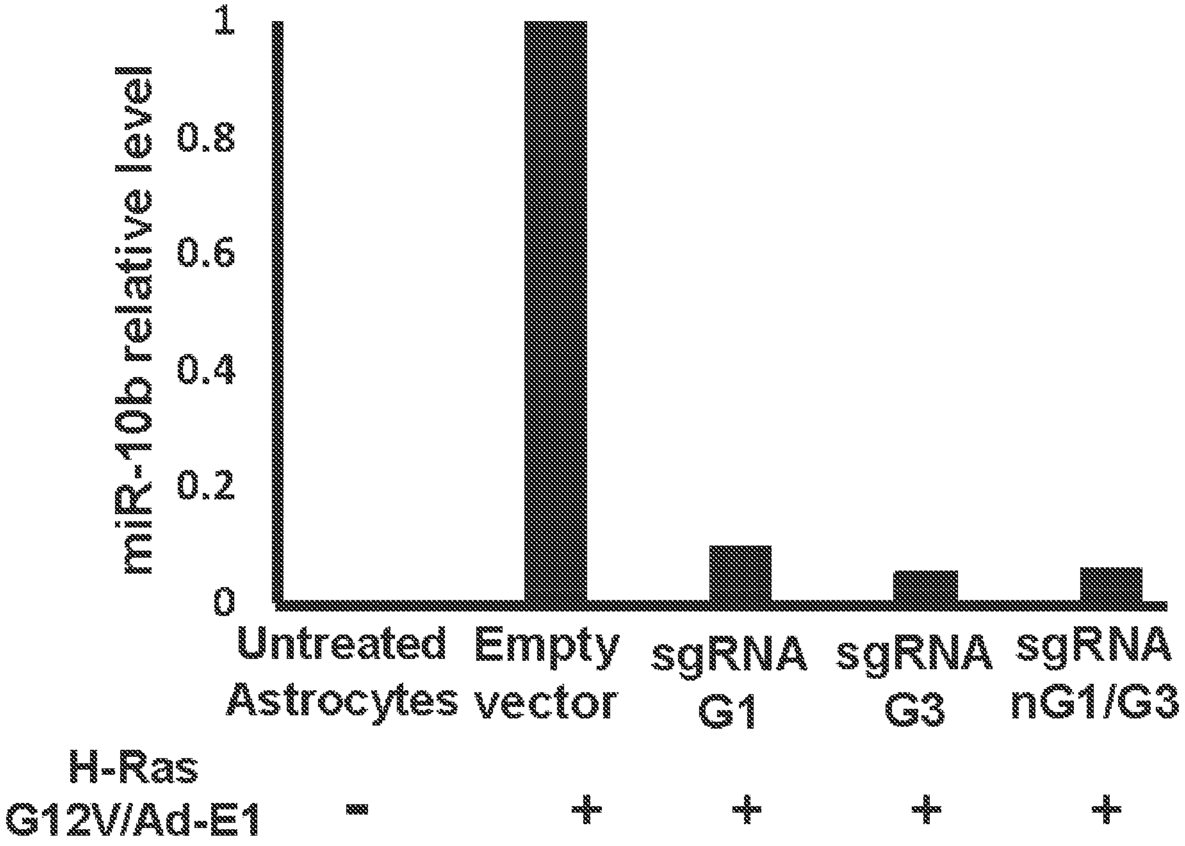
Figure 5D:
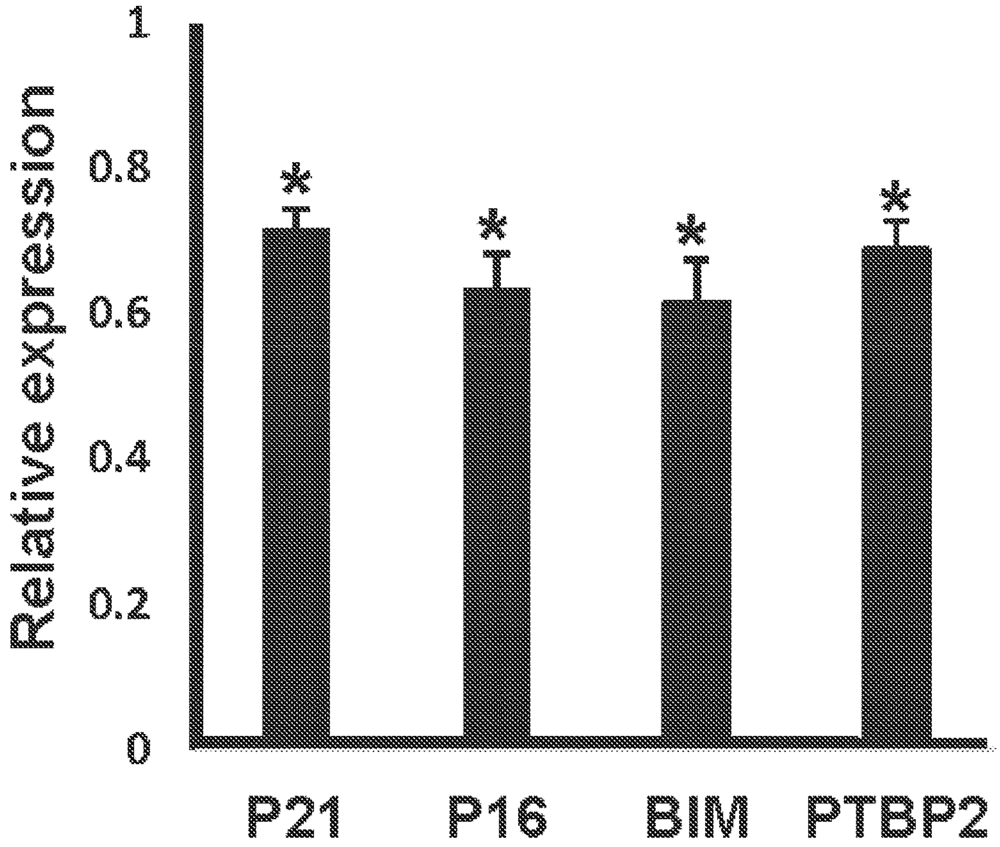
Figure 5E:
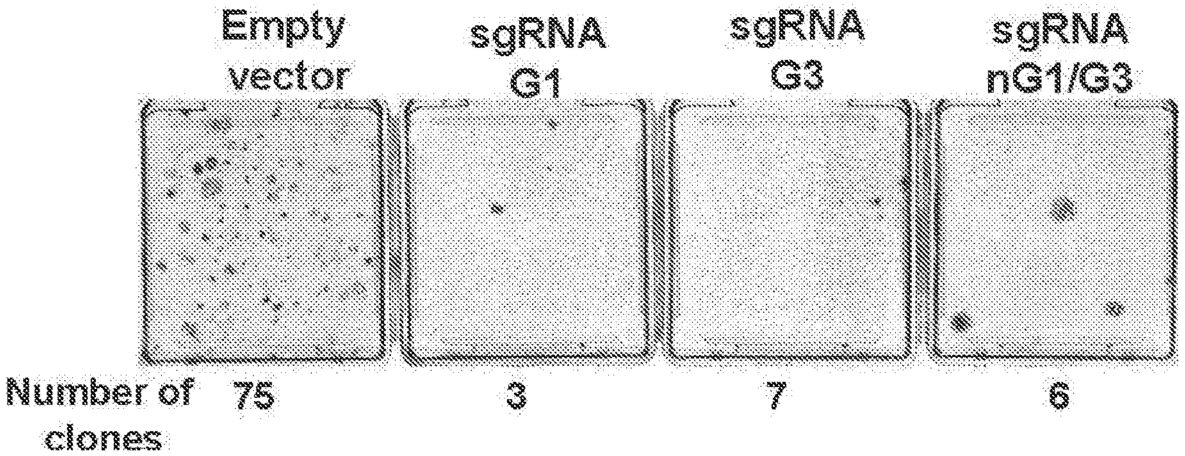
Figure 5F:
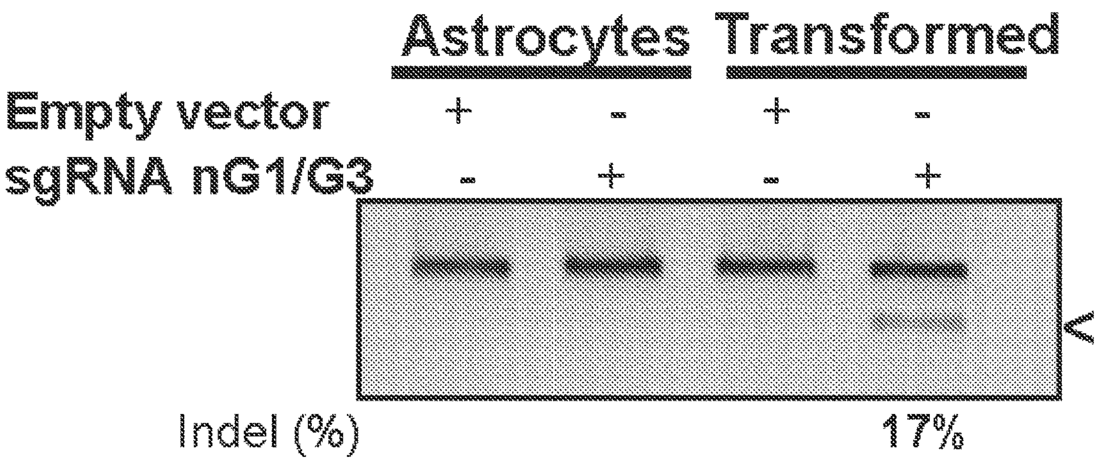
Figure 5G:
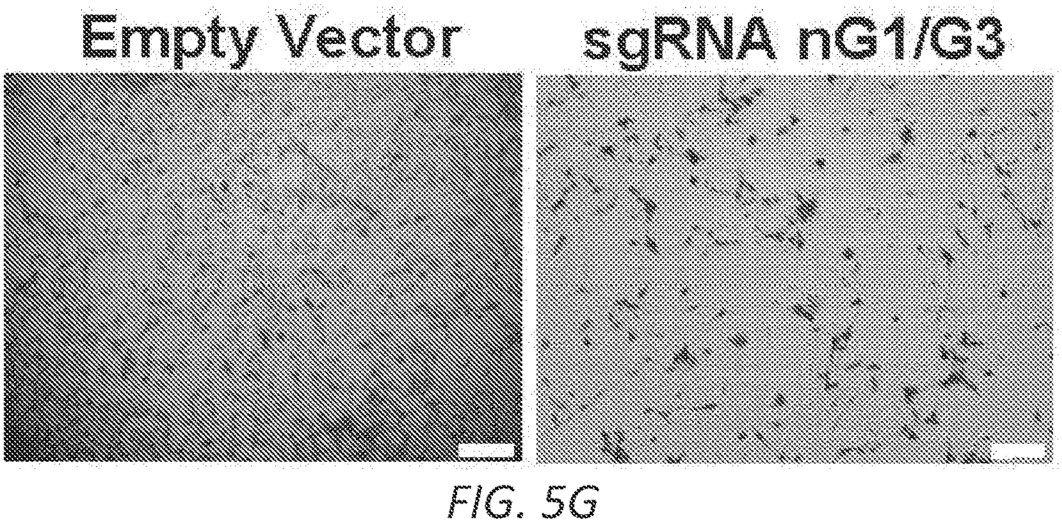
Figure 5H:
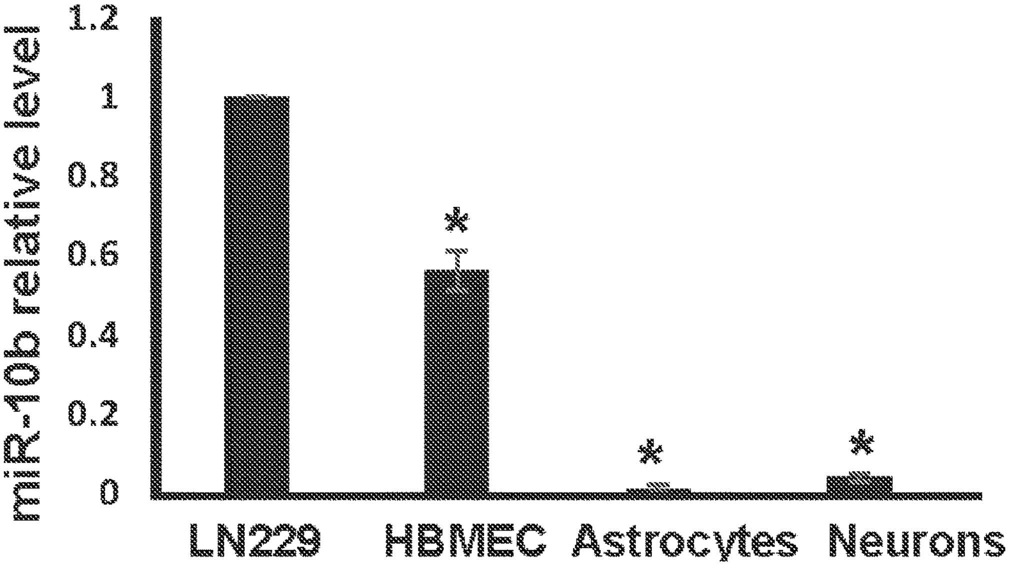

Primary mouse and human astrocytes do not express miR-10b (4). Of note, transductions of human and mouse primary astrocytes, as well as mouse primary neurons with miR-10b editing lentivirus at the MOI range that led to similar levels of Cas9 expression in those cells, resulted in neither miR-10b editing nor phenotypic effects on these cells (FIGS. 5A, B). Similarly, CRISPR/Cas9 vectors at the fixed titer of $3\times10^5$ TU were highly efficient in glioma but not in normal human or murine neuroglial cells (FIG. 11). However, when primary mouse astrocytes underwent oncogenic transformation by H-RasG12V/Ad-E1 or SV40 large T antigen oncogenes, they strongly up-regulated miR-10b (FIG. 5C) and down-regulated the levels of validated miR-10b targets p21, p16, BIM, and PTBP2 (FIG. 5D). miR-10b up-regulation was abolished by transduction with miR-10b-editing lentiCRISPR vectors, indicating that transformed astrocytes become editable in this locus (FIG. 5C). Furthermore, miR-10b editing in oncogene-induced astrocytes markedly reduced the number of transformed colonies, suggesting that miR-10b is required for transformation or essential for the survival of transformed astrocytes (FIG. 5E). When miR-10b editing was performed post-transformation, it caused death of the transformed cells similarly to the effect on glioma cells (FIGS. 5F, G). Of note, the only principal type of the normal brain cells expressing miR-10b is the brain-derived microvascular endothelial cells (HBMECs) (FIG. 5H). The efficiency of miR-10b gene editing in these cells, however, was much lower than in glioma cells, and even the high-titer virus has not affected their viability and morphology (FIGS. 5A, B).

Example 1.5 miR-10b Editing Using Alternative Cas9s

The effect of miR-10b editing is evaluated using alternative Cas9s, e.g., from SaCas9 or NmCas9, which have different PAM sequences (see Table D). Possible target sequences are shown above in Tables B and C.

The CRISPR elements are inserted into a lentivirus, AAV, and/or adenovirus for transduction. For example, a human codon-optimized saCas9 and sanCAS9 (D10A) from *Staphylococcus aureus* (SaCas9) derived from pX600, 601 and 602-AAV-CMV::NLS-SaCas9-NLS-3xHA-bGHpA (Zhang lab, MIT), modified to insert miR-10b-editing sgRNA(s). Alternatively, a separate vector for tandem expression of a pair of sgRNAs from two independent U6 promoters is used.

As another example, NmCas9 is expressed from a mammalian Expression vector derived from pSimpleII-U6-tracr-U6-BsmBI-NLS-NmCas9-HA-NLS(s) (Erik Sontheimer and James Thomson laboratories). This plasmid contains expression cassette for NmCas9 with N and C NLS and an HA tag, a cassette for expression of tracrRNA, and a cassette for cloning sgRNA under the control of U6 promoter. An alternative vector is the PX405 *Neisseria meningitidis* Cas9 (Zhang Lab, MIT).

The original constructs are used as templates for cloning and incorporation in Lentivirus, Adenovirus and AAV (AAV1, AAV2, AAV8, AAV9, AAVrh10).

REFERENCES

1. Floyd D, Purow B (2014) Micro-masters of glioblastoma biology and therapy: increasingly recognized roles for microRNAs. Neuro Oncol. 16(5):622-7.
2. Biagioni F, Bossel Ben-Moshe N, Fontemaggi G, Yarden Y, Domany E, Blandino G, (2013) The locus of microRNA-10b: a critical target for breast cancer insurgence and dissemination. Cell Cycle. 12(15):2371-5. Review
3. Tehler D, Hoyland-Kroghsbo N M, Lund A H (2011) The miR-10 microRNA precursor family. RNA Biol. 8(5):728-34.
4. Gabriely G, Yi M, Narayan R S, Niers J M, Wurdinger T, Imitola J, et al., (2011) Human glioma growth is controlled by microRNA-10b. Cancer Res 71: 3563-72.
5. Teplyuk N M, Mollenhauer B, Gabriely G, Giese A, Kim E, Smolsky M, et al., (2012). MicroRNAs in cerebrospinal fluid identify glioblastoma and metastatic brain cancers and reflect disease activity. Neuro Oncol 14: 689-700.
6. Sun L, Yan W, Wang Y, Sun G, Luo H, Zhang J, et al. (2011) MicroRNA-10b induces glioma cell invasion by modulating MMP-14 and uPAR expression via HOXD10. Brain Res. 1389:9-18.
7. Ahmad A, Sethi S, Chen W, Ali-Fehmi R, Mittal S, Sarkar F H, (2014) Up-regulation of microRNA-10b is associated with the development of breast cancer brain metastasis. Am J Transl Res. 6(4):384-90.
8. Parrella P, Barbano R, Pasculli B, Fontana A, Copetti M, Valori V M et al., (2014) Evaluation of microRNA-10b prognostic significance in a prospective cohort of breast cancer patients. Mol Cancer 13:142.
9. Guessous F, Alvarado-Velez M, Marcinkiewicz L, Zhang Y, Kim J, Heister S et al., (2013) Oncogenic effects of miR-10b in glioblastoma stem cells. J Neurooncol 112(2):153-63.
10. Ma L, Reinhardt F, Pan E, Soutschek J, Bhat B, Marcusson E G et al., (2010) Therapeutic silencing of miR-10b inhibits metastasis in a mouse mammary tumor model. Nat Biotechnol 28: 341-7.
11. Ma L, Teruya-Feldstein J, Weinberg R A, (2007) Tumour invasion and metastasis initiated by microRNA-10b in breast cancer. Nature 449: 682-8.
12. Teplyuk N M, Uhlmann E J, Gabriely G, Volfovsky N, Wang Y, Teng J et al., (2016) Therapeutic potential of targeting microRNA-10b in established intracranial glioblastoma: first steps toward the clinic. EMBO Mol Med, 10.15252/emmm.201505495.
13. Doudna J A, Charpentier E (2014) Genome editing. The new frontier of genome engineering with CRISPR-Cas9. Science. 346(6213):1258096.
14. Swiech L, Heidenreich M, Banerjee A, Habib N, Li Y, Trombetta J et al., (2015) In vivo interrogation of gene function in the mammalian brain using CRISPR-Cas9. Nat Biotechnol 33(1):102-6.
15. Davis L and Maizels N (2014) Homology-directed repair of DNA nicks via pathways distinct from canonical double-strand break repair. Proc Natl Acad Sci USA.
16. Sander J D and Joung J K (2014) CRISPR Cas systems for editing regulating and targeting genomes. Nat Biotechnol. 32(4): 347-55. Review.
17. Kleinstiver B P, Prew MS, Tsai S Q, Topkar V V, Nguyen N T, Zheng Z et al., (2015) Engineered CRISPR-Cas9 nucleases with altered PAM specificities. Nature 523(7561):481-5.
18. Ran F A, Hsu P D, Lin C Y, Gootenberg J S, Konermann S, Trevino A E et al., (2013) Double nicking by RNA-guided CRISPR Cas9 for enhanced genome editing specificity. Cell 154: 1380-9.
19. Shalem O, Sanjana N E, Hartenian E, Shi X, Scott D A, Mikkelsen T S et al., (2014). Genome-scale CRISPR-Cas9 knockout screening in human cells. Science 343: 84-7.
20. Sanjana N E, Shalem O, Zhang F (2014). Improved vectors and genome-wide libraries for CRISPR screening. Nat Methods 11: 783-4.
21. Tian Y, Luo A, Cai Y, Su Q, Ding F, Chen H et al., (2010) MicroRNA-10b promotes migration and invasion through KLF4 in human esophageal cancer cell lines. J Biol Chem. 12;285(11):7986-94.
22. Zhang X H, Tee L Y, Wang X G, Huang Q S, Yang S H (2015) Off-target Effects in CRISPR/Cas9-mediated Genome Engineering. Mol Ther Nucleic Acids. 4:e264.
23. Incontro S, Asensio C S, Edwards R H, Nicoll R A (2014) Efficient, complete deletion of synaptic proteins using CRISPR. Neuron. 83(5):1051-7.
24. Straub C, Granger A J, Saulnier J L, Sabatini B L (2014) CRISPR/Cas9-mediated gene knock-down in post-mitotic neurons, PLoS One. 9(8):e105584.
25. Goldberg G W, Jiang W, Bikard D, Marraffini L A (2014) Conditional tolerance of temperate phages via transcription-dependent CRISPR-Cas targeting. Nature. 514(7524):633-7.
26. Huszthy P C, Giroglou T, Tsinkalovsky O, Euskirchen P, Skaftnesmo K O, Bjerkvig Ret al., (2009) Remission of invasive, cancer stem-like glioblastoma xenografts using lentiviral vector-mediated suicide gene therapy. PLoS One. 4(7):e6314.
27. Bayin N S, Modrek A S, Dietrich A, Lebowitz J, Abel T, Song H R et al., (2014) Selective lentiviral gene delivery to CD133-expressing human glioblastoma stem cells. PLoS One. 9(12):e116114.
28. DePolo N J, Reed J D, Sheridan P L, Townsend K, Sauter S L, Jolly D J et al., (2000) VSV-G pseudotyped lentiviral vector particles produced in human cells are inactivated by human serum. Mol Ther. 2(3):218-22.

29. Ran F A, Hsu P D, Wright J, Agarwala V, Scott D A, Zhang F, (2013). Genome engineering using the CRISPR-Cas9 system. Nat Protoc 8: 2281-308.
30. Ran F A, Cong L, Yan W X, Scott D A, Gootenberg J S, Kriz A J et al., (2015) In vivo genome editing using *Staphylococcus aureus* Cas9. Nature. 520(7546): 186-91.
31. Kiani S, Chavez A, Tuttle M, Hall R N, Chari R, Ter-Ovanesyan D et al., (2015) Cas9 gRNA engineering for genome editing, activation and repression. Nat Methods. 12(11): 1051-4.
32. Cong L, Ran F A, Cox D, Lin S, Barretto R, Habib N et al., (2013) Multiplex genome engineering using CRISPR/Cas systems. Science 339(6121):819-23.
33. Wakimoto H, Mohapatra G, Kanai R, Curry W T Jr, Yip S, Nitta M et al., (2012) Maintenance of primary tumor phenotype and genotype in glioblastoma stem cells. Neuro Oncol. 14(2):132-44.
34. Wong H K, EL Fatimy R, Onodera C, Wei Z, Yi M, Mohan A et al., (2015) The Cancer Genome Atlas Analysis Predicts MicroRNA for Targeting Cancer Growth and Vascularization in Glioblastoma. Mol Ther. 23(7):1234-47.
35. Rodriguez LG, Wu X, Guan J L (2005) Wound-healing assay. Methods Mol Bio1.294:23-9.
36. Festing M F, Altman D G (2002) Guidelines for the design and statistical analysis of experiments using laboratory animals. ILAR J. 43(4):244-58.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a subject who has glioma, the method comprising administering to the subject a therapeutically effective amount of a Clustered Regularly Interspaced Short Palindromic Repeats (CRISPR) microRNA-10a/microRNA-10b (miR-10a/10b) editing complex comprising a CRISPR Associated Protein 9 (Cas9) and at least one guide RNA comprising SEQ ID NO:27 or SEQ ID NO: 29;

wherein the Cas9 is administered in a viral vector comprising a sequence encoding the Cas9 protein, and the viral vector encoding the Cas9 is selected from recombinant adenovirus and lentivirus; and wherein the at least one guide RNA is administered in a viral vector comprising a sequence encoding the at least one gRNA, and the viral vector encoding the at least one guide RNA is selected from recombinant adenovirus and lentivirus.

2. The method of claim 1, wherein the glioma is an astrocytoma, oligodendroglioma, or glioblastoma multiforme (GBM) tumor.

3. The method of claim 1, wherein the viral vector encoding the Cas9 is recombinant adenovirus.

4. The method of claim 1, wherein the viral vector encoding the Cas9 is recombinant lentivirus.

5. The method of claim 1, wherein the viral vector encoding the at least one guide RNA is a recombinant adenovirus.

6. The method of claim 1, wherein the viral vector encoding the at least one guide RNA is a recombinant lentivirus.

7. The method of claim 1, wherein the complex is administered as a viral vector comprising a sequence encoding the Cas9 protein and a sequence encoding the at least one guide RNA, and the Cas9 protein and the guide RNA are expressed from the same viral vector, wherein the viral vector is an adenovirus.

8. The method of claim 1, wherein the complex is administered as a single nucleic acid viral vector comprising a sequence encoding the Cas9 protein and a sequence encoding the at least one guide RNA, and the Cas9 protein and the at least one guide RNA are expressed from the same viral vector, wherein the viral vector is a lentivirus.

9. The method of claim 1, wherein the Cas9 is *Streptococcus thermophilus* (ST) Cas9 (StCas9); *Treponema denticola* (TD) (TdCas9); *Streptococcus pyogenes* (SP) (SpCas9); *Staphylococcus aureus* (SA) Cas9 (SaCas9); or *Neisseria meningitidis* (NM) Cas9 (NmCas9), or a variant thereof.

10. The method of claim 9, wherein the Cas9 is SpCas9 or a variant of SpCas9 selected from the group consisting of SpCas9 D1135E variant; SpCas9 VRER variant; SpCas9 EQR variant; and SpCas9 VQR variant.

11. The method of claim 1, further comprising a guide RNA targeting miR-10b is complementary to 17-20 nucleotides of SEQ ID NO:1 or 24, and/or the guide RNA targeting miR-10a is complementary to 17-20 nucleotides of SEQ ID NO:25 or 26.

12. The method of claim 1, wherein the CRISPR miR-10a/10b editing complex is administered systemically, locally to a tumor, or locally to the site of a tumor after complete or partial surgical resection.

13. The method of claim 1, wherein the CRISPR miR-10a/10b editing complex is administered intrathecally.

14. The method of claim 1, wherein the CRISPR miR-10a/10b editing complex is formulated to be administered in a composition comprising a biodegradable, biocompatible polymer.

15. The method of claim 14, wherein the biodegradable, biocompatible polymer is selected from the group consisting of collagen, ethylene vinyl acetate, polyanhydrides, polyglycolic acid, collagen, polyorthoesters, polyethyleneglycol-coated liposomes, and polylactic acid.

* * * * *

SEQUENCE LISTING

```
<160> NUMBER OF SEQ ID NOS: 97

<210> SEQ ID NO 1
<211> LENGTH: 110
<212> TYPE: DNA
<213> ORGANISM: Homo sapiens

<400> SEQUENCE: 1

ccagaggttg taacgttgtc tatatatacc ctgtagaacc gaatttgtgt ggtatccgta      60

tagtcacaga ttcgattcta ggggaatata tggtcgatgc aaaaacttca                110


<210> SEQ ID NO 2
<211> LENGTH: 23
<212> TYPE: DNA
<213> ORGANISM: Artificial Sequence
<220> FEATURE:
<223> OTHER INFORMATION: Artificial, sgRNA Target sequence

<400> SEQUENCE: 2

atagacaacg ttacaacctc tgg                                              23


<210> SEQ ID NO 3
<211> LENGTH: 23
<212> TYPE: DNA
<213> ORGANISM: Artificial Sequence
<220> FEATURE:
<223> OTHER INFORMATION: sgRNA Target sequence

<400> SEQUENCE: 3

cacacaaatt cggttctaca ggg                                              23


<210> SEQ ID NO 4
<211> LENGTH: 23
<212> TYPE: DNA
<213> ORGANISM: Artificial Sequence
<220> FEATURE:
<223> OTHER INFORMATION: sgRNA Target sequence

<400> SEQUENCE: 4

cctgtagaac cgaatttgtg tgg                                              23


<210> SEQ ID NO 5
<211> LENGTH: 23
<212> TYPE: DNA
```

-continued

<213> ORGANISM: Artificial Sequence
<220> FEATURE:
<223> OTHER INFORMATION: sgRNA Target sequence

<400> SEQUENCE: 5
ccacacaaat tcggttctac agg 23

<210> SEQ ID NO 6
<211> LENGTH: 23
<212> TYPE: DNA
<213> ORGANISM: Artificial Sequence
<220> FEATURE:
<223> OTHER INFORMATION: sgRNA Target sequence

<400> SEQUENCE: 6
atacggatac cacacaaatt cgg 23

<210> SEQ ID NO 7
<211> LENGTH: 23
<212> TYPE: DNA
<213> ORGANISM: Artificial Sequence
<220> FEATURE:
<223> OTHER INFORMATION: sgRNA Target sequence

<400> SEQUENCE: 7
gaatcgaatc tgtgactata cgg 23

<210> SEQ ID NO 8
<211> LENGTH: 23
<212> TYPE: DNA
<213> ORGANISM: Artificial Sequence
<220> FEATURE:
<223> OTHER INFORMATION: sgRNA Target sequence

<400> SEQUENCE: 8
atagtcacag attcgattct agg 23

<210> SEQ ID NO 9
<211> LENGTH: 23
<212> TYPE: DNA
<213> ORGANISM: Artificial Sequence
<220> FEATURE:
<223> OTHER INFORMATION: sgRNA Target sequence

<400> SEQUENCE: 9
tagtcacaga ttcgattcta ggg 23

<210> SEQ ID NO 10
<211> LENGTH: 23
<212> TYPE: DNA
<213> ORGANISM: Artificial Sequence
<220> FEATURE:
<223> OTHER INFORMATION: sgRNA Target sequence

<400> SEQUENCE: 10
agtcacagat tcgattctag ggg 23

<210> SEQ ID NO 11
<211> LENGTH: 23
<212> TYPE: DNA
<213> ORGANISM: Artificial Sequence
<220> FEATURE:
<223> OTHER INFORMATION: sgRNA Target sequence

<400> SEQUENCE: 11
ttcgattcta ggggaatata tgg 23

<210> SEQ ID NO 12
<211> LENGTH: 26
<212> TYPE: DNA
<213> ORGANISM: Artificial Sequence
<220> FEATURE:
<223> OTHER INFORMATION: sgRNA Target sequence

<400> SEQUENCE: 12
tctatatata ccctgtagaa ccgaat                                          26

<210> SEQ ID NO 13
<211> LENGTH: 26
<212> TYPE: DNA
<213> ORGANISM: Artificial Sequence
<220> FEATURE:
<223> OTHER INFORMATION: sgRNA Target sequence

<400> SEQUENCE: 13
accacacaaa ttcggttcta cagggt                                          26

<210> SEQ ID NO 14
<211> LENGTH: 26
<212> TYPE: DNA
<213> ORGANISM: Artificial Sequence
<220> FEATURE:
<223> OTHER INFORMATION: sgRNA Target sequence

<400> SEQUENCE: 14
agaatcgaat ctgtgactat acggat                                          26

<210> SEQ ID NO 15
<211> LENGTH: 26
<212> TYPE: DNA
<213> ORGANISM: Artificial Sequence
<220> FEATURE:
<223> OTHER INFORMATION: sgRNA Target sequence

<400> SEQUENCE: 15
agtcacagat tcgattctag gggaat                                          26

<210> SEQ ID NO 16
<211> LENGTH: 26
<212> TYPE: DNA
<213> ORGANISM: Artificial Sequence
<220> FEATURE:
<223> OTHER INFORMATION: sgRNA Target sequence

<400> SEQUENCE: 16
gaccatatat tcccctagaa tcgaat                                          26

<210> SEQ ID NO 17
<211> LENGTH: 26
<212> TYPE: DNA
<213> ORGANISM: Artificial Sequence
<220> FEATURE:
<223> OTHER INFORMATION: sgRNA Target sequence

<400> SEQUENCE: 17
gcatcgacca tatattcccc tagaat                                          26

<210> SEQ ID NO 18
<211> LENGTH: 32
<212> TYPE: DNA
<213> ORGANISM: Artificial Sequence
<220> FEATURE:

-continued

<223> OTHER INFORMATION: sgRNA Target sequence

<400> SEQUENCE: 18
gaatttgtgt ggtatccgta tagtcacaga tt 32

<210> SEQ ID NO 19
<211> LENGTH: 32
<212> TYPE: DNA
<213> ORGANISM: Artificial Sequence
<220> FEATURE:
<223> OTHER INFORMATION: sgRNA Target sequence

<400> SEQUENCE: 19
tgtgtggtat ccgtatagtc acagattcga tt 32

<210> SEQ ID NO 20
<211> LENGTH: 28
<212> TYPE: DNA
<213> ORGANISM: Artificial Sequence
<220> FEATURE:
<223> OTHER INFORMATION: sgRNA Target sequence

<400> SEQUENCE: 20
ttgtgtggta tccgtatagt cacagatt 28

<210> SEQ ID NO 21
<211> LENGTH: 28
<212> TYPE: DNA
<213> ORGANISM: Artificial Sequence
<220> FEATURE:
<223> OTHER INFORMATION: sgRNA Target sequence

<400> SEQUENCE: 21
tggtatccgt atagtcacag attcgatt 28

<210> SEQ ID NO 22
<211> LENGTH: 1368
<212> TYPE: PRT
<213> ORGANISM: Streptococcus pyogenes

<400> SEQUENCE: 22

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160
```

-continued

```
Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575
```

```
Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
```

-continued

```
        995                 1000                1005

Val Tyr  Gly Asp Tyr Lys Val  Tyr Asp Val Arg Lys  Met Ile Ala
    1010                 1015                 1020

Lys Ser  Glu Gln Glu Ile Gly  Lys Ala Thr Ala Lys  Tyr Phe Phe
    1025                 1030                 1035

Tyr Ser  Asn Ile Met Asn Phe  Phe Lys Thr Glu Ile  Thr Leu Ala
    1040                 1045                 1050

Asn Gly  Glu Ile Arg Lys Arg  Pro Leu Ile Glu Thr  Asn Gly Glu
    1055                 1060                 1065

Thr Gly  Glu Ile Val Trp Asp  Lys Gly Arg Asp Phe  Ala Thr Val
    1070                 1075                 1080

Arg Lys  Val Leu Ser Met Pro  Gln Val Asn Ile Val  Lys Lys Thr
    1085                 1090                 1095

Glu Val  Gln Thr Gly Gly Phe  Ser Lys Glu Ser Ile  Leu Pro Lys
    1100                 1105                 1110

Arg Asn  Ser Asp Lys Leu Ile  Ala Arg Lys Lys Asp  Trp Asp Pro
    1115                 1120                 1125

Lys Lys  Tyr Gly Gly Phe Asp  Ser Pro Thr Val Ala  Tyr Ser Val
    1130                 1135                 1140

Leu Val  Val Ala Lys Val Glu  Lys Gly Lys Ser Lys  Lys Leu Lys
    1145                 1150                 1155

Ser Val  Lys Glu Leu Leu Gly  Ile Thr Ile Met Glu  Arg Ser Ser
    1160                 1165                 1170

Phe Glu  Lys Asn Pro Ile Asp  Phe Leu Glu Ala Lys  Gly Tyr Lys
    1175                 1180                 1185

Glu Val  Lys Lys Asp Leu Ile  Ile Lys Leu Pro Lys  Tyr Ser Leu
    1190                 1195                 1200

Phe Glu  Leu Glu Asn Gly Arg  Lys Arg Met Leu Ala  Ser Ala Gly
    1205                 1210                 1215

Glu Leu  Gln Lys Gly Asn Glu  Leu Ala Leu Pro Ser  Lys Tyr Val
    1220                 1225                 1230

Asn Phe  Leu Tyr Leu Ala Ser  His Tyr Glu Lys Leu  Lys Gly Ser
    1235                 1240                 1245

Pro Glu  Asp Asn Glu Gln Lys  Gln Leu Phe Val Glu  Gln His Lys
    1250                 1255                 1260

His Tyr  Leu Asp Glu Ile Ile  Glu Gln Ile Ser Glu  Phe Ser Lys
    1265                 1270                 1275

Arg Val  Ile Leu Ala Asp Ala  Asn Leu Asp Lys Val  Leu Ser Ala
    1280                 1285                 1290

Tyr Asn  Lys His Arg Asp Lys  Pro Ile Arg Glu Gln  Ala Glu Asn
    1295                 1300                 1305

Ile Ile  His Leu Phe Thr Leu  Thr Asn Leu Gly Ala  Pro Ala Ala
    1310                 1315                 1320

Phe Lys  Tyr Phe Asp Thr Thr  Ile Asp Arg Lys Arg  Tyr Thr Ser
    1325                 1330                 1335

Thr Lys  Glu Val Leu Asp Ala  Thr Leu Ile His Gln  Ser Ile Thr
    1340                 1345                 1350

Gly Leu  Tyr Glu Thr Arg Ile  Asp Leu Ser Gln Leu  Gly Gly Asp
    1355                 1360                 1365
```

<210> SEQ ID NO 23
<211> LENGTH: 1053
<212> TYPE: PRT
<213> ORGANISM: Staphylococcus aureus -continued

<400> SEQUENCE: 23

Met Lys Arg Asn Tyr Ile Leu Gly Leu Asp Ile Gly Ile Thr Ser Val
1               5                   10                  15

Gly Tyr Gly Ile Ile Asp Tyr Glu Thr Arg Asp Val Ile Asp Ala Gly
            20                  25                  30

Val Arg Leu Phe Lys Glu Ala Asn Val Glu Asn Asn Glu Gly Arg Arg
        35                  40                  45

Ser Lys Arg Gly Ala Arg Arg Leu Lys Arg Arg Arg Arg His Arg Ile
    50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Glu Phe Ser Ala Ala Leu Leu His Leu
            100                 105                 110

Ala Lys Arg Arg Gly Val His Asn Val Asn Glu Val Glu Glu Asp Thr
        115                 120                 125

Gly Asn Glu Leu Ser Thr Lys Glu Gln Ile Ser Arg Asn Ser Lys Ala
    130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
            180                 185                 190

Leu Asp Gln Ser Phe Ile Asp Thr Tyr Ile Asp Leu Leu Glu Thr Arg
        195                 200                 205

Arg Thr Tyr Tyr Glu Gly Pro Gly Glu Gly Ser Pro Phe Gly Trp Lys
    210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
            260                 265                 270

Glu Lys Leu Glu Tyr Tyr Glu Lys Phe Gln Ile Ile Glu Asn Val Phe
        275                 280                 285

Lys Gln Lys Lys Lys Pro Thr Leu Lys Gln Ile Ala Lys Glu Ile Leu
    290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
                325                 330                 335

Ala Arg Lys Glu Ile Ile Glu Asn Ala Glu Leu Leu Asp Gln Ile Ala
            340                 345                 350

Lys Ile Leu Thr Ile Tyr Gln Ser Ser Glu Asp Ile Gln Glu Glu Leu
        355                 360                 365

Thr Asn Leu Asn Ser Glu Leu Thr Gln Glu Glu Ile Glu Gln Ile Ser
    370                 375                 380

Asn Leu Lys Gly Tyr Thr Gly Thr His Asn Leu Ser Leu Lys Ala Ile
385                 390                 395                 400

Asn Leu Ile Leu Asp Glu Leu Trp His Thr Asn Asp Asn Gln Ile Ala

-continued

```
                405                 410                 415

Ile Phe Asn Arg Leu Lys Leu Val Pro Lys Lys Val Asp Leu Ser Gln
            420                 425                 430

Gln Lys Glu Ile Pro Thr Thr Leu Val Asp Asp Phe Ile Leu Ser Pro
        435                 440                 445

Val Val Lys Arg Ser Phe Ile Gln Ser Ile Lys Val Ile Asn Ala Ile
    450                 455                 460

Ile Lys Lys Tyr Gly Leu Pro Asn Asp Ile Ile Ile Glu Leu Ala Arg
465                 470                 475                 480

Glu Lys Asn Ser Lys Asp Ala Gln Lys Met Ile Asn Glu Met Gln Lys
                485                 490                 495

Arg Asn Arg Gln Thr Asn Glu Arg Ile Glu Glu Ile Ile Arg Thr Thr
            500                 505                 510

Gly Lys Glu Asn Ala Lys Tyr Leu Ile Glu Lys Ile Lys Leu His Asp
        515                 520                 525

Met Gln Glu Gly Lys Cys Leu Tyr Ser Leu Glu Ala Ile Pro Leu Glu
    530                 535                 540

Asp Leu Leu Asn Asn Pro Phe Asn Tyr Glu Val Asp His Ile Ile Pro
545                 550                 555                 560

Arg Ser Val Ser Phe Asp Asn Ser Phe Asn Asn Lys Val Leu Val Lys
                565                 570                 575

Gln Glu Glu Asn Ser Lys Lys Gly Asn Arg Thr Pro Phe Gln Tyr Leu
            580                 585                 590

Ser Ser Ser Asp Ser Lys Ile Ser Tyr Glu Thr Phe Lys Lys His Ile
        595                 600                 605

Leu Asn Leu Ala Lys Gly Lys Gly Arg Ile Ser Lys Thr Lys Lys Glu
    610                 615                 620

Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
                645                 650                 655

Met Asn Leu Leu Arg Ser Tyr Phe Arg Val Asn Asn Leu Asp Val Lys
            660                 665                 670

Val Lys Ser Ile Asn Gly Gly Phe Thr Ser Phe Leu Arg Arg Lys Trp
        675                 680                 685

Lys Phe Lys Lys Glu Arg Asn Lys Gly Tyr Lys His His Ala Glu Asp
    690                 695                 700

Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Glu Lys
                725                 730                 735

Gln Ala Glu Ser Met Pro Glu Ile Glu Thr Glu Gln Glu Tyr Lys Glu
            740                 745                 750

Ile Phe Ile Thr Pro His Gln Ile Lys His Ile Lys Asp Phe Lys Asp
        755                 760                 765

Tyr Lys Tyr Ser His Arg Val Asp Lys Lys Pro Asn Arg Glu Leu Ile
    770                 775                 780

Asn Asp Thr Leu Tyr Ser Thr Arg Lys Asp Asp Lys Gly Asn Thr Leu
785                 790                 795                 800

Ile Val Asn Asn Leu Asn Gly Leu Tyr Asp Lys Asp Asn Asp Lys Leu
                805                 810                 815

Lys Lys Leu Ile Asn Lys Ser Pro Glu Lys Leu Leu Met Tyr His His
            820                 825                 830
```

-continued

```
Asp Pro Gln Thr Tyr Gln Lys Leu Lys Leu Ile Met Glu Gln Tyr Gly
        835                 840                 845

Asp Glu Lys Asn Pro Leu Tyr Lys Tyr Tyr Glu Glu Thr Gly Asn Tyr
    850                 855                 860

Leu Thr Lys Tyr Ser Lys Lys Asp Asn Gly Pro Val Ile Lys Lys Ile
865                 870                 875                 880

Lys Tyr Tyr Gly Asn Lys Leu Asn Ala His Leu Asp Ile Thr Asp Asp
                885                 890                 895

Tyr Pro Asn Ser Arg Asn Lys Val Val Lys Leu Ser Leu Lys Pro Tyr
            900                 905                 910

Arg Phe Asp Val Tyr Leu Asp Asn Gly Val Tyr Lys Phe Val Thr Val
        915                 920                 925

Lys Asn Leu Asp Val Ile Lys Lys Glu Asn Tyr Tyr Glu Val Asn Ser
    930                 935                 940

Lys Cys Tyr Glu Glu Ala Lys Lys Leu Lys Lys Ile Ser Asn Gln Ala
945                 950                 955                 960

Glu Phe Ile Ala Ser Phe Tyr Asn Asn Asp Leu Ile Lys Ile Asn Gly
                965                 970                 975

Glu Leu Tyr Arg Val Ile Gly Val Asn Asn Asp Leu Leu Asn Arg Ile
            980                 985                 990

Glu Val Asn Met Ile Asp Ile Thr  Tyr Arg Glu Tyr Leu  Glu Asn Met
        995                 1000                1005

Asn Asp  Lys Arg Pro Pro Arg  Ile Ile Lys Thr Ile  Ala Ser Lys
    1010                1015                1020

Thr Gln  Ser Ile Lys Lys Tyr  Ser Thr Asp Ile Leu  Gly Asn Leu
    1025                1030                1035

Tyr Glu  Val Lys Ser Lys Lys  His Pro Gln Ile Ile  Lys Lys Gly
    1040                1045                1050


<210> SEQ ID NO 24
<211> LENGTH: 36182
<212> TYPE: DNA
<213> ORGANISM: Homo sapiens

<400> SEQUENCE: 24

gtgagcgcag ccgggcagcg cctagtggat tacagcagac gcccggaccg accgccgcct     60

gtagctcggc agccttcggg taagaatcgc cccctccccg ctccccagca tgccaccaag    120

aagcctgggg cgccgacccc cttgggcagc tcagtccggc tgctccccta catttcccgg    180

ggaagtgggg ggtcgctgtc taagcccctt cccccaatca cttcgttcct agggcgtccc    240

ctggggcctg gggtggagtc cggctgggtt cagaagtcta agggggcagt attatttcaa    300

aaattctgag atacgggtag ccacagacag gatcccactg cctagatgga gagcccctca    360

atcctaccct aggaaagtgt atagacgggt tactactgaa catctccact ttgctggggg    420

tcactaaagg cattttatat agagctgtgg tttttgtggt ttacctgtgg ccgtggccag    480

aggttcctgg gaggctaaca ggtgtttttt gagggttggg gcttgggtgg gggtggggtg    540

aattctctgt ttctaggatg tgcttggtgt ttgaatctag gctttagtga ctgatgctgg    600

ttaatttcta gggttgatgg tttattgggc cttgtgttgt atgagatgga attttaaata    660

tttttaaatg tttctctagt tcttagagaa atttttaagc aactcaagat aggctcttcc    720

cgcatatgat aatccgtcag gtgaatttgg attcttttat atcacaaaat gaatccatgt    780

tttgggaggt aatggtatca gaatatatgg tgcaggtctt ggtaaaaacc caatagatct    840
```

-continued

```
ttgagaaata caagacatct ctgtgttgaa acatcgtgtg tttcttattt gccagagtag    900
gaaaagagta gatctttttg ctctctaaat gtattgatgg gttgtgtttt ttttcccacc    960
tgctaataaa tattacattg caacattctt ccctcaactt caaaactgct gaactgaaac   1020
aatatgcata aaagaaaatc ctttgcagaa gaaaaaaagc tattttctcc cactgatttt   1080
gaatggcact tgcggatgca gttcgcaaat cctattgcct attccctcat gaacattgtg   1140
aaatgaaacc tttggacagt ctgccgcatt gcgcatgaga ctgcctgcgc aaggcaaggg   1200
tatggttccc aaagcaccca gtggtaaatc ctaacttatt attcccttaa aattccaatg   1260
taacaacgtg ggccataaaa gagtttctga acaaaacatg tcatctttgt ggaaaggtgt   1320
ttttcgtaat taatgatgga atcatgctca tttcaaaatg gaggtccacg atttgtggcc   1380
agctgatgcc tgcaaattat cctggatcac taactctgat cacttacaaa taagaaactt   1440
gagtgattgt tattttattt ggagtgtttg tattttgtaa ttatttctct actacagtac   1500
aatgaccttt gaggtcattc tttgatcggg gtaaaaaaca ttccccattg aaaagcaggc   1560
acctggatag tggcttctag gccctgccag gtagattcgg agcaggaaga gtccctaggt   1620
cggatggtac ccgggtgggt gtgggggtgt ggccctgatg gccaagctct atgttcagag   1680
cttcagtgct tttccctggt tctgtagcac agcgcgcttg agtgactaaa aacctgggtt   1740
gggtgcaggt ccgattacgc agcagaggtt gatgtcatgg gcagatttgg aagacttgag   1800
gggttctttg taagccccgt ggtagcatta attcttattg gaacgaaatg gtcgattgca   1860
tctaagggaa ataatccaca aatcacagga actctcgggc cattagtcca caagaaaact   1920
agttcgtgct gttgccacta ccggaaataa ccccattgtt tctgttaacc taaccaaaaa   1980
atgaaacgaa attttaaaac gctgggaccc tgagagctga gaagcccaga agtataactc   2040
ccagtgtcct tggcccaaac ctctgttctc tcatagatca gggagccgat agcatgtccg   2100
ggccttggtg acgacgggtc aggccatgaa ctgggcttga gatctctggc gaggaccagg   2160
agaaagacga agctcgaaat tataaatgtg gccaagcacg agagctgaaa acaaagcgta   2220
ttttcccgtc agatgtttct acaaataaat ttcgccagag ttctgttttc tgaatcagag   2280
aggcaaggga aatcgaacaa agacagtatt tcaccctggg ctggcaggca gctgttagag   2340
gtatttacgg ccttgccgca gtgcggcggc caggcagccg ggtagggtat gcgggggcac   2400
cggaagctgg ggagaagcca tgaagaactc agaatttcaa cttaaattca atttagggtc   2460
acgttttcgg aaatggcgtg aacagatgcc ctctttctag ggactggtcc tttagacttg   2520
atagttttgc agaatgaggg agaagttgtg ctctctggat gtaggatggt tttccccgcc   2580
ttgaagaacg actcaaaggg aagcggtgcc caagatgtga catttctgat ccacataaca   2640
accttcagag tgttcattgg caacgaggag atgctgcttg ttcggcggaa tagggtttgc   2700
aaatcagaaa ggacagttga agcttttaat acatgttttc ctgaaaaaga aaagtgtgtt   2760
tcctgcttct tgagatgagg ttcccaagct cctctgcatc caggcgtaga agcagtgcgc   2820
ggtaccttat ccgcactgcg cggtgcaagc cggccgcaca gctcacggtc ccgcagcgcc   2880
cgccacacac ccgcgccaga ggtccagcgc atgtgcagtg aaatggccta gcccgggaat   2940
tcgatcggca aagcacgggt gtgggggcgg gggggtgggg gggggcgagt ggactcgagc   3000
aggaagatac acccgatctt tccattctcc ctccgtcaag gctcgctact catcttgcct   3060
ttatctcagc cttccctgta tagctgaaca gttctacctt tggctacatt tccaatcatt   3120
atgacttatc acctcacccc agtttaaatc tgtacgctag acataggctg aaaatacgag   3180
acgagggcca aaggaaacac tcttctttcc agtttatata tatatatagc atatatttgc   3240
```

```
ccctcgggga aggctgtaga tttttttttt tcagcctgct gctactactt tgggaaaagg   3300
ccttttctcc tggcgcctgt tcaaaccgcc acacttcagg ccaatccttc ggcctgacca   3360
ttcccggatc ttgttatgcc agcacagcac attcgagggc tctggggggc agcagctcgg   3420
cgaagagcag tcaaataaat aaataaataa acaaataaat gaacggacat ataagggctt   3480
ttcccgcctg ggttcgctta aataatgggg gacaagcgcc tctgggccac gagcttgttg   3540
tttgtcctgg gatggggggt aggggatgag aggtggcctc aggtccctct tgctccttcc   3600
agccgcccca ggggacactg tagaaccagc ctctggtgcg gggagacctc cgcctgccgg   3660
aggaagtccc agcctcaggt ttccggggct ggtggtctcc ctgctctgct gtctggcgcc   3720
tcgtccagga ggaggcgctg taggacaagc gtctcgccgg ctgcggcggg ccggggaggg   3780
cgggagcgga gggatcggta cccgctcctc ccttcccgcg cactctacct ccgcgcgcca   3840
agtgtgtggg gcctcgaaca agggtcgacg gtgctgcgcc ccgtccccca aggggttcct   3900
ttccccagac tggcagtgga agcagctccg aggcctggga gcctagggcc gttccgggtt   3960
ggcgggccac ctcgctttct ccgcgctccc ggagggggcg cgatttcctc gtgctgcgct   4020
tgtaggagca gcaacttgaa tcctgtgtgg ggcaagctgg gcccaatccg cggatcccaa   4080
ccagcccctc ccgctgggcc gtgggtctcg tcatttacct tgcccaggat tcctggtacc   4140
cagaatggac agccttgaaa agcacatcct ttagtgcctc ctccaacagg ctgatgggcc   4200
ttgcccttgc tcacttagaa caggacctgg gtcctgggac tccctggaga ctcagagctt   4260
gggtaaatcc catttgctct gcagctcaag agaactagcc agatgcgcat gtctactcca   4320
caccacccaa ccactcttct atcaccactt cgctcatttc aggccttttg tgggctccac   4380
tgggcactcc tcgcaccagg ttcaagagcc agcgacacct tacttaaata atgctctgac   4440
ccaatcccac tgatcctccg ttatctcttg gcaatgcagt cttttgtccc cctctcccca   4500
ccgccttctc tagggtaatg attctcagtg aagacctgca tcaaatctct tgtttataat   4560
gcaggtttct gggtcctatc ccagacctac tgaatcagaa tatccagata tggtacccag   4620
agacctgcat tttgtaaaca ctcctccgcc cagggcactt gggctgcata cttatgtttg   4680
agaaccactg gtcaattatc tctcctgctc cttttatgat cctttgttct ccaaagatca   4740
agttccctct aaccctacaa ctaagcatcc cccagagctc ttagggttcc atccagggtt   4800
gtggttttta aggtcaccac cctatagact gaatacttac attttaggga agaggccgtg   4860
gatcccttaa cttttggctt acagatttca aagacagcag gttgtgggtt cagactgcca   4920
tggtaccact tacctattgc gtgaccttag gcgagtactg caactctcta gacctgttaa   4980
tttctttgaa aaggagggat aagagtacct tcaagggttg ctatgagaat ttttacttac   5040
ttgcaattct atatgtcagg cactattcta actgctttat gtacctttaa ctcactggtt   5100
aagtacttaa accagtgttt tgccacatac caagtattca atacatacat gtttcttatt   5160
atcccccttt tgctgagtaa tcaggcctag acttttagag caaaagaccc ctggttcact   5220
caccaaattt ttgaattcta tggaggagaa gacaggcttg aacacacagg aagtagcaga   5280
ctcaggagaa catagttccg tgacttaacc tattgctgtt gtgggccaca tagtcctggc   5340
ccattgggtc tcagtgtctg gcacctaaat gtatcagggt tacaccaggc agaaagtggc   5400
cctaactcct cagtgggcag gtatcaggta ggggaggcct cacattcaca caggcacatc   5460
ttcgactccc acagatggct tcaggtcttt cctgagagca ggcccattta tccagctcct   5520
gcaatcacct tctccatcac caccctgtcc tgtcagtcac acccactggg ctggttgttc   5580
```

-continued

```
ctcttgttat tctatagccc cagggcaagg accctcctta gtcttttaaa atctagggca   5640
gggtaggaaa gcaaaagacc aacaacagcc aaggaagccg aggagcccca cctccactcc   5700
ccccaaccct tctcacccct ttaactgctt gtgccccagg atctgggttc cagggcagca   5760
gctgagcctc tgcccccaac atgtgtgggg gttgtagcca gaaagggtat ttttataact   5820
cttcataaaa gatgtacgga atttaaaaga attggaaggg tcaatggaga attgagggat   5880
aagtcctcac ccttagttct gggtccatga cttctggcta cagacttttt tcatgagaga   5940
cttagtagct cttggccaag ctgctttgct tggcttaacc aggaagtcct cctgggtcag   6000
attttccctc aaaacgtaca gtttcttctg ctaccaacct tgtcaggcag tgttctgcct   6060
acagcctagg gcagcacctc ctgttccaac aaatcttggt tctcctagta cttaggtagc   6120
caccttagcc tcttctgccc ttcttgggac cactggagcc ttatttctag cctccgctct   6180
gctctcaaac atcttgctcc aagccccctc ccctttttgtt ttggtctctt ctctcactat   6240
tggccttttt gtctggggtc acctctgcct ccctgggtcc tcaagccaga gctccaatga   6300
gtgactccac tggggcagag ggaagtgggc agggagagaa atgtttctgt tttggtgata   6360
gagtatagtg ccaggaatat agagttatgt ttctctcatg ctggggactc cctgttcagt   6420
ccttctctgg ctataccccc agactacgtc cttaagtacc agccctgggc agtcttcttt   6480
ctccacctgc cccggccagg tattcaaagc cccacctatc tcttctggtt gtacaaacat   6540
ttagtttaag aggaaagctc caccccccctt taggcaaaag gcctcttaag agccaaaatg   6600
agaatattct ttcctggagc cacctagcag gggcccttag ggtgggcaga gggctgactt   6660
tcattacttt tggagtagag ctgcttcctc ccgggacccc ttcactctct cctccttcct   6720
gcgagctact ttggctccca gggtttggag gagccctaca aggtgcccta tctcatggga   6780
gcttcctagg ctctttttag ccacatgggg aaggacagta cctacagtcc cactttacct   6840
ataaattaat tccttctagg tttttaagaa ggctcaactt gtctttcccc actgcctctt   6900
ccattatcac cacaaccatt gcaagttctt gggaaactcc ccaacaaact ggcacatgct   6960
agctctgctc tttccaccac tcagcttctc tcccccattt caccctttct ttcatctaca   7020
gaagaccagg aggaggggag gagaaaagga ataggggaag gaggagacaa aagaagatta   7080
tgagaaggtg gacccttact ctctctttaa tcactttgcc tcgctttcct aagatcagga   7140
cataaatgat gtctgcctca atatattcct ttcgtctctc cttttcttta ctcacagcta   7200
cttttccgtt attgtctaaa tatacagagt aggctatgta attttatctt tttgtgtagg   7260
ccacaataaa ggttgcaagc atgtctcagt caccatgctt catcaccgtt tgttcaaaga   7320
atgtctacct agccctaact gggtacccat cactgtttca aacactattt ctcctcagtc   7380
ttatcttctc gttaccccat tctcataaaa agctcatcac aattgcctgg aaactaatat   7440
gtactatgat taatttcttt ctttcttggt tttttttttt tttttttttt gagacagatc   7500
ctagctctgt cgcccaagct ggagtgcagt ggtgcgatct cggctcactg caacatctgc   7560
ctcctgggtt caagcgattc tcctgcctca gcctcctgag tagctgggat tacaggcacc   7620
cgccaccaca cccggctaat ttttgtattt ttagtagaga tggggtttca ccatgttggt   7680
caggctggtc tcaaactcct gaccttgtga tctgcctgtc ttggcctccc aaagtgccgg   7740
ggttacagga aaataaagaa agctcttctc aacccctcaa actattatta ttattttaca   7800
gctgctcatc tagtgctaac cagaatcaga aacatgtttt gaagagttta tccattttta   7860
aaaacagatg ccatcaacca taaaagaaaa atatcttcct acatggctaa tgaaacaaaa   7920
aaaggagaaa tggatgcctt acaatccagg ctaatagccc cctgctttct agctaatgac   7980
```

-continued agtgaaatca ggaaatgggt ttgaaaatgc atgtagaatg ggtggaaatt gggatgcaaa 8040
gagatctttg tatgaaggga tctcttttat gggcttgatg ggtctttctg atgggaacag 8100
ttgcaactga atttgattta gaaatcatat gtgtgtgtgc tctacaaatc tccacagaac 8160
atccattatt ttcatcagaa tagtcaaaac cacacgtttt tacactgttt ggtggcaact 8220
ctggtgggct attgaagggt gctggggggt caattctctt tttatttatg ctccttggtg 8280
ggagctgagg gcatctttcc ctctctctta cccccacccc agcctccccc aagcagagaa 8340
tgccacattt tcctagagag cagcttcagg cccaagctct ttccttggct ttctcagcag 8400
gacagcggca gtgtactact ctctcttcct ctcttaggct ctctccctgg tgggggcagc 8460
agtgtgggtg tgggggtagt gctcctaaaa ctcccaccca gttttgagcc cccaaagttc 8520
ctgagcctta atcactgtgc ttggagacac catgggagtg gggacatctg acttcctagg 8580
cttggattcc ttgagagtct catttgcttc ctcacaccct gtcgccttca caccagggct 8640
gttttattgt tttataacct tctttggagc tttagttgcc aaagattcta atgaggctat 8700
tctccacttt ctcactttac caaaccccaa gtcttgctgt gttaagcagt ttggtcactt 8760
gcaaaggctt tcctttcaga tctaagcgaa ttacagaaac ctctaggcat gtggctacct 8820
tcaactttgt ccaagcccat gcacaacaat atggagggag ccaagtgtta attccaactg 8880
ctactcccac ccccaaaccc acccagcctc tccctaacca ccctttctcc attgaaactt 8940
gaaaaaaatc tcaaataact tccaacttct gtcataagca aataagaagt ggcttttgac 9000
cttcctcttt atcacatcta gagctagaaa attattgaaa taaaggggtt gatggtactc 9060
acagtgaatg ccgccaaaga atcataagac atgcccacca actagccttt tccaaatagc 9120
actatctccc aacttaaaca gcttctccga aaagatgcta tttgaaaagc ctggggtatt 9180
gatatgaata tgacctccct tgcatcctgg atatttggaa ctatttaaat ctgaggtaac 9240
cgttgcagcg aacctttatt tagtgaataa aagtttaaag ccaaaggtta tttatggttc 9300
tgcagagatg ggacctgagt ggctatttac gagcacgtga ttccaataaa ctttgtttta 9360
tggcttgaga gttgacaagc caaaatataa ttcccaccat aaattaggtt aagagcatac 9420
aagtgcagat gctgggttcc tggagcagca ataggaacgt gagaggctcc agccagctcc 9480
aggctaagaa ggagacggtt ctactcccag ctcccctgcc cactaggaaa gaaaaacagt 9540
aagtcactta ttactttttc cacaacaact tcagaggtgg gagatttctc tgttcctgac 9600
ttttctgcct aggatgggga taagtctcat cgaagttaat tctaatttta gcctaaacct 9660
aaattaacaa atagaatgag catctcgatc tcccatgccc tcccttcctg atagggacag 9720
ttaggaattg agggctctca cctcacaaga gggacttact gcccctctcc tcccccttaa 9780
gagcatctcc ttcagaagtg gaataaaaca gtggtattct gggtggggaa agaaagagag 9840
gatgagggtg aagctgcttt gtccctgaga tttctgatac tgctttccta taataatatc 9900
aggaaagact gaaaacttaa aactggacac cagcctctgg gaggaccact gcttagtaag 9960
attgtcttct gggctctcca gcagcaatcc tgaaaaattg atgtcatacc catagagctg 10020
gataacaatc taaagcattg ccattcacct ttaaacccat tgattttcct cctccttggt 10080
tatcatttgg gtcctcattt ccccctggaa attgctcttt gttttgaatt ggagtagaag 10140
tggcaagtcc cagccatgcc tgattcttct ttgaagagga gaagacaggt tttgggggca 10200
ctggttgggg ctgaggaatt tgaaaccaag ctgaagctgg aaagggaggc tgaattgctc 10260
ccagggtggg agagatagga agcaggggtg aggggcagat ggagcggcta ccccctcccc 10320
agtggacctg cacccacccg gcccgattgc gcagaaggaa acacacaaag gcccattttc 10380
tcctcgcttc tcgttttccc actgggaaaa ccctgttaca ggcgacctga ctcgggccca 10440
gtaactagtg aggttttgcc caagggtgcg tggagtgggg gaggcgatgg agatcgaaat 10500
ctgtcataat ccgtggctct gctcttgagg gactgcggtc tccggctctg cggagaactt 10560
tgcgcagttc ccgggggcgg gcacctgaag cagggaggtc tgggtattgg tggggtatct 10620
gggccttgtc atttttctgt gtgttatatg tgtctgcttt attatcctgt ggaatttaag 10680
tgatccccgt tttcattgca acaggttcag gaccatgaga gagcgccgct gtaagtacct 10740
tcccgcttct tccgaatcgc gaagagacgg tactgatcgc ggggaagtgg tgggctaagg 10800
ggccaagcca gcggagtggg cggatagaag aaaggccctg cctcccccac cccacccccca 10860
ccctccaccc ccggcctcgc tctgcgaggt tagcccgctt cgggaggtgg aggcgctaaa 10920
tcgaggtccc ggaaagcttt tctggggcct ggttcacaga cacctgcctg agagaacggt 10980
ccgcggggtc tcgcccttgt ctccttgggc ctccctagac cttcgcggcc cttccctgct 11040
ctgcacaggt gcagctccgc caaggcgctc acttctgtta agagcttgct aattagcagc 11100
ctgtcttatt agcggcttca aaccaacgca gtaaacacca aggcaatgcg gtcccctccg 11160
cagcccaacc cttcttaacc tggtctagcc tggccaacct tctgttttta aaaaaattca 11220
ctgaaaacaa aaactcaatc ctctgtggcc gtgggtgtgt tgagttgccc gcttctgagc 11280
tttatgtgga cattccttcc ccgcccctcc cccgatctgt ttgcagcggt gtgggccctg 11340
ggcttgggac actggctgag cgaggaggga tacggacctt cttttcacct ctgcttctct 11400
gtaactgcag ttggagaatt tccgccccag aggcgctggt gctgcaagga ggcataggag 11460
ggtggagtgg ggtggatgcg gtggggtggg gccagagact cgtgggatcc ttggcttgga 11520
tgtttggatc tttctgagtt gcctgtgccg cgaaagacag gtacatttct gattaggcct 11580
gtgaagcctc ctggaggacc atctcattaa gacgatggta ttggagggag agtcacagaa 11640
agaactgtgg cccctccctc actgcaaaac ggaagtgatt ttattttaat gggagttgga 11700
atatgtgagg gctgcaggaa ccagtctccc tccttcttgg ttggaaaagc tggggctggc 11760
ctcagagaca ggtttttgg ccccgctggg ctgggcagtc tagtcgaccc tttgtagact 11820
gtgcacaccc ctagaagagc aactacccct atacaccagg ctggctcaag tgaaaggggc 11880
tctgggctcc agtctggaaa atctggtgtc ctggggacct ctggtcttgc ttctctcctc 11940
ccctgcactg gctctgggtg cttatctctg cagaagcttc tcgctagcaa acccacattc 12000
agcgccctgt agctgaacac agcacaaaaa gccctagaga tcaaaagcat tagtatgggc 12060
agttgagcgg gaggtgaata tttaacgctt ttgttcatca ataactcgtt ggctttgacc 12120
tgtctgaaca agtcgagcaa taaggtgaaa tgcaggtcac agcgtctaac aaatatgaaa 12180
atgtgtatat tcaccccggt ctccagccgg ctcagcaggc tcccccaatt tgtctggata 12240
gagcctaggc ccagtgtccc aggaaggtgg atacttggga gtctttggca ttcagggaaa 12300
ttggggggac tctcctggga taaacagatt ctgcagcctc atagcccttg ttagaactgg 12360
cgcccccaaa atccctacga aacaggtaaa gtggtggaag caaaggatgg ggggatgagc 12420
aaagtgccag gcttggaggg ggagtatccc tgccccaccc caccaggccc aggcccaggc 12480
ttgaaactaa attttgaatt atgtgggagg taggaagggc aatcaagaca gttaaaaaaa 12540
aatctaacac cttcagccta cagttaggca ccccaaaagcc ccactcgagc cagggcatcc 12600
ctgtgcccct gaaatccatc gaggctctga gtgagtctgc gctctccatg ccctgaactg 12660
agggacaagc actgcacagt gccgaggcgc tggggcgggt gaaatttgtg aacttttgta 12720

-continued

```
ctcttgtgtg ctgctgtcgg caaagcaaaa ataatgaaag tttgtgatat gtttgtaaat  12780
gatttcgaat gacccctcgc cctgcccttc accattagcg cgccggcctc agcccaaggc  12840
ggctcggtgc ctgtgagcag cgcctgcctc ggggtctgca gcagcagcgg aacggagagg  12900
ccagcccgga tcagggccca tgaaggtaaa tgcgcgactt cttggagaag tagctttggc  12960
agacaacctg gcttggtcgg gcagtaggaa aaggagtaga cacaggatat tcccctctcg  13020
cttctttttc ttctgccgct gagggcattt gttcctttct ggaaaatacc acttggtaag  13080
gaggagggtt atttggatcc tggtgggggga gggtggttaa taaagccgcc atccttggga  13140
tggattattt ttctttcttt ctttcttttt ttctttctta agaagaatat tctggttgtt  13200
cgcctgcttg gtaaccctga ccctggcaga agaatgaggg aactcattgc ttcaaattgt  13260
cgccaagccc attaggctac ctgaactgtc tcagaaagtg cgggtggctg cgtcgaacgg  13320
tggtggctca gaggaagaga ttggggccgg cagcgaccta ggtacctcac tctgggtggg  13380
acccagaggt tgtaacgttg tctatatata ccctgtagaa ccgaatttgt gtggtatccg  13440
tatagtcaca gattcgattc taggggaata tatggtcgat gcaaaaactt cacgtttctt  13500
cggaatagcc agagaccaaa gtgcgacatg gagactagaa gcagccggcg ctggtcagcc  13560
gcctcgttct gttttattac cttggactcc aggaggatca gctgcgcctg gtgacataga  13620
gcagcttttc ctctccagaa gctcctcacc tttaaacaga gtatcctctg ggtgctgaaa  13680
agaaagaaag acagaaagag agaaagagag agagagagag aaagagagaa tgcaagccta  13740
attggttgca tggatgcagg gccaaagggc taggttttgg ggtactaggg agtgaggtac  13800
aaggccagct tgcccagtcc cagctctgcc ctccaggaac atgaggtgca aaggtaccca  13860
aatgggggct tgcttgtatt tggggcctgt gggaagaaag caagcttcaa agaagcccag  13920
tggggagctc tagggtgcat tttgacaagg tggaggtgcc cttgccacca tcccagccca  13980
cccccagcta catgggcaag ggcagcgagg gccccctgct attttggcag ggcccagctt  14040
tggctgggaa cccccgggcc tgggcactgg tagaaagcat ggcggttact cattgcctaa  14100
tttgattcaa gctggccaga ttctggtaac ttttgggtga ccctgatgaa gacaaagcca  14160
ggacggcggc ctttgtatgg cagaatccct gctcccgccg gctgcaggca gggcgggcag  14220
gcaggaaccc tcctcgcctg gggcactctg cccaactcag aggcgagttc acccacccac  14280
ctttcattgc tctgtacccc aataggagga ttcattctcc cttgagctgt gcctacttgg  14340
tgtcgggggg cgggggttgc attcagctgg gggtgagtgg aagggccacg gaaggttggc  14400
aaaatcagtg gcagacaaaa gctgggatta cctgagggga atggggtgct ggggactgga  14460
actacattaa tatctggcag gggctctcaa atgtgccata gcaagctact tgattacacg  14520
tatgttattt agttaaattt gtgaaaatta tgagatgctc accaacccgg tgataaactt  14580
gctccctcgc cattggctgg cctggtcaca tggctgccca actttattca gttgacagca  14640
agtaggaggg ccctatggaa ggagaaaaaa agacaacacg agaaaaatta gtattttcta  14700
ccttctgaaa ttaatggtca tgagttcgta tatggtgaac tccaagtatg tggaccccaa  14760
gttccctccg tgcgaggagt atttgcaggg cggctaccta ggcgagcagg gcgccgacta  14820
ctacggcggc ggcgcgcagg gcgcagactt ccagcccccg gggctctacc cacggcccga  14880
cttcggtgag cagcctttcg gaggcagcgg ccccgggcct ggctcggcgc tgcctgcgcg  14940
gggtcacgga caagagccag gcggccccgg cggtcactac gccgctccag gagagccttg  15000
cccagctccc ccggcgcctc cgccggcgcc cctgcctggc gcccgggcct acagtcagtc  15060
```

-continued

```
cgaccccaag cagccgccct ccgggacggc actcaagcag ccggccgtgg tctacccctg  15120
gatgaagaag gtgcacgtga attcgggtaa ggctagggtc cagtaacctt tctgtccaca  15180
tcccagcccg ttagcctggg tcctctggaa gggggtgcga gtaggtgggg gcgtgtggag  15240
cttccatggg cgccgcaatt actctcccca taaattttta tagctgaggg agcaggtcag  15300
gaccatgtgg ctggctgctc ggctgtgggc gcaaaagggg gtggggatgg gggggtgggg  15360
gaggactcca ttttcagagc agggggaagg ctgtggagga gcgggggatt tccaaaatgc  15420
ttgagggttc cggacctggt ggtgggccca gaagaaggag cacatttggg gatcccgcaa  15480
gcctggggta tgtgggtgtg tttgaggagg tgggtgggag tgagcgtgtg cgccggggag  15540
agggcgggag ggaggaagca agcgagcttg ggagcgcgcg gggagggccg cgggcctcgg  15600
ggcgcgccag gaagtgagcg gcggaggcga ggggcctaac tagtggccgg gcgctgacct  15660
gcctgtcctg tctgttttgt ctcgcagtga accccaacta caccggtggg gaacccaagc  15720
ggtcccgaac ggcctacacc cggcagcaag tcctagaact ggaaaaagaa tttcatttta  15780
acaggtatct gacaaggcgc cgtcggattg aaatcgctca caccctgtgt ctgtcggagc  15840
gccagatcaa gatctggttc cagaaccgga ggatgaagtg gaaaaaagat cataagctgc  15900
ccaacactaa aggcaggtca tcgtcctcat cttcctcctc atcttgctcc tcctcagtcg  15960
cccccagcca gcatttacag ccgatggcca aagaccacca cacggacctg acgaccttat  16020
agaagtgggg accctgggcc catctctccc tgcgcaccag gctgagccga agctgcgggg  16080
gcaggccggg cctgctgtca cctcgctggg ctctaaggta ctgtggggtg gacctgggac  16140
aagcaggccg ccctcggact aggttagcat cctgcccgag ggcagccccc tccctagagc  16200
gggatgggga tgggaggggg ggcgggattc tctctctaag tatattatat ggcaggagct  16260
actgagaaca taaaatcttg gcgagtcatt aaacttatga aaatcaccgc tcttggattt  16320
tgaatttgca aatgaaggtt ggatgcttta tcccactgtg aatttggaca ttctccccca  16380
ctccacccct ccagggtgct ttgtggctta ataatgtggg ggagttgagg cagaaggttg  16440
gccacccctg tgctaggtgc tttcagtgga agccagagag ctgggtcagg atttctggac  16500
tttctgggtt gtctatggaa tttcatgtga ttaaaaaata tatattttgc tcccagtggc  16560
cccacctcca aagaaatggg tctaagaagg aagtaaaaat gggttatttt atgtttagat  16620
atttgcttaa atatttattt gttgggaaat gtggtacaga aataactgac accttcatgc  16680
caaaaatctt aaaaaggtga aaggggctga acttcaggga gcagaatcag agatatgtgc  16740
acttacttct gaactccacc cctccccact ctctggaaat gtatataggg gggccttaac  16800
ccttccagaa ggaagcaaag gattcactca aagttgcatt cttgaaaata tatttccaca  16860
tgtgtttttt tcagcactgt gcttacaacc agttctgggt gattaaagga aagggaaaaa  16920
aaccaacaaa tggtccaaca ttttccttct ggggaaagaa aacaaaacct ctatgcactg  16980
ggtcattaga taatgactga attttctgtt ccaactggat tccaaatgcc ctaaataccc  17040
tcatatagca gtgttttaca ggaattagtg tatggcctgt gtaggggagg ggctgtgcag  17100
tggggagaaa gtgggaaggt gaggaactct tgctttaaga aggaaaaaaa aaaaaaccta  17160
attgaatcta gaagtccaca aaagttagcc ttagagtttt tttccccctg aagttttaat  17220
ttttttaaaa accaaatcta aggaagtttt cctcagctca ttaattagaa gcagaatttg  17280
taaaagtata aaagttttca agcactcgtc tttgccttga gaatagtggt tttttaaaga  17340
atcactctca acaggggaga tgtcctctag tcgtttttct tctgcctctc ctgggaaggg  17400
ttcaaagttc atttttctaa aatgctgacc ctcaagcata aggaggaaga agtcaaagtt  17460
```

-continued

```
aatggccaga gttcatatac tcagatgaaa ccagtcttcc caaggcctca ggctccaaaa  17520
aaggttgtag ctatcaaaaa gtgaccaaag tgggaaaggg agaaaggata agcttaaaat  17580
ttaattttaa gatccagaag gggggtattt ttttcagtac ttcaaaaaca ctttagaagg  17640
tttctgttgt aatttaaaaa atatatttaa gtgggaggga aaaaagagtt tctctgtagg  17700
cttgttcttt ggctgtgtct cctgagagct gagggcaggt attcactgca gtccctaggc  17760
tgaaattccg cttctctgaa gtgtcttcca agccttggtc ttttgtatta gaccctgggg  17820
actgctcttt gtttctcctt ggggtgagcc tggctctcag acttgcacat ggcaatactt  17880
gaatgtcacc acgtcgggat attaaagatg gatattcgtg cattattcac atcattgttt  17940
ctatgacaaa aagcacagag ttcatacata gtcaagacgt ctttttctg acgccctcac  18000
gttgagaagc tgaaaaggta ttttaccgaa gttcgggtaa attacagaat caggttcatc  18060
cagaggacaa attttctatt tgattagctg tatttcagcc gggaggactg acctctaaac  18120
ccctaacctt ttggactcta actacccttc tcttctttt tcctctctaa catggagagc  18180
agtctttgga tgtaccattt gaaaggagcc gctatcctta ggcaagttgg aaagttgcta  18240
agctgctttc ctaaaaccca aatctgtcta tacattgaac cttctctttg agaaggggaa  18300
aaaggtatat attttcacaa catccaatta catatatata atagagattt gttgtataga  18360
ttttccccca cctcagaagt tcaggttact cacccccagt ttcataccaa atgccacaca  18420
ggcttaactg actgcatccc tgccccagag gaaagccaag aaacatgttt tcatgaggaa  18480
aacccaagct ccttctcaaa catagcccca ctactttgga aagtaactta atcagagaaa  18540
caacttcttt gtttataagt ctcagctctc cttctcagct tggagggatt cttttgaaat  18600
gttaatggag cctggatggc ccagagtgca gcccccaacc ctgaggtccc agtcggaccc  18660
cagcatccat ttgggcccac aggagtgggc cagggaaggg gtagggcccc gtaaccactt  18720
agggcaggga aggaaatggg tttccatctg agaacgtgct ttggagaaag ctaggtgtgg  18780
aaaagctcca atgcccattt gctattattt gtttccagtt tgttccttta aatatgagcc  18840
agaagtgttt gtgttggtgt tttaaaaaca aaaacaaaaa ccgtgttggg gtcctgactg  18900
ggggaggggg agagtgaagt gtttgctgag gacattgctc ctctgactcc catctcactt  18960
tgtccatcgc agccttttgt tgggagatga cactgtcagt cagcccatga tgtctgttca  19020
cacgagatgc tttttaata gaattgacca atgttttgct gccactgatt aaagtattat  19080
ttatactaat tgttgcttgt agttttgatg taattcattg atctatattt aaaataataa  19140
aaggtgtagc aaaatctccc tcctgtttgg tgccttaaca gaagcattca tcctttgtta  19200
agtcttctaa aagctaacat ttaacataaa caagttatta ttttctgcaa taaattaggc  19260
accatttttt ggggggtgcc taaagtgtga aggttaaacc atgtaaggct tagcaattct  19320
attattacca cctccttaat gtacacacac tcccagttgg ccaccatatt ttgtgagcat  19380
tgggaagcct ggggttgaat tcagggtaca gagtgttggg tgttaatttt ttgaagaaaa  19440
agtaattgcc caggttaata gggggatcca ggttggcatt ctgctgggcc cgggccaggc  19500
cccagacctt tttggtctgg aagccctcag aggaagtctt tgggaagtgg tggatgagac  19560
accttactgg tcccccaccc ctaaggcagg gagagcgtgc tgggttctgg gccgagctga  19620
ggctcctggg tggctgctct gacctgaccc ccgggcctcc actcttgggc ttctactttt  19680
ccagtactgt taagctcctg tggggactcc agcacctgcc cctccttctt ccgcgccccc  19740
tccacccctc aggcaacaat aaacactccc cactataaaa agtgccctgc actacattta  19800
```

-continued

```
ccgcaagggc ttctttacat cttggcctcg ccttgaagaa ggggccaaga caggagtccc  19860
aaaatagatg ggggtgcttg ttccagacag gaaatgagca gaatgcataa aatcagacat  19920
ctgtccttaa tatatggaag ggcttgcccc agacgcgtgg acatgtgtat ttataagtgc  19980
gcaggcagaa gtttaaatat tcagacacat tttatgattg tcctctgccc gtcttctgct  20040
taatggctcc tcccgtgccc accaatacat caataccgtt gtgtgtattg aatcgcgggc  20100
agggatgagg aggaagcgag tccatagcag agcccgctga gtatagagta cagtaaatcg  20160
ggaccctcgg cggacggcgc ttcccgcccg cctgcccgcc atgttgggga gccctccctg  20220
ccccccgcgc cgggctgggc ggccggggct cgctggcagc cgggggaggg cctttcataa  20280
cccggagaat tttctaagtg cgaggaagat gataagaata gatttctaca agtcccgacc  20340
acgtgattgg cgaaataatt aattcagcac gtcccttaag aaacacggag tcgtcattaa  20400
tctgccacgc aaagggctct ctccgacttg gaaagtgcag ggatcccaag aatatcaccc  20460
gtccaggggg gccgcgcggt gcccccggcc ctccaccccc ggcccccggc gggcgcggga  20520
gcgcggccgc aggtaaatat tttggcaact tttatttcat cagatttaaa tccttaatga  20580
acttagctgt cacggccgct gacaaatagt tccctttgct tcctgatttg gaactgcgcg  20640
ccggcgagaa gttgttagtg gcttggatgg tgacctttgg ttcagcaaag ctttgcactt  20700
atgaaaaatt actgagagcg gccgagtgtg tgtgtgtgtg cgtgcgtccg cgcgcgcgct  20760
tgtgtgtgtg agagagggag agacagagac agagacagag atagggagag ggtgtgtgtg  20820
cgaggcgcta gggtgccagg gggcgagggg tgaggggcga ggtgcacgcg ggctgctcca  20880
agacaacagg agttgtaaaa aaccggcccg gctggcggac gcgcctggcg cacgcgggcc  20940
gaggttgcct ggtcgcctgt gtctaccagg aacaatggtc gctgtcacgg catctgccgc  21000
ctattcttaa accggtgaga aaaggccctg gccctctttt caagcgaggg tcgtaaattt  21060
ttctttgcgt cataatagaa ggctataaaa tcgagttgaa attttacccc aggcaggttt  21120
taaccaacag ataatgattt ccgagttgcc tctccccccg ctcctctctc cccacccaag  21180
ttctgctgcc tctgtcaccc cagcgagttt cttcttcttt cccgtttatt tttgtgtttg  21240
tattttttat ttctattttg gaagagctaa aataaacgcg agaagaagtc cctgcagccc  21300
gagtgggaga ccccggggcg acgggaagcc tggggaaagg aggatggggg agaggccagt  21360
gcgggctgca gaaggctgtt tctctgctcg ctcccgtttc tgcctttttt caccggcact  21420
ccaagaaaat tgggtgtcct aagagccact ccgctccgtt ccaccccatc cccagcttgc  21480
cagggtcgtg ggctggggca gtagcgagca ttcttttctt ccagcttgca gctccgaccc  21540
gggcgcctct tcattcgcct ccttccctct tgttgctgtg agatacctcc attggctttc  21600
agaatgattt cagcgagcag gggctggctg cgcgtggtgg ttgttttggg attatgtgtg  21660
cgtgtgtgtt tgtgtgtgtg tgtgttttca tttatttttt ggtgtgtgta tatttccccg  21720
tcaggacaga aacaaagttt cccccattat gaattataca ttcaaacaat aacacattaa  21780
ttcaattatt caaagatgac aaatgtttat gtgctttgcg agtgactcgg gcgcagattc  21840
caggcgcttt ctctgagctg cttgcatttt tctcaatgag aatcgtctcc cctcccaccc  21900
cccccactcc aacccactcc aacccaccta gatatcccct tgtaggccca gagaggaacc  21960
cacaaaaagc ttccccagcc ctgctggcag cccggcagcc aacagcctcc caaggccccg  22020
gcttggcggg cactggcccg ggctatttta tcagtgtgac aattgcccgg gttggtgtga  22080
taaatcatcg taagtaattc ctgaaagggt gcgagactgt tgggggccgg gcgaggactg  22140
taaatctttc cggtttattg ctctatgaac atatgctccg attgaagaag gcttagatcc  22200
```

tttcctggag acaaattccc gcaaagcagc cccctctttt ggctggggat taacacttgc 22260
tgctggccgt caggtcggcc tctggcaaga ggctaggggg cggggtcctc cgggtggggg 22320
tgggctgggg tcacccacga tccggcttcg agagacgccc cgagtgggcc tctggccagg 22380
cccggccagg tgaacaaaag gatgggctcg tagacggttc tgggggctcg ggcctccagg 22440
acattcctgc gcctctggag tggggatgcg gtggacctta cccactcctc tggggctctt 22500
ctatggctgc tgggcacttt caccggtctc agaccctgca atcagcaaca gagcatttca 22560
ctgtgcctga tgccgctgag cagagctggc aacgaaacca aaacttcggg gacagggtgg 22620
agagttcccc gtggtgcggg attcccgagt gtggccccgg ctgggggagg gtcttgggcg 22680
ctcattacag gccaggaggt ccgctgctgg cgctggcacg cttaattctt ttttcccaca 22740
ttgcagaatc attcccacca gccactcgga gagtggtggg aatctgtctt ggtttaatat 22800
ttctaaaata taagtttcat tgtcccccag gttagcccag ccaggactca ttgcgcagtc 22860
ctcctcgcct tcctggaggc gccgcaggaa gcgggaagtc gcggcttggc ggttgctggg 22920
cctgtgggat ctgcgggtcc tgcccagacc tggagtcgca cagatcacgg cgggcagtgg 22980
ctcagcgcct aggcggctcc aggcctcgaa ggaccaggtt ggggtgctca gggatcagag 23040
aggggaggtc gctctgggtc cggtcgcct gctacgcgcc ttttctgtct cagaagtggc 23100
ggtgactcgg ctgctgagtc cgcggaacga gccacggaat ggtggtggtg gcggggtttt 23160
ctgaggtgac tggccagagc tgagagtcgc ggcttccacc tttgggccgg agcgggtcct 23220
cgccctggga ggagctgggc gtcggcctcc gcggcgggga ggccgccttg ccggggtgca 23280
tgaggctgcg gagtactccg cggcccggg aagctagggg taccctcagc ctctgctgct 23340
ccacggcagt ctccagagac gcttctaaga gaggcagttt ctaaaatttc cagctcccgg 23400
accagtctgg cggaaggccc agccagggtc agaggtcgtt gtggggagag actctcaacg 23460
cccccaaccc actgagggcg gccaggccaa gactgagtcg gcccggagct gcgaaaatgt 23520
gttctttcct tccgccccac acccatccgc gtctgcccca ggaatggggc ccaggtccca 23580
agcctcctgc gcccttcctt ccagccccca ggcttggctg cgctccggga ctgggtggcg 23640
tgaaagtttc agcctcaatc agtacaagct tccctcgggg tcacgtgaac aaatatgctt 23700
gcatttgaag gcagcgtctg tatttcccga ctatgagggg gtttccgggg ctctctccaa 23760
atccagaaac gaccacgttc cgcaagcaaa acaaatccca agctctgggg ggcctgggag 23820
ggctgggcag aaacccagga gtgggtgggg gcgcgggtgg ctgccgctct gggcccgaga 23880
gcggacgggc gggcgggtgg accgatgggc gcgcagcgca ggcgaagcca gctcggggac 23940
tacgaactcg ttcctcctgc gtttattggt agttgaacct cagcctggtt ccgttctacc 24000
gggaattccg tgtgctcgag tatatggccg tgtctgcgag cgcgcaagac cagggttggg 24060
acagtgttgt ctgcagacaa agggggaagg ctagctctgc cccccactgg cgcccactct 24120
gaggccgagg acaccaggtt tatgataaat tgggatccag gtaagcaatt gcatgacaaa 24180
atggaaatct ttgggcacgg ggctgcttgc cgccctgagc gggatattaa atatgattta 24240
ttttgtgtaa tctgtgatct tgattattgc caattggtga ggcagcccgc gtagacctag 24300
atacactgct acatatacat ggaggacggt gattaatcgt aacaaggcgc gctttgtggg 24360
gacgttcccc gcctaccaaa gggttaggag gacactacct tgccaggctt ggagggtggc 24420
cggcagcatt gggggtggta gtagcagttt aaggagggga tctggtgagg ggattgagtg 24480
ctggaggaaa tatttggggg ctaaatgtgc acttaggaga atgggctgaa aaagaaatta 24540

-continued

```
aaactttttt acactttact gccaaagtaa gatggagcgt catattaatt ctgtgtcttg  24600
agctgccggg ctgggtgcag gcgggttgat ttatatgtat ttaaaataaa ctcggtggtc  24660
agccagctcc ctgcattgtt ccggtagcga gctccacaca cagcctttac ctcttgctgt  24720
tggcttaatt ttttcttggg agattaaaac gctactgagc ttttcctccc aaaatttgag  24780
agaacctcca aactacccag aagagtttgg gaggttcctc cacatttccc tttaccaatc  24840
caggcttttg attgccgtag tggcagagaa aaggtttagt gtttctaggt ccttctcccc  24900
aaagaaccct gaatgaaagc taaatcatat attggttcac gaatcccatc tctccttttg  24960
tttacttgct ccctgtggct actggctggg agaggagaag acaacccatc ccgggtcttt  25020
ccgtgccagg gatggagtga gcagctccag gagctccagt gagtggttcc atgctcgtgg  25080
taatgccact gggccagacc caaccggacc tttatgggga aagaacctca aaagcaagga  25140
gcattccctt agcttaggtt gggacaggcc ctagcaggag aggaaccgac ttccaggggc  25200
ttcgccatca taagagagca gtaaagttgt tttgtcaatc tcctgcgctt ggcttcatca  25260
gaactgaaag tcgctggaca tttttctttg ctagctgcct tgaagctgcg cgcctgccag  25320
cttagtcagc tgaatccaat taccgcgagt agcatttcat ttggccccat ggagcattca  25380
cttataactt cccccgaaaa tttcaataat ccctaccaag gctccacgct ggccctatcc  25440
taaagagttt tcctagggtg ctgctgaggg atgaggtgta gggttggggc tgcctggact  25500
cagctcttcc ttgacagctc acggacgcag ctccttcctg ctcttcccgt tttggctcc   25560
agaaagagca ccagtgctgg tggtccaaag ccagcccggt taaggctgag aatctgggca  25620
aacaaggagc caaagttgga cccgcgtggg atggtgggtg ggcagggtag ggagcgtggg  25680
agaaggtgct gaaggctttt ctggtggtcc aactttggtt aacttggggt cctctttcct  25740
ttcttcttcc caagcctctt acgccaagag ctcaaagcgc accgcgcacc ccggaacccc  25800
caggcgcaaa cttaccctgt tcctccgcgg ctggaaaaag aaaaatctag ctagaggcat  25860
aagggggtgg cggccccggg tgacctccca acttagctct tcttttgagg ggatgctcct  25920
acttctaaag aactcttttt taaaaataaa taaataaaaa ataatcaagc ggcgaaagtt  25980
gacgtccgcc cacgtgaatg tattatataa agcagctaca ggaccagctg gcttgagagc  26040
cctggtacct cgggcctcca ccgcaccacc ctcaggtccc ggcccagcca agagcgcttg  26100
ggggaggggg gcgggcaagt ggcttttccc cctgggtcca ggccggctgg gaagctgaag  26160
ccgcagcgcg aagttaggag ccctaccggg ctgggatctc ttcgaggcgc ttctgttggg  26220
tgttcattaa ggggtgagtt attgcggtgc gagccaaagg tcacttcaaa ggcttatggc  26280
tgcgcgcttt agtctttaga agcgccggga acgctttgtg tgaggctttc ccgggtgtag  26340
tttagtgctc gcaaactact gagtcgacaa attgcacagg gcagatgcaa gagggggact  26400
ctgtctctct cctttcacct gacggggggt ggtcacccgc tgagcggtga cagtggtggg  26460
ggagcttggt ctgtggcttt gggtgggggt ggaaaggatg tttgtttctt aggcgatttg  26520
cagtctgatc ctgacccaga agtgggcagc ccagggccaa gagtgtggtg gatacttacc  26580
ggaatgaata aactcaggga aagcatctga tatatttaat gtataaatca ggaactagcg  26640
cccaggtcct cttcactgag gctctgtaga gcagcccctg accaagatcc acccaagcct  26700
atttaccttc ctttcctggt gcccttttct gcagcctccc ctgccaaacc cccaccttaa  26760
ttctgcacgg tctctctctt ctgcccctag gagagtgttt ggcttccggg attgggacct  26820
ggaggagcat ttagaatttg gtaggggcag gaggagagca gattggcttc cctgcacctc  26880
tgacccacct ggctagaggg tctggcgctt ccctcacgtc cgggctctcc cctcccccat  26940
```

```
ccagccatgg attttggcgt taaaggggcc ctcgctcccc aggagccaac tgagtctgtg  27000
ttttgccggg gagaaggcgt ctggatggtc acgggtacca tatacaatag tcacattgac  27060
tatgacgtcc ttcaagtggg aaaagccctt caacatgtaa gtgtttgtaa gcaagaaccg  27120
gctgctactg agagttttcc attttgttcc agattcgcct ccacagatat caaaagaaac  27180
ctgaagagcc tacaaaaaaa aaagagataa agacaaaatt caagaaaaca cacacataca  27240
taattgtggt gagtgggcat catttaaata ataatttcca gtacatttcc ctctgcaact  27300
caaggtggcc atctcaaaat tcatacatca agacatagaa caaagggcag ctttgaagtg  27360
ggtcacttca gtatgaagta ccacccgtta catgaaaacc gatcattggc cttcaaattt  27420
atggcgcttt aatggggcaa gcccagtgcc ttaaatacag ggtgcattac agtattgagt  27480
tatctgggct aaataagagt gatttagaag gcgcgtccag gtcttcttat agagcaaaag  27540
aggctcaagc ttagagatcg ggagaacttg ggcggaacgt aaagaagtct cctttcgagc  27600
aaacccaaaa accagtggtt tcgaatcccg aagtagcaaa gccaacagga aagggagaat  27660
cgttgctcgg ttccagtgaa ttcgtgggga tgctcagcaa aagtcttggc cgccagaaag  27720
agatccgtgg gcttctgacc ctggtttagg caaaacaggg ggaggcgccg agaccagctc  27780
gagcactagc ggattttgag agaaactgac cgcaacctcc atcgccttcc ccctctcttt  27840
caacttggat gggctgactc tacccgtcgg tgatttacga cgattgcagc gctagtcaca  27900
gcctggcgcc tggtgtcccc tcccttccca agccccctca gcttttccac tgccaccggc  27960
gtacaagcaa gtgccgagcc ggcctccgca agtcggacta gcctcccggc gtccgaggcc  28020
accacgggca gcagattttt ggtccccagc gaggctgcgc gcgttcgtcc cgcctccgac  28080
cgccgagcag agctgctagc agaagcaggc gccggtcact ttatataatc ctgctgctcg  28140
cagggtgcaa gagcgggaaa agtgcggagt agggaattct tttgctgcgc tgcctcctac  28200
gcggagcctg ctttccactg ctgaaaagtg ccgggccttg ggaagtgttt ttcttttcat  28260
tccttaccga agcgtttact gccgccgtgg tcgcagtcat aaattttgct acaaaccaca  28320
atgacaggtg cattgatatg caccgtgaga gctccagctg cttaataacc ccgtcccctg  28380
gtcgctgtga gcgcctttta tttatttggt atcatattag gtattgatct ctagtagcat  28440
taagtgcggt gagcaagtat cagggttcgg ctgctttgga ggcgcagcgg ttgcggcggg  28500
ccggcgggcc cggggaagcg ggcggtggcc gctcagagaa taccttcctt ccggcaggag  28560
accgtttggc cctgtattcc gggcctgcgg ttgggcctcc aagctgagtt gggcaacttc  28620
ccagcaccgc aagaaagggc gagccagacc tatttggcac ccctttccca ggaggagcag  28680
gggatggcgc cggcggagtt tggggaggct gccctggcca gttccccggg ctagagggtg  28740
gaggagagga ggagggagag gaaagggcag ctgaggactt ggaagaaatg agaagccgtg  28800
ctcgaccacc cctcccccaa cactggctca tcttcacccc aagacatttg ggtcttggag  28860
cccaaatgag caaaggtacc aaagggcgag aaaagaaagg ctttaaaaaa agggtgaggg  28920
ggtgatcgaa aagatgagcc actgaacagt tgaccattgt ccaagtgatt tatgacccgt  28980
tcctgctttt taggttcaag cagagttcac aaggagtagg gatttctgaa aagaaataag  29040
cctttttacc agttttgtaa ctatattctc aggttttgtt ttaagaggga tcacttttgg  29100
gaaactgcat ttttgggggga ctgcaaagcc atttccagta aggacagcac catcactggc  29160
tcttgctttt ggggaaatgg acattaaggt agtggattgt cattgagtgg gaaatttctt  29220
gagacaatgt aaacagttag gaaaacagac tctggttttt caggaagatg cccaatgttt  29280
```

-continued

```
gtacttttga ggtctgtaca cagaactttt tctaggaata tgccatagaa gcaaatatat  29340
atataaagcc atctgtccca gaagaactgg tcagttccta agtaagctat tttaacgtga  29400
ctggttcacc tatctagatc aactttgtca acttgggagg caggagggtg aatgttttgc  29460
ttccacagtt gtaaatggaa tgacagagca gcagcaagtt ctggtagtct gagtgtccga  29520
tgtgaccatt aggcctccag agggttaaga ctgaaagcag gataccagaa aagcctgaaa  29580
cataaccaaa tccagagtgc ctctttcttc agcagggggc aaacatatgt aagtattagt  29640
cacagaatga agacttagct gtccatttga tatccagtaa cttttaacag agaatgatat  29700
ataaaattaa tcaaaagaaa aattaagtcc agctttgtta agtagatatc ctacctacat  29760
acatttaaga acaataatgg aaacaatttc tacaacatag tatcttggta ttaagggcct  29820
gttcctcatc aagacaaatg gcatactcac ttatattcta aaacaagaca aaacaaaaag  29880
ggcaacaaca ctacctacca aagactaatt agaagaattt taaaatttgg gttaggctgt  29940
ttggtgcagg tggagggaaa actagtgaat cattctggta cctgtggtca aatccattag  30000
gccacataag ctgtctagat gatgtggtac atcatgatga ccaggatgga agccagggag  30060
agtttctagg aaggaaagtt gcctgaaaga cagatcaaga attgagacca gggagctgac  30120
ctatgagttt tctttatcaa acagacaaag tgattgaatg gtattagtta tactttaact  30180
ctttaggagc ctttcagaag aagtagggag gcagggagag aagggaaacc cccataaaga  30240
agggaataca aaaggggtag gatttttctt agcttttttt tcttcttcta attctgggtc  30300
cattcatcat gtcatgaaag gttctctcat tggttgtggt ttgggtggga ggtagggtag  30360
aatagattat ccagagcaga tgtcaataat atctatttat acaatagatc caaggcaaaa  30420
ataataaagt tataaagcat tctccactca cccatgttcc atgcatttca aattctagat  30480
ctctttgccc atttccagtg gtatctgttt aaaagtaggg gaggtcaaaa gtaaaaggtc  30540
tagaaaaatg taaatgaaag agaagaaaca ttttctagcc tcaaaatgag tctggaagtc  30600
tgcaagtcct cctgttggtg tttatcccct agttttctac attgtagatt ttacactgct  30660
gattcataga gcttactcag ctgattttca ccctgtcatc gttaagtgga ctatctggac  30720
tttcatgcaa gatgctgtga ttttgaaacc aggtgggggg agaccctttt tttttttttt  30780
tttttttttt tttttaagtt ctggctgttc tgagcatgtt ataggacttt catttcccat  30840
caaaaccttg tgctgaccca atgattgact gattgatcca cttattaatt cacctattca  30900
acaagcattt attgcactaa ctacatgcag ggcactgtgc tggatgttag gaacagtaga  30960
caaatgacac agcccctgcc tgcaaggagc ttacagttta gtgggcgaat cagccaacaa  31020
aatgtctgag gctataagta cttttccaca cagaagaaag gctaaatgga caatcttgaa  31080
gaaagtaaat tgtatctgga ggtagaggga agccctttcc ctcagctaca gttgagctaa  31140
aaagaaggaa actcttctta catttaggaa aaattccttc tgatacttcc agaggttcaa  31200
ataagttgaa cttcataaaa tctgccaggc gcagtggctc atgcctgtaa ttccagcact  31260
ttgggaggcc aagacgggag gatcacaaga gcccaggaac tcaagaccag cctgggcaac  31320
attgtaagac cctgtctcta caaaaaaaaa aaaaaaaaaa ctaagagctg gcgcagtggc  31380
tcacacctgt aatcccagca cttagggagg cccaggcggg ttgatcacct gaggtcagga  31440
gttcaagacc aacctgacca acatggtgaa accctgtctc tactaaaaat ataaaaaatt  31500
agccaggtgt ggtggcaggt gcctgtaatc ccagctactc aggaggctga ggcaggagaa  31560
ttgcttgaac ccagaggcgt aggttgcagt aagctgagat catgacactg cactccagcc  31620
ttggcaacag gagcaaaatt ccatctaaaa caaaacaaaa caaaacacta agacatgtag  31680
```

```
ccaggcatgg tgggcacctg tagctactgc agagtagctg ggactctgaa atactctgaa  31740
atagctatta atactgcaga atagctggga ctttgaaata ctctgaaata gctattaata  31800
ctgcagaata gctgggactt tgaaatactc tgaaatagct attaatacca ggctaaagtg  31860
ggaggatcgc ttgagcccag taaattgagg ctgcagtgag ccatgttcat gccactgcac  31920
tccagcctgg gcaacaagca agacactgta ttaataaata aatagataag taaataaact  31980
cagatccagc accttgccca tctccccgcc gtgaagtggg taggaagcag agagcatggg  32040
ctagtccttc tatattgact ggtcttgcca atgacactcc ctctggggcc tcttgctttt  32100
cttctgacag gtcacctgga gcctgggggc cggcccagct ctctcaggat tcagcagaca  32160
ttggaggtgg cagtgaagga tacagtggta gtcaatgtta tttgagcagg gtcagcaggc  32220
cctggagctt cctgagtgca caatgcagaa ggctgcttac tatgaaaacc caggactgtt  32280
tggaggctat ggctacagca aaactacgga cacttacggc tacagcaccc cccaccagcc  32340
ctacccaccc cctgctgctg ccagctccct ggacactgac tatccaggtt ctgcctgctc  32400
catccagagc tctgcccctc tgagagcccc agcccacaaa ggagctgaac tcaatggcag  32460
ctgcatgcgg ccgggcactg ggaacagcca gggtgggggt ggtggcagcc agcctcctgg  32520
tctgaactca gagcagcagc caccacaacc ccctcctcca ccaccgaccc tgcccccatc  32580
ttcacccacc aatcctggag gtggagtgcc tgccaagaag cccaaaggtg ggcccaatgc  32640
ttctagctcc tcagccacca tcagcaagca gatcttcccc tggatgaaag agtctcgaca  32700
gaactccaag cagaagaaca gctgtgccac tgcaggtagc tccctgaggt ggcctactgc  32760
cagaccaagc cccctccaga ttgacccaag gaagcctagt cagggctgga aatgcaacct  32820
tggaggtcat atgtctaaac tcctactcac gtcaaaatgt tctttttttt agtgttcctg  32880
attggggtca tgaccttgca gtgacagggt gctcccttcc attccaggct gctggtgctg  32940
ttgctggaca ggtcttatag ctattaatag agagtgcttc cttatatggg catatctgtt  33000
ttcctgggct gctaattata actccattcc ctcttccacc caacagctct tcaagatttg  33060
aagataggta ttacaatccc caagcctagg tgattatata gcccatatca cacgaatctc  33120
attcccttaa actcataaaa actaaagtct tagaaagtac catactaagt actttctaag  33180
cattatctaa tttaattttt caaagaacct tttgaggtag gtatatgata acatccccat  33240
tttacagata agaaaactgt tagagaggat aggcaacttg cccaagattc tgaaactgca  33300
aagtggtgga tttgaatcca gtcagtctgg ctttaggggc tgctaagcat aaccatgagt  33360
ctctatttgg cccacctcag cccaattctc ccactccagc aaatccataa tggggaggtg  33420
cctgtcctag taggagagga tattctggga gacagtaaca gccttggatt tctctaactg  33480
gaaggggagc ccctccagtt ggggccttct ctaggtccac ccagggcatg tagaagatag  33540
gcatggccag gaactctgag ggctgttcct tctctctgct tagactgctt ggttcctgaa  33600
atttctgac cttgtggtat ctgatgtggt ttatcttcag gtagatgaac ttgcttccag  33660
gtccagggca agtttggggc ctggggtgtg gcttgctatc agggatctgg tttgcctgat  33720
gttttctggg gctgctgctc ctagggagag ggtattatcc tgcctgcaac ctccttttcc  33780
tgcccctcct tcctcagctg caggctcagg ccctccctcc caggagaaat ccatttgtct  33840
tccctgggag ggagtggaca agcagctgag aggtggcagg gtagtaaaag ccagtgttga  33900
ggctgctgct cctagcactg tgaatactca aaatgcttcc agcctggcct tggactccct  33960
aaaataccca ggcagtgttt ttttttgttt gtttgtttgg ttggtttttt tttattttt  34020
```

```
atttttttggt ttgtcacctc cctggctttg agtgcagttg ggctgcagtg gggcgccaag  34080

atctccatcc ccatactttg ctgggggttg gtggggggct ttgcccagag gccagctcct  34140

aagcaaggca ggctggagct atttcctctt cctttccttc tccatacccc acccctggca  34200

gcagaggctg ggaggagtgt tcaaaggagt ctggcccttc tttgacagag ggaggcctta  34260

ccagctgctc ctggtctctc attaaactct ttcatggcct ttgggtgggt atgggatgat  34320

ggactaggct gcaggggaga gggtgggcag agtgaactgg atctcagaag gctgatggag  34380

gtttcaggtg cgactgatag gtaggcctag tagggggttg gtaggtaggt gaattccccc  34440

ttggaatcat acctctcaaa cggcccttcc cctccccagc caggattgga ggtgggggga  34500

gggaggagga aaagagaacc agggaagcac ccctctccag tcctgagggt ccccacccac  34560

tcgctcagcg ccctccctct ctccctccct gcccaggaga gagctgcgag gacaagagcc  34620

cgccaggccc agcatccaag cgggtacgca cggcatacac gagcgcgcag ctggtggaat  34680

tggaaaagga attccacttc aaccgctact tgtgccggcc gcgccgcgtg gagatggcca  34740

acctgctgaa tctcacggaa cgccagatca agatctggtt ccagaaccgg cgcatgaagt  34800

acaagaagga ccagaaggcc aagggcatcc tgcactcgcc ggctagccag tcccctgagc  34860

gcagcccacc gctcggcggc gccgctggcc acgtggccta ctccggccag ctgccgccag  34920

tgcccggcct ggcctacgac gcgccctcgc cgcctgcttt cgccaaatca cagcccaata  34980

tgtacggcct ggccgcctac acggcgccac tcagcagctg cctgccacaa cagaagcgct  35040

acgcagcgcc ggagttcgag ccccatccca tggcgagcaa cggcggcggc ttcgccagcg  35100

ccaacttgca gggcagcccg gtgtacgtgg gcggcaactt cgtcgagtcc atggcgcccg  35160

cgtccgggcc tgtcttcaac ctgggccacc tctcgcaccc gtcgtcggcc agcgtggact  35220

acagttgcgc cgcgcagatt ccaggcaacc accaccatgg accttgcgac cctcatccca  35280

cctacacaga tctctcggcc caccactcgt ctcagggacg actgccggag gctcccaaac  35340

tgacgcatct gtagcggccg ccgccagccc gaactcgcgg caaaattacc tctcttgctg  35400

tagtggtggg gtagagggtg gggcccgcgg ggcagttcgg gaaccccctt ccccgctctt  35460

gccctgccgc cgcctcccgg gtctcaggcc tccagcggcg gaggcgcagg cgaccgggcc  35520

tcccctccat gggcgtcctt tgggtgactc gccataaatc agccgcaagg atccttccct  35580

gtaaatttga cagtgccaca tactgcggac caagggactc caatctggta atggtgtccc  35640

aaaggtaagt ctgagaccca tcagcggcgc gccctgcaga gggaccagag cttggagagt  35700

cttgggcctg gcccgcgtct agcttagttt cagagacctt aatttatatt ctccttcctg  35760

tgccgtaagg attgcatcgg actaaactat ctgtatttat tatttgaagc gagtcatttc  35820

gttccctgat tatttatcct tgtctgaatg tatttatgtg tatatttgta gatttatcca  35880

gccgagctta ggaattcgct tccaggccgt gggggccaca tttcacctcc ttagtccccc  35940

tggtctgaac tagttgagag agtagttttg aacagtcgta accgtggctg gtgtttgtag  36000

ttgacataaa ggattaagac cgcaaattgt ccttcatggg tagagtcagg aagcccggtg  36060

gcgtggcaca acacactttg gtcatttctc aaaaaccaca gtcctcacca cagtttattg  36120

atttcaaatt gtctggtact attggaacaa atatttagaa taaaaaaatt tcccagtcgg  36180

aa                                                                 36182
```

<210> SEQ ID NO 25
<211> LENGTH: 110
<212> TYPE: DNA
<213> ORGANISM: Homo sapiens -continued

<400> SEQUENCE: 25
gatctgtctg tcttctgtat ataccctgta gatccgaatt tgtgtaagga attttgtggt 60
cacaaattcg tatctagggg aatatgtagt tgacataaac actccgctct 110

<210> SEQ ID NO 26
<211> LENGTH: 41500
<212> TYPE: DNA
<213> ORGANISM: Homo sapiens

<400> SEQUENCE: 26
taaaattgat aacagaaagt ttattcaaga attgtttgac agacaaccct tttaggtaag 60
gaaaaaagta actactgaag aacaaagaaa gttccaagag ggaattaact ctagttctac 120
aaattcagga ctatacagtg acgattagga gctgagttca tgccttttag aactaattac 180
aattgttcgt aagtacgagt ttaacataaa tctacagctc ttttctagag tacaatagta 240
actaaaatag ctggttttac atgacaggaa acacaatgtc ctttgtaaca ggtaaatact 300
aaaaaagtac aattttttcc ttttttcccc tcatataaat acataatgta gggggataaa 360
taatacaaaa aagaaaatat tttaacaggc tataaccaat aaatatatat gaaaatgttc 420
actagaacac acgctttttt gagcaatgct ggacttctgc aggcccagac atctctcaca 480
gttgttttta catccattaa aatgtaaatt ctaagtgcaa caaaagtgtc ctgtcaggag 540
gctgagcaag gcacacaggc cctgcccagc ccctgcctgg gacagtttgt tcaaatatac 600
cctgttttca cgttaagtca agagagcaac agaagaaaag tatagaacct cgtgtcacca 660
actgctttct gtggagaggg ggatggagct ggagctgaga tggaggcagc agaatgggca 720
aaccttcagt cctaacaacc tgcctgccct agcctccaca cttttcctta aaaaaaaatg 780
tatataattt ataatatagg cagctctttc aggatctctc accatccctg agccctctaa 840
aaactgtaat tgatgggggt gggatgtata gatatgaatg ttctagagca gaaaaaccgg 900
gggctagaag tgtacctcaa taaacctcaa atgggaacaa atttgaggtt ttgggaaagt 960
tggaagggaa cgtgttttgt gccttttggg tttgaaatgt gttttcttat tttttaaagg 1020
ataattgagg aaaaaaaaaa atcaagattt ggggggaatt acctacaaag atgtaaggta 1080
agtccgttgg ttggtgatgg cctagccatc ttgtctggtt tttaaaatgt gcttttctgc 1140
ctcgtcctgt ctcgtcttcc tctaccccac tcccgggcgt ggaattccaa cttggtagtg 1200
ctggagccct ggggttgatg gggtcatctc caatatgatg tggattcctt tccgatgggt 1260
tggcaggcag atggaacaag gggtggaaga cttaaaagca acctctcagg ccaggggggaa 1320 gggaaggagc tccaggccgg ttctgaccag gaagcctggg taccaccttc tctggctcct 1380
cttttcagac ctccaggttg ccccccagag ctccacagtc tctctcttcc tccccatccc 1440
ctaatcctcg ttcgcccttt cccatcacag gtgtgttaat ttgggcgctt cttggattct 1500
accctgagga ggaggcgcgt ggtgagagga gaggtctgtg taggtggggt ggggttcgca 1560
gggtccgtgg tgctggctgg gcgccatagg gggcgccccg ttgtagtcca ggttcccgga 1620
agggtgatgg gaaaggtggt tgaggccata gagggagggg ccggcagggg gcggcagcgg 1680
atccgcgtag ccgcccccgc ccacgtacac cggactgccc tgcatggtgg gcgtcccgta 1740
ggcgcccccg ttggcttgga ggacgtgcgg ctcatactcg ggcgccgggg tcggagggta 1800
cttctgcggg gcgccgcagc ctttgagagg gggctggtag ttggagggca gcgcgtaggc 1860
attctggtgg gctttaccga aggcgggtgg ggacgggctc tcgtagctgg gggtcatgga 1920

-continued

```
gtgtaaggcg ttcatgaagc cggccgtgga ctgcatgggc tgcgggggc tgccggctgg   1980
agatgggccc cccgacgacg aggccaatcc cttggccttc tggtccttct tgtacttcat   2040
gcgccggttc tggaaccaga tcttgatctg ccgctcgctg aggttcagca ggttggccat   2100
ctctacacgg cgaggccggc acaggtagcg gttaaaatgg aactccttct ccagctccac   2160
cagctgcgcg ctcgtgtacg ccgtccgcgc ccgcttggac gccgccgacc ccgggggct    2220
cttgtcccct cccccgccgc cgccgccacc gcccccgctg ccaccactgc ctccgccgcc   2280
gccgccaccg ccgccgccac cacagccctc tgctggatcc gagggggagg ggtgggaagg   2340
ggagaaaatg aaataaaaga taattactga acacgccgaa attgaatgca tcgtttctta   2400
ataaatccag gcctggactc agagcccccg ccgccctccc cttcgggtcc ccgccgcctc   2460
ctcactcccc caccccaccg cccgtcgcat tagcggacac tctataatag tggcatttat   2520
taagagacct gttctccttt cgctgcccca gcttatgaaa atttgatcat gtcacgcaga   2580
cagagccgca tggccattta tttagggctg gattttcgcg tgcgtgcttt ctccccctta   2640
tccccaattc caggtcaggg aagacatttc ccctccccgc ccacccgtc ctgaggacag    2700
gatgggagac tgaggagaat cctcggggta atctggacac tcgtgggcag gaagtgtggc   2760
acgaagaggc tgccgtttct ggaggccggg accccgggcc gtccaagcga ttgtgattaa   2820
tacccacagt aatcatactt aataataatc aatcgttgac gactctgcat cctcccggca   2880
gcgcctcgtc ttggctctgt ggccttggga agggctttga ggccacgcac tgggccttct   2940
ggagctttca gaagctccgg tggagggcag ctagagggag gagggtgttg gcggggtcag   3000
gggtcattag gggtagggg tatcaaaaat gtacccgctg gccacctaat attgttccca    3060
ggcagcctcg cgggcgccta ggggctgggt gctagaataa cagtgacatt cctggctccg   3120
acaaaagctg aggacaagga aggcagagaa ctggtacctg tgccggggga gttgtttttc   3180
agcttggacg tttgcctcga ctctttcatc caggggaata tctgtttggt gagggtggag   3240
ttggtgccgg gaccgcactt tgggggacca cttttgctgg gcccgccccc attactgctg   3300
ttgctagtgg cactggtagg tgcggcactg ggcgggggtg agccaggcgg ggccgacagg   3360
ggctcggggg ccagacccgg cctcatgcag ctgccgttga gctccttgct cttggcatgt   3420
ggggcagcgt tgcccaggga ctgcagcgag caagctgagc gctggtagtc gccctccagg   3480
tgcgtggcgg cctgaaatgg gggttggggg gggacatcga agccgaagcc attgctgcca   3540
gggtacgagg aatagcctcc gaagagagca gccgcggcgt tgtcgtagta ggtggctttc   3600
tgcatcgctg ggtgaggcct gggcagtggg tggcaacttg gaaaggcctg ataccctcag   3660
gaccggacat tggcaaccct gggggtcacg tgacacgccg gacccccccc ccccacctcc   3720
cctctctgcc cccctcctcc ggggtctgtt ccaagcggct gacctgcgag gcgagagaag   3780
agacacaagg gggagaagag gactggggct cgaatccatc ttaggaactg aaaagggaac   3840
tgacatcaat agggtttttt cttttcccct ccccaacatc tccaaagcag atgctgagaa   3900
aaaaaagccc accagttttc atttccacta aaaaataaaa aaataaataa agactatatg   3960
cctttcaaga ctgcctagat gtagaatcta tggcaaaggc cattgcttct ctcctgcctg   4020
tgcactagcc cctgacctcc cctagtccct ctctccctat ctctcctccc caactctggg   4080
ataggatggc tcaagggagg ggacactagg agactccaaa ataaaagcat catcaacacc   4140
ctcctctgag cccagaggct tctatgcttc cagcctttgc ctccttccaa gtcggtttag   4200
gtctcttgcc caagcaaagt ctagcctgaa ggaaaaccaa aggatctcct aaaagaacag   4260
gcaggagaag caagttcagc agagaagctt ctcttgtgag gtatcctctc cacttcccac   4320
```

-continued

```
cactctccca ccaggaagac aacaacagcc tgacctagaa acttcctgat gatttttaac   4380
ctcaagagcc agctgaaccg agactcatct gtccatggcc ctgctgcagg taccaccacc   4440
tccagccctt gtctttgctc agccaaacct gggatcgggc agccagtggc cctgtggggc   4500
ccccacatgg agcaggattg tttcaatttc ctgggccacg ccagttggtg ctgtgaccat   4560
ttggcccagg tctctccccg gacctctttt tttttttttc atgagactta atttttccca   4620
ccctttcctt caccgtctgt tttctttgat ttcccccaaa gcaaataaga aacaagaagt   4680
tacaactgct agacttttct actgagacgg ggaaagtgct ttccaaaaga gaaaattatt   4740
cctgaggaaa aaaaaattaa caaagcaatt ttaacaatat tattctctag gttagaaaca   4800
gaggtattcc tgttgactga ggttccctga ggcaaaaaaa aaaaatcact attttaatac   4860
agccttttaa aagtgtgcca gaaaaataaa gattcaaact aacataggat tttgtgtatt   4920
tgttctgaaa cttctgactg cattttttttc cctccatctc tcccaactct tcaccatcac   4980
ttttcataaa acctccatac tgccatgtgt gtttggaaaa ctttaatctc attcagccta   5040
gctgttcaac tccaaagaaa actaaacata ggaaaataaa ataaaaggag tgcaggtgaa   5100
gaaaagtccc tccctcacat aaatcccctt cttcatggca cagatttata ctcaaaaggg   5160
aatcagtgta accctgagtt ccgattggtt tctggaaata cacatgggtc tgcaaagcag   5220
caggtccttc cagggagaac cagagttcaa ttgaccaggc tgacccaatc cctttattat   5280
tattaccatt agcctctgct gatttaacca aaattagctt ccaagcagcc ctggctgaag   5340
ggggaattaa ttaacaggca ttagttgtgg ttgttattaa tagagaagag aatgaaataa   5400
aaacgttgga gggggttggc tggctaggcc ctggctttat ttagtctgat tgttacagca   5460
ataataatga tgacgatgat gatgatagta ataataataa aacaataatt taactagatg   5520
cctggggccg aaattcctgc cgctcccctt gcaataaacc ccaaaccatc gcgggacgga   5580
ggccaggcga gtgtggaaag cgaaggagcc agagacgcga taggaaagaa tggagactcc   5640
gccggtggtg cagacagggc tgggaaggtt tgtgcacccg ggtagtccct ggctgctgct   5700
gccaggctgc ctcagccggt cgctgctgcc gcggcgactg gcgacaagct accagccacc   5760
tacgatggcc caaggaggcg aagaagagca agcgatcagg acaccaaaac ggttatcgga   5820
ggcaggttcc cagcacacca gccggccgag ggccgagccc cgcgggcggc agcaagtttt   5880
gggagctgga ggtaaccgaa ttaaaaggcg ccttagaaac tccgcttcgg gactttgctc   5940
agcagggctc cgggttggag ggcgccgagg cctggcggac gggacagtgg gaagagagaa   6000
aggtgctaag gggacccaag atctgggatc cagaacaaga gggggtgggg aacaactcta   6060
ccaagccaaa cagatctatt tcccttgcct ccatgttgga aaaattcagg ttccatatgg   6120
ctcctcggga gggagggagg gagacggtgg ctgccggctt ccccccaggg tctcgctgga   6180
gaagggagat gagccccccg caagaacccc accttgccaa gcacacccca gggagagcca   6240
ggagagtaac aatagctggg gaagccccga gagaggggat aggccatctt ccaggactta   6300
aaaaaattaa tgggagaaag aaaaataaca agaaaggaag acagagaaag gttgagactt   6360
tcttagcagc cgcggagaaa attcagccct ggatctggct gctgaaagaa aagagagaga   6420
ggagaaaaga ggagagaagc aggaagagag aggggagaga gagagggaga gagagagaga   6480
gagagagaga gagagggagg gagggaggga gggagggagg gagagagaga gtcgctgcgt   6540
ggaaggaagc ttaaagcttg tgaactcttc ttgaaccgag attggagtca tatgggccat   6600
aaatcattga gacatactct ccgccattca caaactgata gcctatttca gtccagctta   6660
```

-continued

```
ccttagccac cgacgagggg agaacaggca gacataatat atattcacat cgagccccag   6720
agcgagcggc aggcgacaaa tctcccctcc ttgaaggcaa aggaaaaaaa gaccactgtt   6780
taaagctgcg tcgccccccg cccccccgcc cccgccccgc aaagccaccc cggctgggga   6840
gcccgagggg cagaccggcc agaggagccg cgcggcgtcc gcttcaattc actcggctta   6900
ggagcagggg tgcgcaggag ggagggggtg ggggagcggg aaaaaaaata gaagaccgaa   6960
aggtgccggg cggctcagct cgccagaatc cagctccggg ctccagcagg gctaagccgc   7020
cacagtgtgg ttgccctata agactggtac gccctactct ccgtaacaat ggcctctgct   7080
tttgcacagg gaaaaaaaac cacacagaca cacacacaca ctcactcaca cacaagctca   7140
cacccccccca cctctccccc tttagcaagc ttagatgcct gataaggagg gaaggtgatg   7200
gtggtgatgg ggaagggggg aaattttaaa atacccgcct ccccaaaaaa agagtaagaa   7260
gaaaagaagg agggtttttt tttttccctt aaagaacagg taaaaattta aatctagatt   7320
ggagggacag ggaggaagag gtgagcaaag gcaaggaagg gcggtgaagt tcacagctcc   7380
ccccataccc cactagtgaa ctattatgct aatatgagaa gtagtatttg gaggctgagt   7440
caaaggcagg cctggcccgg gggtgagggt gccgggtgcc cctctgcact cattcgcaat   7500
tggaacacca ggactttttt agaaagtagt tctgggtctc caaccctcac actctggctc   7560
cctccttctg agtctccagc cccggcttct tccctccact acaccctctc tattcctccc   7620
aaatctccct ccagtctcca ggcccagtct ctaaccaagg gagagggaaa gaccagaact   7680
taaaaaaaaa aaaaaaaaaa aaacacccct ccccctttt ctttttgaga acagacaaca   7740
agcggtgagt gatgatttta aaaactctga acatcttgca gggggaggag ggttgagaaa   7800
agggtgacaa aaggaggact ctgtgtttta gtttgagctc cagactggct ggcagtagac   7860
gggctgaaag aacttcatgg ataagtttct gttatgattc tcacctccga ataggcagaa   7920
ggggctaaga ggtgataagg acatttgtac ttctaagaag agaagaacta gcagggtcgc   7980
ttaattttaa atgcactggc agaagagatg gaagatggtt attattatta ttcagaacaa   8040
ccctgtttgt ttctctctgc cctgcaagat ttatgactct tggcacaagt gaggaaggcc   8100
acaaaagcta aagttttctt agggtgtgtt tgagcagggc aggaaaaggc aaggaggagg   8160
cctgtaggag gaagacagga gccaaaaatg taggtgtctg cagatttggg acagggggtg   8220
gggaatagtc attccgggag gaaggaaaag acaaaaagag caccaggaca tttcccaaag   8280
caggagtgtt tgcaactctg cctaactgct gactcggagc taggggatga aatagaaagc   8340
tgactctttt ctctaaaggc agcttggaaa actggtcctc ttaacttcat gtaaggcact   8400
accctgtgat ttcctggtta gaatacttgg cttttgcctt ctcccatctg gatgcaccag   8460
aagagggaac gggactgggg acaacaaagg tgagagttga tttccagctt ttgtgttccc   8520
tccagcatag gttggaggtg tctggcaaag cttccctcat tccctctctc tccccactca   8580
caggctctac tttgggatga gatagggagt ggcccctggc ctccagcccc tacttcttcc   8640
aggcaaggct aagtcaggcc aggtgatttg gagcagccgg tttccagggg ccctgataaa   8700
ctgggggtac ctatggcctt cctgccctcc agcaacagaa gccacttgca gagcctcaga   8760
atgtaatgtc ctgaggaccc cacctcccac ctagaaagtt gacagctggg gggaagcacg   8820
ggttggggga catggggatg gagggtggga gctatttttc tgtgtttatt agctattatt   8880
ctgtgtttat tagtattttt ctgtgtttat tagtagtatc aagaaaataa aacatccaag   8940
tcagacctag acttggggct caagccagcc tggaacccca aagagacctg ttaggggtgc   9000
ctgagcatgt ggctgcaaaa agtctgtcct gagatctcta cactctggtt agagacctac   9060
```

agggtcagac cccatgtaac tttgagcttg gtgggtcagg gactcaggcc agggaggctt 9120
ccagaggctt aaagaaacca gtacctttgg ggtttttttt tctatcactc ccccaaataa 9180
aaaaaaagcc aagaatgtac ctcaaaacct ctgctgtcct agctgttact atcattgggt 9240
tagagaaggt cattgtaaaa ctgagagaag aggagaacct gatcgctttt gggactgcgc 9300
agctttgcct ctaggaataa cacgagagtc cagaaggcac ccaggcagcc tcgggccggc 9360
tgcaggagaa gcgggcctgg agctgagctg ggagtggagg agtgttccag agacaacagc 9420
agacccctcc cttccccaag cctcctcaac tctttgtggt ccctcgggct acagaaggca 9480
gtggggcata gtggggtggg agtgaaaaag aggaccgaga agcaagaaaa tgaacctgga 9540
gaaaatctca gaggacatat acccccaaat gcggtaggag atggagtggg ggcttcttaa 9600
ttctggagta cagagcccat ttggaatact tgggaggcaa ttagatccca gtttagtttc 9660
tgtcttgcct tttttcttcc attctcagag gtctctggcg agcaggcggg ctgccctctg 9720
attagggctg ggaggctgga ggacggaggg tggaacaggc acccctaagg gcccctgttt 9780
ggactgaggt gttgctgcta gccaggggat tttcaaactt caggggataa aggctggtag 9840
tgaggagttt gagcagggaa cttggggtgg gggacgccag agcaggctga gggaagactt 9900
tggggtctgg gaaaagagaa gcaggagaag ggcttatcat ccctgagagt gaagccatga 9960
tttcggaaca gactggagat acagaagagg gaacaatttc ttcttggatt tgggagggaa 10020
acctggaaaa ctgtgtgtgt gtgcccatgt gtgtagggtg tgtgtgtgtg tgagagagag 10080
agagagagaa aggaggagaa agagaaattg aaaaagagga aaattgagta agagacagag 10140
acactagcat aaactaatga agtaaaaaaa taataagggt aaagattaga gaaaatgccc 10200
ttcttcacag acatcttttc ctcttccatt ccgtttcttc agagccagag cactcgctct 10260
ggcacttctc tcccccaccc cactgggtac ccagtatcag gcgacgggag cactttaaac 10320
cctctggaac aatcaagggc tacccgccct tctagacctc ggcggcggga tcgtgcctgt 10380
ttctctcctc ccccaaaaat gcatcaacta gcaaacaaaa attctctcaa taagggcata 10440
ctggttggct cttttaaaac caatttctga tctcagactt ggggcagtca aggatcctgc 10500
ccctggctca atccacacaa aatttgcctg gcccaaaggc tagcttggga gctaggacct 10560
gtaagcctgg ggcgagatgt ttggcgatgt gtttcttcct ggccctgtct gggttcccag 10620
tcccacactg ttttccagct tcactgccca actttgtagc cctagaaaag tggtgtaaag 10680
gtcacacact cacccgaatc tccattttcc cctaagtatt aacgaagatt tcaaagctgg 10740
gagttgtaaa gtgggaattg ctaatgaaga aggctcttgg catttggatc cccatctcca 10800
gctctccaat aagccagagc aggagggaac aaaggggcac ccggaaggga gaagaggaga 10860
ctcgcataga cactgctcag caatagtggg gatcaaaaga agaaaaaggt cgctgcagtg 10920
gaagaagaaa aatccaagct gtactttttc cccaccccac gtgtgggggc gctgccctct 10980
ccccagctga gcctgtgaag gggtggcagg acaaaaaggg cagccacaag ggtctgcgaa 11040
gtccactcga tgaccacgga ggccgcctga acatgctaat gaggggatgg cggtgctgcc 11100
agcgagttgg gagcctcagg caggtgggct ccttggtggt gatagatccc aatctgaatc 11160
agggctcccg cctcacctag aagctcagcc ttagcctggc aaaccccacc cccagcaagt 11220
gttgagacaa aggtgggcag agcagagaag gcagaggaag ggaggctgca aatcctgggc 11280
agcttggggg ctgcaggggg tgctgggaaa gggagggaga agcaggaaaa gaggaacggg 11340
cccagtccct gaggttcagc gggcctctcc tgacagactg gatgtttctc tcccagtgac 11400

-continued

```
ctctgtttag cagacaataa ctcagtggat taatgaccaa tcagcgaaag gccttccgaa  11460
ttgcctccaa atataaaact ccgaagtcag aatgggacag agccagagtc tgggcctgcc  11520
agctcttttg tttttttttt ctctctcaaa ttagtgtttg gggctaggct ttaggaagtg  11580
gattatctgc ccagtgtctc agatttccag agccccaaag atgaggttgt ttcccatctc  11640
ttcccatctt cttcttccct ccttccccgg aattcatatt ccaaaccaca cttcccaagg  11700
cagcctggaa acctcccctc ccctgctagc ctcttcacat ccctgatcct gcaagaaatt  11760
tccttgctca caaccatgca attgagaagc caccactcct ttggaactgg gggaggagct  11820
ggaaaataaa agcaagtata gagtgggagt cttccaccat gcaggccttc tgtcctggct  11880
accctagagg agacccggta gagtgctgtg gcaccctgtg tgtgcttcct cccaagaagc  11940
cagggctcag aggcccaggg ttggggtgag gctgagaagg gaggcacctg ctatcacaga  12000
atctaaactc tgaaaccact gttcagtccc tgggctgggg tagggggcac cttaaaaacc  12060
acactctgtt gggaggccga ggcaggcgat cacctgaggt tgggagttcg agaccagcct  12120
gaccaacatg gcgaaaccgt gtctccacta aaaatacaaa attagccagg tgtggtggcg  12180
catgcctgta gtcccagcta ctcgggaggc tgaggcagga gaatcgcttg aacccaggag  12240
gcagaggttg tggtgagtgg agattgcacc attgcactcc agcctgggca acaagagcga  12300
aactccgtct caaaacacac acacacacac acacacacac acacacacac acacacactg  12360
aacaatgaca gccttagccc agtgcctggc agggaaagac tcttgctcag taaggcccag  12420
cccttcttta cttagccctt ctccaaatgc caatctcaac ccaacccagc tagctggccc  12480
ctcaccactt ccttctagtt ccactgctct cctcagggct actcctcagc tgagaataag  12540
ggcaccttca gaaagaggaa tagtccagat tccagtggat ttcctagagc cagactgagt  12600
aagcatccac tgctctgggt gtatgtaaac tctgaatatt gcaaataaac atgcagtaac  12660
ttctataccc agatgcccac agagctccag gacacacaag ggagtgcctc ccatgcactg  12720
tcctgctgag gatgggtaca cacagaggtg cccaatttca gaacaggaga gaaatcagga  12780
agtgtccagt ccaactcttg ccattgttac agatcaggaa actgaggccc agagcaagga  12840
agtgatttgt ctagagtcat acttgggata ggcttgggag ttggaaggcc tgaatttcag  12900
atgttccagc ttggctatgt gacatgaggc agggcactcc ttgggcctga gtgtcccctt  12960
ctgtaaagcc tgggcatgtg tatggaggga aggggtttag ctaaatgatc tctaaggtct  13020
ctttttggac tgaatgttag tgattctcca tgtgctgatg taaaagtgag tgacaagaag  13080
taataaactg agttcagaca ataacgggca ccatcgtcac cagattcaga gtatttcctc  13140
ttgaggttta aatgcttacc accactgagc accaacccga tgcctggccc tcccttgccc  13200
catagaggct catgcactgc gttttactgc tcttctgtgt gtagggtggg ttgttttcta  13260
ccctcattac caaaccaaaa gtgctatatt tagacactgc aacttgagca gtaaataatt  13320
aattagtcta attaaaggag gaaggtttca acctggcaat ttttaaccag gcatcaatgc  13380
acccattgta ccagccgagc cctctcaccc gaccccctcc ctgcccatac acctaccagc  13440
cttcccagtt gcctccccct cagttggaga caagcattcc cccagatggc cagcagggtc  13500
cacagggcca gactgtgtcc ctcatgacaa agttccacgc tctgctgtgc ttccccatag  13560
aaataggtct gccggcagct gcacctcaaa gcttgctttc cctaccccca aagctgtgct  13620
gggctccagg tctctgctct ctgctcttgg gaaatgtgta atctacctcc ccagctcaag  13680
atgccccaac aatgcagcga gtttgcattt caagaaactc ccattaatat caatttactt  13740
cactgaaacc tcgggttctt catcaagttg atgatttatg ataaaatcaa ttaaattacg  13800
```

gccacttagg gcccagccgc ttcctctcag atttcattgg tgcggggccc aagtgtctgg 13860
tggaaaaatg caagtttagc tggaggcgag gaaagataat tctgcggctg agaaaattta 13920
atgcaaaaca atttccaggc aaagctgggt gtctggacag aaatgcaaga gccactagtt 13980
ggcctgcgga aattactatc tgggggtcaa aatgtttttc tccccaccgc catcctcctg 14040
catggctccc ttactctgct cgtctttgta ttattcactt gctccccact cccaaacaga 14100
gattttgggg gaattcgagc agtaatggtg ggacacaagg ctgccaaggt ccagcctcaa 14160
accacggatc tccccgatct tccctaccac accaagcctt ttctcctttt ggcctcccct 14220
cctcaaccaa ccatactcac taattccttg gcttcccacc acaaagttaa aaattcaaag 14280
tgaagatgag gctgggtggg cagaaggcac aggaggcaca cagggaaagg gtagaggggc 14340
aggggccagg aggccaggcc aagtgggctc tgctgcatgt ggctgcggga agaaaaaagc 14400
aggaaagagc actacttcgt ggacaggaca aggggcagtg tgtctagagc tacctcatcc 14460
cagagttcca gaaccagaga acatggggtc tctctcctga ctcccaatct cccagctcac 14520
aaagtgattc tgcaaaccca tccgcaaagc cccacctgga gtacatacag ctcccgatgt 14580
gcagatgcac tcacacaata cacaaacata cctacacatg tgcctgctta catgctccct 14640
ttgcatacac ccaccacact gtgcgcctgc aaagggacag ttcccactat tctccctcat 14700
ctgggaaaat aaatcccagt gcgtcaggct ggcatcgctt cccactccaa ggagaggggc 14760
ttctctggcc tctgctctgt ttggtttttg gtttccagag caggcaggag taaacacagc 14820
ttctctgaag ccataaatca ccccctttcc taccttctgg gcttaacact cagcctcagt 14880
gcaatccctt gtagttttgc cttcaaataa cccgctaggt gctaaagggt tgggcaatgg 14940
tggcagctgg gttgtggaag ctgacccagc ggtcgccccc caaccccact gcccctaaca 15000
gatgcccctc acatttccct cagtacccac agcccccaac tgccctggaa aaccctcctg 15060
ggcctcaacg ccctttctga gcgggagggc tctcccatcc cctaacaaga tcatgtccac 15120
acgcccaccc aaacagctcc acattcctcc acactcgtcc tccaccccca ggtcccttta 15180
ccccttgaa gcccccaccc tgcctttcaa agttgctctc atcttcgtct tcaattcgga 15240
tcccggcctg tcccaggaga gaggcctggg ggcgggggtc tcagccaccc acctctgcac 15300
ccccgccagg ccccgagcgc cccggctccg caccccacac ttacctgtgc ggtcttccgc 15360
tagggcgcgg gcaacggcgg gcggccgggc gctgggtgcg cgcgggggcc gactgccagg 15420
ccccggaccc tcggcccagg ctggggctcc gccgccgcag ccagccgcat cctagtcgct 15480
caacccgcag caaccccag caacccccga gcgtcccgcc gagctggggg agaggcccgg 15540
atgcgctcgc ccccaccccg cccccgcccc cgcccccggc tttgttcggc ctccagggcc 15600
ccaggagcgc gcggatctgg cactccgggc gcggcagacg ccagtttcct gagaagctcc 15660
cactccgtcc gggccgcgca gggctgcggg aaccccgggc tcgtctggca ccgagctgaa 15720
ctcgggcttt gagagcgggc caagttgcca ggcgagagga gcggcaactg acaggggcac 15780
ggcgaggcgt agggagcgcc gggggcgcca tggcggaagg cgggcacacc ggcgactctt 15840
caatgtcacc agcgaaatgg gttccatatg tccgacccgg cagagaaggg aggggaaggg 15900
agagagttct gggcaggaca ggagtgggga cagggagggc ggcaatggag ggaacagagc 15960
aatggcgagg gggcaatagg aaggatcaga cgggcgagaa agatttgcat ctccccttt 16020
ccctcgagtt ttctaaagct gcttaggctg gtaggaactt gctttctctt tttccttttc 16080
ttgttctttc ctgtaagatg gggaggaag gagattagta ggggaagcat ccgcttgtta 16140

-continued

```
aggctgggag tttgagggag gagatgtgga atggaggtga aagttcttag gcggctggaa  16200
gatcaacaac ttccccaggt ccctagagaa aaaaagagac caaacccaca agggggaaga  16260
aaagccaaga aaggattcca gggtccaggt gtgaaagtcc caactccccc cacccccatg  16320
atgaaattct gtttggggag gtcccaatga ttaagttact gatgctggtg attgtggtgg  16380
aggctgaagt gtcctggaca tcttggccat tccctggcac ttcagctcct gccacagctg  16440
cctcacacct gatttagcac ccccaagggc ctactctaga ggcagttgtt tctgagatgg  16500
cctgggcttt gggcagcttc ctgtaaagaa ggctgctagg gagcagggag cctggagggg  16560
cttccctctg tgcctgctcc ccaaagggtt tgggcttttt ttctgtgttg ggtctctctg  16620
tcttttctaa ccatctctgt tgtctccgtt cctttctcac agcccctttg tctttttcca  16680
attctgcgtc tctcagtgtc ttcagtgaat ttgaattgag ccttgcaaag gatttaggag  16740
tgtctccaga aatcacttct gggctcaccc attaggttga gtctcttctt ccctttcctc  16800
tgtgggggaa cccaccctct atccagagaa attctcttct agagagaagg ggacaaaagg  16860
ggtagtttcc ttcccactgc ccttgttctc acttaactct gtgtgtgtgt ccccttgtga  16920
attgtggggc tccttcctcc aggacagcct cccttcccct ctgactggcc tttgtttcca  16980
ctctccctgt catcacctcc ttgggctcag ccttgacttc ccatcccaga aagggatcct  17040
gctgcttgtt ctctctctgg gtccctctct tcctcatctc actcttcatc tttctatcca  17100
attcctctgg tcactaaagc gttagcagcc tgcctcctta aaggcacaga gataaacact  17160
gcaattatat agagaggata ccagcagaga gttaggggag aagacagagt cagcagcttt  17220
cttagagctc tgtctaccag atgcattcta tcccaacccc tgaacaacac aaaagcaaat  17280
cagtggggtg gagggtgcag gactggtaag agacagggtg cttcatagct aaatgaagca  17340
aatgtatata taaacaacaa agtcctttca aacttgctga tttggggtag gcctagatgc  17400
ctggatggaa ggcattaggc atcacatggg ggatttacca gataatggtg gcaagggatg  17460
gtccccttgc tttgtctcct ggggaagagt ctgtgcgtgt tggggaaagg gaaggggagg  17520
gggtatcagt gtcacctcct ctcctctggg ccagaggaga caaagacctg aagagggctg  17580
aaagaataaa gaggaaaagc tggtggagtg ggggtggggg tggttggtca gacttccacg  17640
tcacaggcaa aggtagcagc aggaggggag atggaaaagg gttggggagg aggagttgca  17700
aacgcagggg gaaggggcct gtgggactgg ctctccatgc tagctatggg ctggcccaaa  17760
gagcagatcc ttttctttcc catctttcaa agcatgctga attcagaagc taatacaaat  17820
gattctaccc tcttccttct ctgtcatgtc cctcctcctc cccatggaag aagtgatcct  17880
tccctgctct ctcaaaaact ccaagacttt gccctaactc tggaccaccg gtttgaggga  17940
gaacgcaccc tcttcacagt catacccccc aacactttcc agatgaggga gaagtagaac  18000
tgcttgcctc tcacactgaa tgtgtgtggg attctccaac actcaaggag tgggtgggga  18060
atgagactga aaggtttgga gcccctatgc cccaggtctc tttgctgcct ctgccagccc  18120
ttcccacctc ctcacaatct ccagtgctgt caaagctgcc cctgtatcca gacttttccc  18180
tagttctttt tatccaggtc agacagtgcc tctacccatc ccagccttgg gtcctggcct  18240
tctctttctc cccaaaccct tttcaactga gactcctgaa ttgggaggct tcacccacta  18300
cccactgaga atcccttgtt aacatggatg agactcagtg ttcacttgga gcagagtgtg  18360
ggagcgagct cctggatgct gcagggactg gggcctaagc tgccactcca cgtagtggat  18420
gccatgaata attaacacct gggcgcggcg ttgctctaac ttccctgctc aaaggtttac  18480
actagcaggc agagttaaat atcacagata atcgtggcta taaagtcagt tggcctggct  18540
```

```
ccagtcaggg aatgaggggc caacagctgg gactggagtt ggtgaaggct ctggccctct  18600
gcacctcatc catcacaact ttggggcaca gtgcagaaca ttccccaaag ccacctctgg  18660
ctttgctctt gaccagcagc ctctccccta gtaggaagga actgtgacct ccacatgaaa  18720
ctataggaga aagttaacag ctcttcccct ccctctccaa tctgcacccc gtttgctccc  18780
tttttggatg gggacttagt taaaagaaca cacccaacat cctccaacac tcccaacttt  18840
ctgggaccac ctgattccta gaacatttct tttctagaaa aacttcggag aacttctccc  18900
cactttagcc ccaaacacag agtccctcac tgctgaggaa acttttcttt gtttcagcag  18960
gtcaaaggaa ggctcctggg gtgtgaattc atttccttgt tttgttagcc aggagggtgg  19020
ggagccaaag ctttcagctt ctctccctgc ccttcaccct ctgcttgcct ccattgtctc  19080
ccccaatttg ggtgattcct tttccacctt tgaccacccc ccagacacat cagtcctata  19140
aattaagctt taataatgta acggaacccc tcccatccct ttccaattgc acagaacttt  19200
gatttggtct ccattgatca caaaaatatt tgccttcaac tccagtaatt tctttctcca  19260
cttccacctc tcttactcta aggctccttc tgccttcaga gttgggtttg ttcatccagg  19320
gctggagttg gagaagccaa actcctggag gggagctgct aaaaaatgga gctctgtctg  19380
ctgctgcagg aatgttggct ctatcaggct cacaaatata atttttatat tagaccatgg  19440
tcattgactg ggtttatatg ccaatgaggc atttctggtt taccaaattt atgaaaatct  19500
cgctttaatt gataatcaca gatgctgtaa tttaagacct ccagctatag agctttcata  19560
ttaactgctg atatattact gtaaatcgtc tgaaataacc aactcctggg agcagagcag  19620
agagggagga agtgcctccg agagcgactc tctcccggcc ggccgcagaa acagcccagc  19680
ttccacatca ttttccgtga aaaatgattt atcgaagaca tggccataaa caacacaact  19740
cgctcacaaa cacacgcaga cgcgcacgca cacacacgcg cggacacaca cacacacaat  19800
ggctggcatg ccggctgaga agctgacacc catattgcta taaatcaaga aaaaggttgg  19860
aggacagagg gagagaggga gagggaggga gggagaaaga gagagagaga aaagaagaat  19920
attcctaaaa tctctatgca atgcctcaat gggcataaac acacagagca ccgtgtgaag  19980
agaaatggca ggaaatgaag atggctattt gtcacatttt acgacaataa cattaataac  20040
aaacaataaa tttacatgga catataagac gcggtaggta gtgagaaatc ccttctactt  20100
acaatacccc agcccgcggt gtggctccgg ctgcggggct gttttattgc tgtctccctt  20160
tctttctctc tctctctctc cctctctctc tccccccctct cttttttttt ctcggggtac  20220
aggcttgttt ttcaaaggac agttgaattg cacgtcagaa acagggagac cgagcctgcg  20280
attttcctga cgaatacata tctattctgc aacctcggca ttaattattt aatgaatcac  20340
gtgaccggga gggggaaggg ggtctttcga tttcaggctc aaaggaccac tatgaccttc  20400
cccttcagga ggagaaattt tcctgcaaaa taagttcccc ctcaacccac caatggaaca  20460
gtagtgaggt ctccgtctgt ctcccacact cacatccata cctactacat ctgcagctcc  20520
ctaaccccca tggacacaca cttacccaca gcccacctct cctctctccc ttctcctcct  20580
gcttctgctt agttcgtgga ggtgcagaaa tagtctgcag gggcgtctag ggggtggggg  20640
tggggtgggc tcagagccct tctccaagcc cctggatttc tcagcttcca gttcttctct  20700
ctgcatcctt taggattaag gttccctccc caactccatt ttttccccaa ctcctgggga  20760
tatttacttg agtgagaccc actccctctc ttcctaaata atggacaaaa tttctgaagg  20820
agccactttg aaaataaaca cttcataagt ccatggtata agtggataaa taatggggct  20880
```

-continued

```
tctggcttta ttctcgtttt gatcttttct ggtacctttt gaaggggcaa aaaagggaca  20940
gggtgaagag attactctgg agcttccaga gttgagaata accgcaaggg ggactttttt  21000
ccctgttgtg ttgttactac tataggaaat caaatgcgac tgaccgtttg aaaatagatt  21060
ctagagacaa agactgggac taaggtttct acacaaaaga atcggactgt cagcctctct  21120
ctacctatgt cacaccctgt ctcatttccc cccctcccca aacccaccag tgaagacagc  21180
tggagatttg aacaggagag gagggaaaag aaaagaaaag ctttgaagtc agcctggcag  21240
ccccaggatc cctatttccc aggtgttagc accccgagct tccaatcaac aaacaatgga  21300
ggctgatcag tgggaaaaag atgggggatg gctatgcctg ttaaagggtt aaataccagg  21360
gactatctat tccccaggcc taaagagaga gacacacaca gaccccttca actcaaatat  21420
aaacaaaata aaacaaaaac aaccccccat ccaaacttga ccagttacgt gcaactagaa  21480
tcagagttct cggccggggc atgggatggg gggtggggat gcaaagggaa gcagaaaaga  21540
cattcctgaa gaagtcgcag ccttatctgt cctcagcagc tctggaggca gccaggacca  21600
cagcctccgg ggcaggcagg gaatccagga agaatgagct tcagggtacg ggagcagggg  21660
tctgaggggc ctcccccggc ttgttcgaag gggtctaaac caaaagcaac tcagtggaga  21720
gaaggttgag gacccggttg tcttaacaag ccccaaagaa acagccaccc cggtgtcggc  21780
ctcggaggtt ccagctacag tggcagctgc acagcttctg ccccagctaa gagcactgga  21840
atctgctctg gcctcatggg gtgggggcgc cggccaggcc tggactctgt aggggaggtg  21900
gtcagctttg attgtccaga tacaaaacac agactggtat tgaattcagc ctgatcccga  21960
tgtgggccct gctcccggct ccagcgaggg caactccctg aaacgttctg gccacaaatc  22020
cattaaaaat ggtcctccag agaaaaacac tctgctaaag tctaaaatga aaatagagag  22080
agagcagaga gaggagagag aaatgctgga tgtgggaaga cagcaatctc taaaacggag  22140
aaataatttt taaggacaag aaaaagaaca gcaaaatgac acgaaggcac gccagcaggt  22200
tctgttaaaa tgaccatact cttttcggat cctgggaatg tccacgttca aataaacaag  22260
cgcctgatcg cgagccgagc actttcttgc tgccgataaa gcgaacgttt acactgtgag  22320
aaaggcgaga ttgatttacg aatctgaacg cgccagtttt atggctgatc acaaatccgt  22380
cagcgctcaa ctcacgctga gaaacttccc aactccgttt tccaaccaga cccccctcccc  22440
agctgccgct tcccagggag acccactgcc agcgctgggg ccgccttcaa gggctctggc  22500
agaactgggc aaccccctct gcccaggaca ggcgggtgga agtaggaggg agaatgggga  22560
gggccgaggg aactggggag aaagagggaa agaagtcaaa aggttgggag gactggagtg  22620
gcactaggat tgtctggagt gaaggaaatg ggagatctgg cagttcccct tagtgaaccc  22680
caggcttccc tgactatggt ctctctcctt ttccctttgg tgggccctaa tcctcacatt  22740
gcagaaagca gtttgtaaag tcctcggcga ctaggtcttt gtcacttgag cctgtagaag  22800
gcccacaact ggctatctgc ccttacaggt aatgaataca catctccctg agccccatat  22860
atttttagtc caggagcagc ctagctagct ttgtgctcat cctctgtctt tcctgaggcc  22920
tccagcccct ctacttatgc cacccaggga caaaggagag agtatcaacc actccagtta  22980
tttcttgcct gagatagagt ccccaaatgt caagaaacaa tttacaaaat gcaaaccaac  23040
aacccacata tcccagcaag gttctgtctc tcctagtctt aactgaaggg taacatttca  23100
tcttcccagc cagcgtctgt ctgtatctgt ctctctttct ctttctcttt gtctctgtct  23160
ctccctaaga gggtggctgc tggtgtggat ttttaagata cagcaaacag aatacagttt  23220
ttggaaaggc tctatgttca gggctcactg tttggcaaat ccttcaccta tttcttaaaa  23280
```

-continued

```
gtttctggaa actttggcta acctgggaca gcaggccctg gaaagtactc agaatagcct  23340
gcactgatcc tcctcccatt tcccttgctc ctctggtggg tgaggcactc caagggcttt  23400
tttcattatt gaggagattg agaattaggg gaaagaggta aaggtagtta tagaaatagc  23460
ttcctcaaca aatgaacttc agaaaatggg ttgacaggct gtggatttgg atgtcagccc  23520
tcagggagat gacagcctct gaagcaatgt tcagggcgga taagcccttt ctctcctcgc  23580
agcccaggag tttattcccc tggccctctg aagccttgtg gattaggccc ctccaacctc  23640
tcatatcttc tccctttgtc tttcttccct cagttccctc caggtgaaat agtaaagaga  23700
tgaactggac ctgggagtgg ttgcggggag gatggctgga gcctggactg ctgaaggtgc  23760
tgtgtacaga gagacagatt agcaccctac tttcgtcccc caactggacc cttgggctaa  23820
aaatctttac gttttttcc cccagtgggc agtaatagaa aaataatcca aaatttccaa  23880
aatagcaaag atgggtttgg ggcctagagg gggatggaga agatgggaca tatgatgggc  23940
caaggacccc tccctgcaga ggtgtgactc tccctcctgg gcaggaggca aatgccaaca  24000
caatgtccag tctcagcgag gtcaaggggc ttccgaggtc attttgtggt tctaatactg  24060
agctaatcgc ctagaaaacg tggcctctcc atgaactctc tctcctgcca gcctcccgcc  24120
tccaaaccct aagtgaggcc tcagggaaaa agggccaaca cattcaggtc ggctgcagag  24180
cccactgact ccctcagcct aagaaacagg gctgcagagg agagaacaga gacctcaaat  24240
taggagagca aagggaaacc aaaccaaacc aaaccaacat tgctcctcca ggaagaaggc  24300
tggggggaca gagcagaaga gaaatatttc tgcatcagtc caccttgtct gtgaactgag  24360
cagtttcctg ctccagagag tagcacatat ttgtctagaa tcccaagcta gacacaagaa  24420
gaaaaaaaag aacatatcca cttatacccg ctccaaagct ggaacattcc atccaagcac  24480
tggatttgat ttttccaaga ggcagcagtg acaacgtctc actggtaaac aggcataggg  24540
gacaccagta cccagtgtag acaagcagag tcacaggaac acaccgacca catgtggacc  24600
tcactagaca cacccatgca cacatgctgg ggctcgctgt gcctgcctgc attttccaaa  24660
accagaaaag cgcttctgaa ctgcctcaca aaacaaccgt cttctctggg gtttttcatg  24720
ggccctgaca cctcagtccc aaccagttca aacactctcc aggtgtcgag gcccctcttt  24780
ctctccctct gacccaagca tcagtcatca taaaagggag caaacctgct gaagcatcca  24840
ccataaaaac ccagccaaga aagttaaaaa agaaaaagga agaggcgaga gagtgtttct  24900
tctttcagtt gtgaaaagag ctcataaaac gatcaaaaca cgccagcccg ggcccgggct  24960
ttgttacctt tgcgcctctc gcctcctctc gcccgaactc tgcagatccc attcatgacg  25020
aagggcttct tccaaactga gagaaaaaag ttttcaactt tatggttcca aattttttcc  25080
cccttgcaga tccgggagag acggctaaca ctttttttccc ccaacagccg gtccaaggag  25140
atttgctgtt gaataataac aaaggagaga ggatacgtat ttaaagaaaa gaagtgatta  25200
atggttttct gtataattct cacattttttc ttagctcttg tctacacaga atggctgtga  25260
actttaagct ccatagaaat cttttttttt taaattctat tcataccttc caaagagcag  25320
ctttgatttg gttctttaga gacattcctt agggggggcat atgcttttta agaactattt  25380
tccccctcaa ctggggctgc ggcatcccct tgcagctaaa ccaccacacc gcaatccgac  25440
cgaaataaag ctcgcccctc tcatcctcca ggtccacgat gattttttta cgagtctccc  25500
agcagcattt aaacggacag ttcagcagct cttttgcggc tggggacacc ggcctgtcgg  25560
ttccccctgc cctacccagc ctccaactac cggagctgca agctggagga atgcaaaata  25620
```

```
aataacaata aaacgcgcgg gtgggattgg ttctttttat tttctgaaag gagatgggac  25680
tgaaaaaacg acttttaatt gcatatgctc tcccgagccc cgagcttttt ggagatgtgg  25740
tggctgcacc ctggatgacc aatagaccag agaccctgag gctggagccc ccagacctta  25800
gaacttccaa gcagtgctgc acaaaagcaa tctgagcctg acagagcttc tgagggtcac  25860
ctgcacccct ttcccctacc cccactccat tctaggggtg actgggacct cagagacaga  25920
aagctatttg gtccccagtc atactttcga tactttctat gagaaagaaa atgaaaatta  25980
atactggagc aaggcttcac aaaagaggcc atttgtcttc ttgattatct atttgcttgt  26040
cagagtttga gctatggcac tggctagctt ctttgtaata taaaaatact ctgaaaacct  26100
gcaaacaccc agaaacatct gtgcaaaaaa ttatactcat taaagcctta aacacctcag  26160
aggaaagcga taccttctta tgctgcgagg aaagaggcca gcctcatgga atcctctctc  26220
ggaactttaa taaccaaaga gccttctgtc taaaaggaga cagcttaacc gcattttatt  26280
tgcttatgac aaataaatca cgatatgaaa ggctttgccg tacttaagcc tcttgtgtcc  26340
tacaatgaaa cattttcccc cattagggac tggaatcagc cttcccagtc ctttcaatcc  26400
atttttggac tgaagggaaa aaattaaaag ccccaaaaca aaacacaccc accctaaaag  26460
gaaaacaaac cagccaccac aatttggagt cctctgagat aaaaattccc atcagactct  26520
ttgaaaaaaa tcttcaacca cacacaatgt ggggctgaac ccagtagggt gcttaaaata  26580
tacactgggt ggcatttgtc catatcttta cgccaatgtt tcaacaaaaa cacgctgtgc  26640
tggtcacaag aaaccaaaca tttatttcta ttgtcactct gtacagcaca cagatattca  26700
cacatacgaa gggttctaga ctcaagcagc cccagaggta ggaaggggcc tggttttgga  26760
atgtcagaaa gagaaaagga gagaggactc acatgacaca aaaaaatagt aataataata  26820
ttatcaataa taataataaa cgatgcaaca taataaacta tgggagaggg ctctgcaaca  26880
tcctcctccc agactgggag gggcacattt tatttcctag tttcacattc attttcagtc  26940
taggagagag gcttctgctg tacaactctg gactggcaga gtagtgccca gctcccagaa  27000
ctcaactggc ccctcaccct gccaagcatg gcttggcttg gcctttcaga ggaaggccct  27060
cccgggtctc tgagtctctc tttttccttg gactcaattt tcctgctcac tcctgagttg  27120
tcaaggccac ccccttccct acttgctccc ctcctctgtt gcccaccccc aaccccacgg  27180
tggaagtggg tgagcagtca ttctggccct cagtgaatgg gcacgaaaga tgagggagag  27240
tgtgtgtgtg ttaccgtgac caaaacactg cactatctgg cagtcagagg gtgctttcgc  27300
tgggtatcgg gagtggggga caaagaaagg aaatccaggc tgtcttccag cagcggcagt  27360
agcagaggcg gaggcggccg agccgggcct catttgttag cgggtgtcga ggtaatggtc  27420
gccaccgagg cccgtcttct cctcggcaga ggaaacaaga cagatgggcc tggacctggc  27480
gtgattaaag atgaaacgtg gatccatctt cgccaaagct gaaaacgagg agctgcagcc  27540
tcctcctatt tctctttctg tctttttctt tcttccttct tcttgctttt tctttttctt  27600
tttttaaga aagaaagcaa gagatttgaa tcttgcttct ggggggggcct ccccgtggcc  27660
ctctattgtc atttctataa ataaagcttc ccctccccct cttctgcgtt tattcgtata  27720
taaagtgtgg gggagggcag atagattttt ccggggccca ggccccaggg ccccctcctg  27780
tccccccacc ccatcccctg cactcactgc ccaccccac cccgaggttc gtggctcccg  27840
cgtgcggggg cactagagcg cgcgggggcc tccattgggc cggccagggg gccctccggc  27900
tgagcctgcc gcaccacccg agcggatctt ggtgttgggc aacttgtggt ctttttccca  27960
cttcatgcgc cggttctgga accagatctt gatctggcgc tcggagaggc agagcgcgtg  28020
```

```
ggcgatctcc accctccggc gccgtgtcag gtagcggttg tagtgaaatt ccttctccag  28080
ctccaagacc tgctggcgcg tgtaggcggt ccgagagcgc ttgggctccc cgccggcgta  28140
attggggttt actggacaca cacggagaga gggagaaaga gaaagtttta ttgcccccga  28200
aagagagagt cctttcttcc agggaacaca gcgtttccct ccctccctct cccgccacct  28260
cttcttcctt ctgagggaga gcggggaaaa acgaaaaggg aagaatgcaa gacccaagaa  28320
tgagaaagag acctccaagt tttggagggc tgtgctgtgt ccttgtttgg gtgtgtggtg  28380
gggaaggggg gcgtgtgagg actcccccaa ggttttaatt gctcctctct ccccctcagc  28440
ttggggcccc cagaatggga gaatgagggg gtggaagagg gaggggaggt ttccctaaac  28500
ctttcctctg tttagttccc acccttgctg ctcagattcc aagcagtgcc taccccctact  28560
gaaaactttt gctcacttct ccagccaagg agtcagactg gaagaaagga aaaaataaat  28620
actgggagtt gactcaactc tctgcttaaa tacggattac ctcctcctcc ttctcctcct  28680
ccacctcctc cacccctccc caacttccaa cttcattaag actgtatctc cctggcgaaa  28740
aagtcgctgg tgagaatggt gaagaggatg gggaacctac ttcaaaggcg cagggcccac  28800
caggccataa aaatttatgg gggatgtaat tatgtggctc tgaaaacagg cgaccgtaaa  28860
tctccggcaa tggcgagttt atagcgggga caattggctt ccccagctca accccccccc  28920
aacccatgcc tccgaagtcc ctttggtgta aagctccagg ggtgggaggg ggaaggggtg  28980
cccacgcact cacccgtgct cacgtgaact ttgcgcatcc aggggtagac gacgggctct  29040
ttgcacgcgg agtgggacgg gctggggtgc agggggttct gggcgcaggg aggcggcggg  29100
gggctgctgc tgaccgcctc gcagcgctgg ccgggctccg ggaggagggc cccggcgggt  29160
ggcggcgcag gagcccgagg ggacagaccg ggcggtggcg ggggcggcgg gggtggtggc  29220
ggaggcggcg ggggcccagg gtcccggcag gccgcgtagc gctgcacggt gcacgccgcg  29280
cgccgcccga agcccgcctc cggctggaag ctgctctctc gcctctggcc gccggcgtag  29340
tacccgggcg agtggtcgct gggtaggtaa tcgctctgtg aatattcctc gcatggaggg  29400
aacttggggt cgacatagtt tgagttgatc aaaaaagaac tcatagccat taatttctgg  29460
gaattgccca caaaatatac taaaatttat tccgacccct gactcgtttt cctgtttccg  29520
aaagccctcc tacttactgt caagtgaaca aagttaggcg cccacgtgat cctccgagcc  29580
aatggccgcc ccgcctgcga ttcccggata aggaaatctg ctcacccgga ccccactcca  29640
gccaaagagg tttatttccc cttcttccct tccccctccc cacccaccca cccaacacca  29700
ggatttacat agggctcctg cggggcgacc ccctccttgc ctcgctctct ccgggatcag  29760
agagagagcg agagagagag cgcgcgcagg ttgcgactgg agggcctgtt ggggcgctag  29820
gcagagcgca aaccctagat cccttaagaa gttggggctc ccggtgtagc cctcctgttc  29880
tgcctcacct ctgcccagca ttctgtacct tccaaaggcc ccagtctcct cccctcggcg  29940
ggagggagcg ctagcaccct gcgtctctat ggggagttag gttactggcg ggttgggggc  30000
tccgtctcga aaggggaacc catacggggg ccagagcaca gagcttgggg cttttctctg  30060
cagctggatg gggaagggta ggggtgagag aggaggcgtc cagagctaga gggcgggtgc  30120
gcagagggac ttgtcagaga tgaatggaac cgcgggcgga tcgataggaa attcatgcac  30180
taattcgggg agacttcgcc ttccaaatct catttagctg cacggttagc tagactgtgt  30240
ccgtcagtcc gtctgtcccc cttctcctat ccactcctcc ctttaaccca cacggcccaa  30300
gcctggagaa acgacttggt ttcccacact atagacagag cgctggggta aaaaaacctg  30360
```

-continued caacttttga gagcaaaatt gattagcaat ttgctaattc cataaccacc cgagcaatac 30420
taaccatggg tccgagacgt tctaattgtc gccgcctccg cggcgaatag aaatctcaca 30480
tccctttgat actggggata cagccataga ggtgacccac acagacaata acactccttg 30540
gtaatcgagt atttccaggt catcttgttc tgaactgaaa cggaaaggcg gcctcagcat 30600
ccgtttgtta aacaaatttc ctttgccttc ttcgcacact gaagacaagt cattttttt 30660 cgcaatttcc aataaagcct ccctgagccc agaatagaaa atgggtgcgt ttgggacgag 30720
aagataaatt taaaacttca acaacaataa cattaacctc ttaaagagat gtgaaaaggg 30780
accaaggctc ccaggggcag gcgtggggag agttcaggta gatgatttct ccatctctaa 30840
ccagttgaag gaggaaaaga tagaggaata aagaggaagg agtcttcgtg tggccagtca 30900
ccagactgtc ctcattcaga aaaatactac atatacatat atatatattt ttttcttctg 30960
gaaaaataag agcggagtgt ttatgtcaac tacatattcc cctagatacg aatttgtgac 31020
cacaaaattc cttacacaaa ttcggatcta cagggtatat acagaagaca gacagatctt 31080
cttggcccag aaattttcca gttctcctac tttccgcgcc ttcttcgttt ggggtgtggt 31140
ttgagtgctt tggttttatt tcgttttgtt ctagttttga gctctgggaa cagaaaaagg 31200
cagtgcgagt ctgttcttgg gattacaagg ttttcaattc tcctcttcta ttagaatttc 31260
aagtagccag ttcgcaaagg gacgagaacc ttgcctccgc cgccgccgcg caactctcgg 31320
tggcgcatga attatgagat gtaaacatta gctaagcaca aaaggaggaa gggtcattct 31380
gaggctgcca cgaagtcaga ttcaggcctt tctgggtgcc ttcgcgcccc tcccctcccc 31440
ccaggacttt tttttttttt tttttttag aaaaaacaaa accccaatcg gctcctccgt 31500
gcccctccaa gcctttagtt tgtgatcaaa cgaatatcta gatattttcc aaagcgcctc 31560
tcagcgaagg gaggaggaag aggcggctgg gtgtgaaggt ggtgtaataa aagtcctttt 31620
ggaaaaattc agtggtaaaa agagagagaa acagctgtaa agaaaaatgc tgggagacca 31680
agcagatggg gccccggata tttaatgacg ggcaattccg tttacaacct gagaaaagat 31740
caaaggcgtt tcatttccga atgaagggca atgaggaacc ataaaagatg cagccagatg 31800
atatagggcc cctcccagcc tctcacacat cctgggagcc aggagagagg gtctatcccg 31860
gggaggtgtg gggaggaacc ccatttcccc accttcctag ccccagacgg gtcctttcct 31920
tctaaacaca tatgaactcg cctagccacc tgcttgggtt gctggtggta gggccaaaat 31980
gggcatctgg ggtttacgaa ccaactttct gaagctccca gaagccgtga atttactaag 32040
ctgagagtct ggggattggg ctggagggaa ctgagactgt gaaagctgtg acagagtaag 32100
ggaaaatgtg catagaaaaa gcctccaccc cacccagact ccctactcaa ctccctaggt 32160
ctgagaaata cttgcatctt tagtgaggaa gtcaaaataa tatcaatttc attaacaaat 32220
acaggaacaa cacaaaaaca accctctaac tgcaacactc cagagatctc tgcctatgcc 32280
cagtcctggg accttgcagg tgggtaggag gagagttccc acctgcccac aactaggtcc 32340
agagaccctc tgattttctt ttaatcttaa atctaggaat tgccaatgtt ggcctctggg 32400
cctgatttct aacatcaaca ttctcccaga caggctgaac tcacacatat ttgggagaaa 32460
aaagcaaact atcacactat ggttgtcttt gccaagagag ggtccaatag gtaatctcag 32520
acccccatct gggcactcag ggagactaga gtctggccca gggcccacag acaaaatgcg 32580
ctgctaggat ccccaccagc tccctagcgt caaccaggga cctttccaaa tcttgtcata 32640
ggccacttag ggtctccagg acccactcca acggtccagg cccctccccc accccatacc 32700
tcctgtcctt ctcaactcgc cagctctcgg aaacccgtcc aacccgtcgg catttcggaa 32760

```
gtttgggagg gccgctgggc cggcggccgg gcctctctgc tgctctacac ttcacaaggg  32820
atgcggccca ggtgccccag caccccaaga gagaggaaca ggcggcagag ccaccgcggg  32880
tttgggtatc cttgatcctg gcgcccaaga gcagagattt ttctcctctg cgccctggaa  32940
gtcaccacct gccaatccca ccaaggcgcc gcaccccccct caccccctcca gccgcctgag  33000
atggagaaca gggtttatgg gcgactccca ggacgggttt caccggagcg ggaggctgcc  33060
tctccccttc accgcccaga aggatacgaa cagcaacacg cataatagta aaataagagc  33120
aggggctgcg cgcgagctga gccacctccc ctgcgctccc gggtctttcc gtggcttccc  33180
agccgccttc tcctggcagc cacaggttgc tagcgtgacc tcgcccctcc cagccaccct  33240
ccgccgtcca ggcgtgccca gtccgctagg aatcatcacc ttttgttggc ggggagaagg  33300
gactcagcga gggagcgaaa ccgaaggccc gagcggaggc gagtccccag ccggcctgcg  33360
caccggcggc ggcggcgcgg aggagagaaa ggcccagagg gggcgcgggc gagggtactc  33420
accgggaggc tccccagccc cgccggccgc cgagccgccc gcggacgcgc cgggcaacag  33480
ctgagctctc tcctgtccac tattgtgtgt ccggaaaacc ggaccgcggc ggcggacaca  33540
gccacgggct ccctcagaag ccggaacgtg actttttttt ttggtgtgtt tttgttttgg  33600
aagcgcaagt tttcgtgtta atctcatact ttggcagtct ttgttaaaca gctaggcgcg  33660
tcacgaggct ctcaaacatt ttaataattt ttagacgccg tgacctgcgg ttcacctctc  33720
tcccagcctc ccccacgagc aggcagttac tataatatgc tcgcgcagtt cgctgggtca  33780
tattgaattt tgcgtaggtc attacttggg aaaaaaatga cagagcagaa atttgattca  33840
gctcatcctc tccagctcga cttttcgcca gagccttctc ttctcttcat ccaacccccca  33900
cccgaaaaaa gtcccattcg gataggagtc agtcggccac gcccctgttt tgattttcca  33960
tcattcccat attttgtcag ctcgggttcc agagagagtg tggggtttca tgtgggatcc  34020
ttttgaggcc tgagaatgag gctggcacgg ggaaaactga aagcatggct ttgggcacct  34080
gggccccaga gagcaggcct gagcaagagg ccccttccct gaaccttacc cctaaatgcc  34140
tgtatggcca gggcccggat ccccacccca ttgcacactc catctgcttt atttgctccc  34200
ccaagtgtca gagatatcct catttctaca aaagctttgg aagctccagg gcctagaaat  34260
gaccactcca cctcttgggg ccaagatttt ggtccacaca acccagcagg tttggggaag  34320
atagaaccct gagagaggtg ctgggctggg ctggtcaaag ccggcgacat aactttcaga  34380
gctttaactg tcctttaaat acaaaacaat agcttccccc tccccccgaa gaatcgttct  34440
catcaataca gtaacacttt tgcctacccc catcacccac acaaggaggt tcaggagcag  34500
atcaagaagg catttaaaat agtgagattt tcttgggttt gtctctccag gattagaatc  34560
tggtggattg cctacaacac acttctccct ttctccagct tcctagggtc ctgcagaggt  34620
gggtcaggtg actccctttc ctcccaattc aagtctacag actgaaacag ggctccagcc  34680
tagttggtag ggtggtatcc tcctagtacg gagaggtcaa gaaagaactc cccaaggcac  34740
ccagcttggt ccagaatggc agaggccact tcttccccat cctggtcctt ctagcccagg  34800
accttgggct gctccagtct atacctaaat ttgctaacgt tctgtgctgg aacagaagga  34860
gatggattct tcagttcagg ctttgacatc tgtctcttca ggactccagg aattccttcc  34920
tggcctgaca ctgcagagaa actcacctaa ggactaagca gaaataggga ccttcaccca  34980
attggtttag tcaaaaccct gggttaaatc tatttgaaat ttgatattaa acctttgtct  35040
cttctggcca tgtttcaaaa ggcatcttta cagaaactct caggttatct ccatcctgga  35100
```

-continued

```
aggaaaaacg cccacagtgt acctcctata gtaaatgctt ggaagagcag ataatgacat  35160
ctcataatac aacagtcatt taaagaccca aaatagacat atgccccagt gttataatta  35220
ctgagtctct ctaggcattt gctcatgagc taagtttaat gtatggattc aaagttcatt  35280
tcaggttgtc tgtttcaact cccgtaaaaa agatctccgt gaggccattt ggtatttttc  35340
ctttgcattt ctcctccctc atccaaatag gaagagaagg agtcaagatg aacacacaaa  35400
tggaggcttg ggagagagtg agagaattaa caagctaatc tttcagtagg caagttctta  35460
aactggagca atttggagag aggaatgaga gtttggaaag gctccagtgt tggcccatgc  35520
tcatggaccc caccttcctg acacagcctg gggttaagg gttcttgaaa acaggcctgc  35580
ctctcccagg ggtggaggat tgaaagagcc agtagtttga cccctttagg gcaagcagag  35640
tgagttgatg ttggtgaaaa tcaaaccttc acattggaag tattctttgg ccctgccaga  35700
agtcctacaa agacgtgggg gtaatttaat tgaatttcta aaatgtgtgt ggctaggaag  35760
gttttaatta aatttaatat ggtgactcaa agattatctt tggaagagaa aattgctcag  35820
agggttcacc acacccttaa gcgctgtctt ttctacaact caccaccacc accaccagtc  35880
tcgccctttt tggagaaggg atttttcctt cctcagtttc ccttccccag atatctgcct  35940
cttcgctgcc catttctgct cccccacttc tgcaacccac aagtcttcct tacctccagc  36000
atcccaggct ccctcgtccg tcttcacaca catacagccc cctcccccac cgccccaccc  36060
cgcccccgcc gctagtcgcc tccgccgctc ccactcacgc atggtgtaaa cttttgaccc  36120
tccaactttg cgacccctcc ggcaataaca ctggcctcac cacccagggt ctcattctgc  36180
tacgcgccgg ccgcagaaac cccagggcaa aacgctttcc ttacccctcc ccccttcgcc  36240
aatgtcccta ctaccccaga gccttagacc tgggcaagag gagtcttttg actattaaat  36300
aactccttgg aaaaagacgc ggaacccacc tcccgcattt tcagcggtct cttctattgg  36360
gatgcctgga agggcttttg accacccacc cttcttcatt tttgacaccc gagtggggcc  36420
gaggttgccg gatgaggaga cctatggcga gcagtagaat gggctgacct ggagaagggc  36480
atttctgggg tgaagggtgg agagagcttg gagcaggggc tcctcgggag cagaaggggc  36540
cgctgtgctc acagggctag agggagagtt cagtgtccca acgatgcggg ggggcccggg  36600
gccaccttgc gcggccgctc gctgacgcct cagaggcccc agcctggctg tgaacttggt  36660
ctaaggcgga ctctactggc agctccggga tgttacagcc tctgcctctg gtccagagca  36720
gcggcggtgc ggacaacccg tgcgctttcg gtttcccttc cgcccaaata tcgcctccca  36780
gacccccacc tctccctggg aaggatttcc tttctccctc cttgggatcc cttgggattc  36840
agaaaacaga aaagaaaacg aattagagag atgcatgcac ctaaggacaa gcctgcagga  36900
gccccgaaat agggtatcct ctatcatgcc tccaaatccc tcaagaggcg acgccccaca  36960
caggctggca ctttccctcc acttctcccc taggtgtgcc tttccgtcct gactccccac  37020
ctttccaact ggcctgggtc atcttttggt aaggcaaaat ggtctggggc ctgcgaggta  37080
cctttcctcc ctagatgcat tcagccctac cccaccgggc tccgaggtca gggatccagg  37140
gatcgttgcg accaaaacca gccgctgtgc tccgaagccg caaggctcag cccggatcca  37200
ctaggggaga ggcagtccag agggcggcct cgcagactgg gaactgtttc cggggaggag  37260
aagctagagg atactgcaga gagtgcattt ttctctccaa gaggaacttt agggggagaa  37320
gagacaagag aggagacgcc taaatcactg agaaaaggaa taagaagaga gggaagagaa  37380
acgttaaaac ttggggacaa ggtgcttttt gggatccgac aggttcccga attgcccgaa  37440
gtccaatact ctccaggctc ccaaatttcc cctcttcctc ttggagcctg caatcagtaa  37500
```

attcgccaaa agaaagaacg aaagatccgc ctaaacctgc cggcgtgccc ccaccccccgg 37560
tctacagagg cggaggtggc tgcggcggtg tggccggcgg cgcgtaatgt atgctgcagc 37620
ggctcggagc cccacgtagg ccggcgctgc tgcccccgtc tgctgacctc tgcatgatcc 37680
cggactctat gaattattga tgagatatga gcgttgattt ccccctttcag gatgcaaact 37740
ccattatatt gttaaaatgg cgatttaatc gttgagaata gctttggtgt gggtttttttc 37800
ccccaactca tttgcgcctc cttcctttttc atttaactct cttaattaaa tcctttaaca 37860
gattttaatc actttttgga gggagggata ggagaaagga gaaggccata agaccatcac 37920
taccaacaac aacgggacgc taaagcaaaa taaaacaaac caaattcgaa aaccgtcata 37980
agcctctacc tttgagaagt cgaaaggaag gtgagggggg aggttaaccc ctctagaaag 38040
gatgctcact aacctctgct ggagacagag cattagaggg ctggggaaac ccaccagaga 38100
caaggaagag tggggtgggg cctgcaggaa cgacctgagg ggtatttaat cccccacccc 38160
gccaaccatt accaccatga gacttgtgtg tggagttgac tgtagagact aagtcatttt 38220
tgcccttgct gagaactcca ggggcttcaa gcctggggag ggccacagga ttcatgtgca 38280
gagggccctc caatctcaac ctcagagtcc cttagggaga aatatccatt ctgcttaagg 38340
ggcccccgtt tttcccttcc cctccccaaa cagctccgtt tccaggcggt gttaattaat 38400
atggatgtgt aacagcgctg cagcaatcaa taagtctcac tgtgggcaga tctcagcctc 38460
aaaatccgat tactctgaaa aactccaaaa atggggaggg ttaccagtat cccctccctt 38520
aaaagagggg agctcattct tgctagccct gtcttccgag attgaccagg ttggtccccc 38580
aagctgagaa gtccatgctg ggagactag ccctgggaag ggactgagtt tggggggggtt 38640
gtgctgagct tctgtcttct ccattgctca gaatccttgg cctgcaattc ccagggataa 38700
aggaaccagg caaggaaagg agctgcctct tagatcttcc cattctgctc accagccctc 38760
agagaataac ttctcacagc cagggaaggg ttaagtgtcc ctgccacagt tatggagagg 38820
aagctgatga aatatgggca cttggaactc caggcccagc tggctttcct gtttacactt 38880
ctttatactt cctcccaccc attggcctca gagaaacaaa acaaaaacaaa taaccaaata 38940
aaacaaaaca aaaaaaatca aaattgaatt gtccaccgag tggtggccag gctggcctca 39000
gagggaaaag agaaactgca gccttaatct ccagctgtca cctcctgggg cctgccccag 39060
gttgaagatt tggccagagg gtaccggctt ggcttatagc tcaagaggtt gaagcctgga 39120
ctggcaggga gagaaagcag gtgggagagg agggagagca aagccctgga gagagtagag 39180
cagctctctt agagggagac agcctgggag ggcaggagga gaggacagag gtctggggca 39240
gaggagagag ttcttggcat cagaaatccc ttcacacctc tcattgcctc ccgcagcttg 39300
tcctgactgg ggttcagaca ggactggggt tcagctcagg gagcctgaag tggagaagag 39360
gaaagcccag cctagggcat cttctccagg acctgcttag agctggagga gacccttcaa 39420
gagtttgttc actgaggtgg aagtgggcac cccaatttgc tctttgccat cctggaaaat 39480
ccgaccagat atgcctagta gatgttagag cctacagaac tgacatgaga gggggcaaag 39540
aaacaatttt tcaggagcag gccttactat ctggggttct agcttccaga agggctttca 39600
gaaagggaag tatattagag tgaggccagg ggcacaatag gaatggggtt cccctggaga 39660
cccaggtcag actctccctt gcagagctct ttgtctgcat gtctgtcaac tccgttgcct 39720
tgtagagtgg aagactgtgg aagctgtgcc tccagcactt ctttatattt tcagtggtgc 39780
tggggatcct ttgggagatg acctgtgtct cctttctaag ggatacaaat gccctcatca 39840

-continued

```
ttcttgggat gatatgtctt caaaccaggg tgactctgct cttaaagcct gttaaggatt  39900

tcctgtaagt caggcttggg cagtggatag agagctcagg gaatagaaag tggcttcagg  39960

agaaagagga cagggggaga actccaatgt cccttaatga gaaaaaggga gtcttatgac  40020

cccatccttg tcccaaagat cagaagcccc tcgaggtgcc acatatccaa tcccagaaac  40080

tacctatggc agttggtgag ctgaatcaag ggatggcagg ctggtgaaag taggagtgac  40140

agggtagtta gccccacggg tgttaaattg gaggggggtc aatttggtgg ggaagaagcc  40200

tctgactttt agaagggtga cttttcccta gaaaataaca gaacccctgg ggatcaaatc  40260

ctgaagtctc tctggtttat ggttctacaa aacaaagggg actttgaggg tgtgcccaga  40320

aaagaagagg gaaaaagaga ggaaaaaaga gcacctttcc tattttctct tccagctcct  40380

gaatctattt cctcccgaca gttgagggat ttgtattctt gagctgattt tatttgagga  40440

gggcttgcca gagttctact taaacaccta acacctctag gcaagagaag aagctcttcc  40500

cttcccccac tcctggttca ggaattaggt tttgaattgg gggaattgcc ctctctgtct  40560

gctccctagt ctgacttcag gatcctactt cgagccaagg agaaagatta gcttgagacc  40620

aacaggctga aggtggaggc aaaagcagcg ctgtgctccc catcccagag aagcctgatg  40680

aagccaaaga taaccggagg gacctctttt tatgggcttc aaagatcgga aagccagaga  40740

tcaccccagg gcaaggtagc ccacagcagc cgcctacccg gtgctttttc tcagctcaga  40800

tgtatccaga taaaagtgcc cagcggtgca cccccacaca cctccgacaa atgaatgtca  40860

taaagtttct ttccggagga tggggggata gttgtctgaa gatatccagc agtgaagtgg  40920

cccccaccaa tggccccttc tttcagcaat atacacccct ccttcctggt ccctaaattt  40980

ccgctggcac tgagggagca tggatccccc acacaaaccc ttttccccac aaagtcagac  41040

actcctgttg gtaaaaatca ggcacccccg accgatgagg ccttaagaaa ctgagagcac  41100

tcatttcagg cacccagtcc cttagaactg ggtgcataaa acaggctaaa tttcccctac  41160

atcaccccac agccccaggt ggaaacaagt tttcttcccc cagtcccagg ccccagaatt  41220

gcaaggggta aaagcgaaag ctgaaagcga cttactgcgg gaatgctggc ctgggccgcc  41280

gctgccttct gggctggtcc ggctgctcca ggctgggaga gtgctcacct acctctgccc  41340

ccttccccac cacagcgagc agttaaagtg tcacttaaca ttctggagaa tgtgaaatat  41400

actgcgcggt gtcaactccc caaaaccata aaactaactt tatggacctc acgtgacttt  41460

ctcgagccag tgaggggtat ctgtctgact tctcggcgat                        41500
```

<210> SEQ ID NO 27
<211> LENGTH: 20
<212> TYPE: DNA
<213> ORGANISM: Artificial Sequence
<220> FEATURE:
<223> OTHER INFORMATION: miR-10b-G1 sgRNA

<400> SEQUENCE: 27

```
cctgtagaac cgaatttgtg                                                20
```

<210> SEQ ID NO 28
<211> LENGTH: 20
<212> TYPE: DNA
<213> ORGANISM: Artificial Sequence
<220> FEATURE:
<223> OTHER INFORMATION: miR-10b-G2 sgRNA

<400> SEQUENCE: 28

```
cacacaaatt cggttctaca                                                20
```

<210> SEQ ID NO 29
<211> LENGTH: 20
<212> TYPE: DNA
<213> ORGANISM: Artificial Sequence
<220> FEATURE:
<223> OTHER INFORMATION: miR-10b-G3 sgRNA

<400> SEQUENCE: 29
atagacaacg ttacaacctc 20

<210> SEQ ID NO 30
<211> LENGTH: 19
<212> TYPE: DNA
<213> ORGANISM: Artificial Sequence
<220> FEATURE:
<223> OTHER INFORMATION: miR-21 sgRNA

<400> SEQUENCE: 30
tcatggcaac accagtcga 19

<210> SEQ ID NO 31
<211> LENGTH: 20
<212> TYPE: DNA
<213> ORGANISM: Artificial Sequence
<220> FEATURE:
<223> OTHER INFORMATION: miR-107 sgRNA

<400> SEQUENCE: 31
gagttcaagc agcattgtac 20

<210> SEQ ID NO 32
<211> LENGTH: 20
<212> TYPE: DNA
<213> ORGANISM: Artificial Sequence
<220> FEATURE:
<223> OTHER INFORMATION: miR-139 sgRNA

<400> SEQUENCE: 32
gtgtctccag tgtggctcgg 20

<210> SEQ ID NO 33
<211> LENGTH: 20
<212> TYPE: DNA
<213> ORGANISM: Artificial
<220> FEATURE:
<223> OTHER INFORMATION: miR-10b-F PCR Primer

<400> SEQUENCE: 33
gaccctggca gaagaatgag 20

<210> SEQ ID NO 34
<211> LENGTH: 20
<212> TYPE: DNA
<213> ORGANISM: Artificial Sequence
<220> FEATURE:
<223> OTHER INFORMATION: miR-10b-R PCR Primer

<400> SEQUENCE: 34
tgaggagctt ctggagagga 20

<210> SEQ ID NO 35
<211> LENGTH: 20
<212> TYPE: DNA
<213> ORGANISM: Artificial Sequence
<220> FEATURE:

<223> OTHER INFORMATION: miR-10a-F PCR Primer

<400> SEQUENCE: 35
gcgcggaaag taggagaact 20

<210> SEQ ID NO 36
<211> LENGTH: 20
<212> TYPE: DNA
<213> ORGANISM: Artificial Sequence
<220> FEATURE:
<223> OTHER INFORMATION: miR-10a-R PCR Primer

<400> SEQUENCE: 36
ctaaccatgg gtccgagacg 20

<210> SEQ ID NO 37
<211> LENGTH: 21
<212> TYPE: DNA
<213> ORGANISM: Artificial Sequence
<220> FEATURE:
<223> OTHER INFORMATION: miR-21-F PCR Primer

<400> SEQUENCE: 37
ggttcgatct taacaggcca g 21

<210> SEQ ID NO 38
<211> LENGTH: 21
<212> TYPE: DNA
<213> ORGANISM: Artificial Sequence
<220> FEATURE:
<223> OTHER INFORMATION: miR-21-R PCR Primer

<400> SEQUENCE: 38
gagatgaacc acgactagag g 21

<210> SEQ ID NO 39
<211> LENGTH: 20
<212> TYPE: DNA
<213> ORGANISM: Artificial Sequence
<220> FEATURE:
<223> OTHER INFORMATION: miR-107-F PCR Primer

<400> SEQUENCE: 39
ttacagtgtt gccttgtggc 20

<210> SEQ ID NO 40
<211> LENGTH: 22
<212> TYPE: DNA
<213> ORGANISM: Artificial Sequence
<220> FEATURE:
<223> OTHER INFORMATION: miR-107-R PCR Primer

<400> SEQUENCE: 40
gaatcttgca atgcttcaaa ac 22

<210> SEQ ID NO 41
<211> LENGTH: 23
<212> TYPE: DNA
<213> ORGANISM: Artificial Sequence
<220> FEATURE:
<223> OTHER INFORMATION: miR-139-F PCR Primer

<400> SEQUENCE: 41
cacctctaca gtgcacgtgt ctc 23

<210> SEQ ID NO 42
<211> LENGTH: 23
<212> TYPE: DNA
<213> ORGANISM: Artificial Sequence
<220> FEATURE:
<223> OTHER INFORMATION: miR-139-R PCR Primer

<400> SEQUENCE: 42
ctccgagcca cactggagac acg 23

<210> SEQ ID NO 43
<211> LENGTH: 23
<212> TYPE: DNA
<213> ORGANISM: Artificial Sequence
<220> FEATURE:
<223> OTHER INFORMATION: NTAN1-F PCR Primer

<400> SEQUENCE: 43
cctgtagacc aaaatttgtg gag 23

<210> SEQ ID NO 44
<211> LENGTH: 23
<212> TYPE: DNA
<213> ORGANISM: Artificial Sequence
<220> FEATURE:
<223> OTHER INFORMATION: NTAN1-R PCR Primer

<400> SEQUENCE: 44
cctgtagacc aaaatttgtg gag 23

<210> SEQ ID NO 45
<211> LENGTH: 23
<212> TYPE: DNA
<213> ORGANISM: Artificial Sequence
<220> FEATURE:
<223> OTHER INFORMATION: 5NTC-F PCR Primer

<400> SEQUENCE: 45
ctacagaaat tctgttctac tgg 23

<210> SEQ ID NO 46
<211> LENGTH: 23
<212> TYPE: DNA
<213> ORGANISM: Artificial Sequence
<220> FEATURE:
<223> OTHER INFORMATION: 5NTC-R PCR Primer

<400> SEQUENCE: 46
ctacagaaat tctgttctac tgg 23

<210> SEQ ID NO 47
<211> LENGTH: 23
<212> TYPE: DNA
<213> ORGANISM: Artificial Sequence
<220> FEATURE:
<223> OTHER INFORMATION: FLRT2-F PCR Primer

<400> SEQUENCE: 47
aaagaccatg ttacaacctc agg 23

<210> SEQ ID NO 48
<211> LENGTH: 23
<212> TYPE: DNA
<213> ORGANISM: Artificial Sequence
<220> FEATURE:
<223> OTHER INFORMATION: FLRT2-R PCR Primer

<400> SEQUENCE: 48
aaagaccatg ttacaacctc agg 23

<210> SEQ ID NO 49
<211> LENGTH: 23
<212> TYPE: DNA
<213> ORGANISM: Artificial Sequence
<220> FEATURE:
<223> OTHER INFORMATION: ST1A3-F PCR Primer

<400> SEQUENCE: 49
cctgaagatc cgtatttgtg aag 23

<210> SEQ ID NO 50
<211> LENGTH: 23
<212> TYPE: DNA
<213> ORGANISM: Artificial Sequence
<220> FEATURE:
<223> OTHER INFORMATION: ST1A3-R PCR Primer

<400> SEQUENCE: 50
cctgaagatc cgtatttgtg aag 23

<210> SEQ ID NO 51
<211> LENGTH: 19
<212> TYPE: DNA
<213> ORGANISM: Artificial Sequence
<220> FEATURE:
<223> OTHER INFORMATION: PLCH-1-F PCR Primer

<400> SEQUENCE: 51
cataaagggc agcatgagc 19

<210> SEQ ID NO 52
<211> LENGTH: 20
<212> TYPE: DNA
<213> ORGANISM: Artificial Sequence
<220> FEATURE:
<223> OTHER INFORMATION: COL3A1-F PCR Primer

<400> SEQUENCE: 52
tgccagcatg caaattctac 20

<210> SEQ ID NO 53
<211> LENGTH: 23
<212> TYPE: DNA
<213> ORGANISM: Artificial Sequence
<220> FEATURE:
<223> OTHER INFORMATION: COL3A1-F PCR Primer

<400> SEQUENCE: 53
atatacaaca ttactacctc cag 23

<210> SEQ ID NO 54
<211> LENGTH: 23
<212> TYPE: DNA
<213> ORGANISM: Artificial Sequence
<220> FEATURE:
<223> OTHER INFORMATION: COL3A1 -R PCR Primer

<400> SEQUENCE: 54
atatacaaca ttactacctc cag 23

<210> SEQ ID NO 55
<211> LENGTH: 20

<212> TYPE: DNA
<213> ORGANISM: Artificial Sequence
<220> FEATURE:
<223> OTHER INFORMATION: HoxD4-F PCR Primer

<400> SEQUENCE: 55
tggtctaccc ctggatgaag 20

<210> SEQ ID NO 56
<211> LENGTH: 20
<212> TYPE: DNA
<213> ORGANISM: Artificial Sequence
<220> FEATURE:
<223> OTHER INFORMATION: HoxD4-R PCR Primer

<400> SEQUENCE: 56
agatgaggac gatgacctgc 20

<210> SEQ ID NO 57
<211> LENGTH: 20
<212> TYPE: DNA
<213> ORGANISM: Artificial Sequence
<220> FEATURE:
<223> OTHER INFORMATION: HoxD3-F PCR Primer

<400> SEQUENCE: 57
cagcctcctg gtctgaactc 20

<210> SEQ ID NO 58
<211> LENGTH: 20
<212> TYPE: DNA
<213> ORGANISM: Artificial Sequence
<220> FEATURE:
<223> OTHER INFORMATION: HoxD3-R PCR Primer

<400> SEQUENCE: 58
atccagggga agatctgctt 20

<210> SEQ ID NO 59
<211> LENGTH: 21
<212> TYPE: DNA
<213> ORGANISM: Artificial Sequence
<220> FEATURE:
<223> OTHER INFORMATION: P21-F PCR Primer

<400> SEQUENCE: 59
tcctcatccc gtgttctcct t 21

<210> SEQ ID NO 60
<211> LENGTH: 22
<212> TYPE: DNA
<213> ORGANISM: Artificial Sequence
<220> FEATURE:
<223> OTHER INFORMATION: P21-R PCR Primer

<400> SEQUENCE: 60
aggaggaagt agctggcatg aa 22

<210> SEQ ID NO 61
<211> LENGTH: 18
<212> TYPE: DNA
<213> ORGANISM: Artificial Sequence
<220> FEATURE:
<223> OTHER INFORMATION: P16-F PCR Primer

<400> SEQUENCE: 61
gcccaacgca ccgaatag 18

<210> SEQ ID NO 62
<211> LENGTH: 18
<212> TYPE: DNA
<213> ORGANISM: Artificial Sequence
<220> FEATURE:
<223> OTHER INFORMATION: P16-R PCR Primer

<400> SEQUENCE: 62
cgctgcccat catcatga 18

<210> SEQ ID NO 63
<211> LENGTH: 24
<212> TYPE: DNA
<213> ORGANISM: Artificial Sequence
<220> FEATURE:
<223> OTHER INFORMATION: BIM-F PCR Primer

<400> SEQUENCE: 63
cagtttccct ggcttacttg tgtt 24

<210> SEQ ID NO 64
<211> LENGTH: 27
<212> TYPE: DNA
<213> ORGANISM: Artificial Sequence
<220> FEATURE:
<223> OTHER INFORMATION: BIM-R PCR Primer

<400> SEQUENCE: 64
gtattgcaca agtaaagtgg caattac 27

<210> SEQ ID NO 65
<211> LENGTH: 20
<212> TYPE: DNA
<213> ORGANISM: Artificial Sequence
<220> FEATURE:
<223> OTHER INFORMATION: PTBP2-F PCR Primer

<400> SEQUENCE: 65
cagttggcgt gaagagagga 20

<210> SEQ ID NO 66
<211> LENGTH: 20
<212> TYPE: DNA
<213> ORGANISM: Artificial Sequence
<220> FEATURE:
<223> OTHER INFORMATION: PTBP2-R PCR Primer

<400> SEQUENCE: 66
agtacacgag aaggagcacc 20

<210> SEQ ID NO 67
<211> LENGTH: 20
<212> TYPE: DNA
<213> ORGANISM: Artificial Sequence
<220> FEATURE:
<223> OTHER INFORMATION: DGCR14-F PCR Primer

<400> SEQUENCE: 67
agccgaggag aatggagact 20

<210> SEQ ID NO 68
<211> LENGTH: 20
<212> TYPE: DNA
<213> ORGANISM: Artificial Sequence -continued
<220> FEATURE:
<223> OTHER INFORMATION: DGCR14-R PCR Primer

<400> SEQUENCE: 68
ttctcctcct cctctccagc 20

<210> SEQ ID NO 69
<211> LENGTH: 20
<212> TYPE: DNA
<213> ORGANISM: Artificial Sequence
<220> FEATURE:
<223> OTHER INFORMATION: SERAC1-F PCR Primer

<400> SEQUENCE: 69
actgcggaat ccatttgctg 20

<210> SEQ ID NO 70
<211> LENGTH: 20
<212> TYPE: DNA
<213> ORGANISM: Artificial Sequence
<220> FEATURE:
<223> OTHER INFORMATION: SERAC1-R PCR Primer

<400> SEQUENCE: 70
agcaatcaag agccagctga 20

<210> SEQ ID NO 71
<211> LENGTH: 20
<212> TYPE: DNA
<213> ORGANISM: Artificial Sequence
<220> FEATURE:
<223> OTHER INFORMATION: GAPDH-F PCR Primer

<400> SEQUENCE: 71
atgttcgtca tgggtgtgaa 20

<210> SEQ ID NO 72
<211> LENGTH: 20
<212> TYPE: DNA
<213> ORGANISM: Artificial Sequence
<220> FEATURE:
<223> OTHER INFORMATION: GAPDH-R PCR Primer

<400> SEQUENCE: 72
tgtggtcatg agtccttcca 20

<210> SEQ ID NO 73
<211> LENGTH: 26
<212> TYPE: DNA
<213> ORGANISM: Artificial Sequence
<220> FEATURE:
<223> OTHER INFORMATION: Cas9 D10A-F PCR Primer

<400> SEQUENCE: 73
gcatcggcct ggccatcggc accaac 26

<210> SEQ ID NO 74
<211> LENGTH: 26
<212> TYPE: DNA
<213> ORGANISM: Artificial Sequence
<220> FEATURE:
<223> OTHER INFORMATION: Cas9 D10A-R PCR Primer

<400> SEQUENCE: 74
gttggtgccg atggccaggc cgatgc 26

-continued

<210> SEQ ID NO 75
<211> LENGTH: 60
<212> TYPE: DNA
<213> ORGANISM: Homo sapiens

<400> SEQUENCE: 75
ttgtctatat ataccctgta gaaccgaatt tgtgtggtat ccgtatagtc acagattcga 60

<210> SEQ ID NO 76
<211> LENGTH: 47
<212> TYPE: DNA
<213> ORGANISM: Artificial Sequence
<220> FEATURE:
<223> OTHER INFORMATION: edited miR-10b genome sequence

<400> SEQUENCE: 76
ttgtcttgtc cggaatttgt gtggtatccg tatagtcaca gattcga 47

<210> SEQ ID NO 77
<211> LENGTH: 44
<212> TYPE: DNA
<213> ORGANISM: Artificial Sequence
<220> FEATURE:
<223> OTHER INFORMATION: edited miR-10b genome sequence

<400> SEQUENCE: 77
tgtgtcgtcg aatttgtgtg gtatccgtat agtcacagat tcga 44

<210> SEQ ID NO 78
<211> LENGTH: 60
<212> TYPE: DNA
<213> ORGANISM: Artificial Sequence
<220> FEATURE:
<223> OTHER INFORMATION: edited miR-10b genome sequence

<400> SEQUENCE: 78
ttgtctatat ataccctgta gaaccgaatt tgtgtggtat ccgtatagtc acagattcga 60

<210> SEQ ID NO 79
<211> LENGTH: 15
<212> TYPE: DNA
<213> ORGANISM: Artificial Sequence
<220> FEATURE:
<223> OTHER INFORMATION: edited miR-10b genome sequence

<400> SEQUENCE: 79
tagtcacaga ttcga 15

<210> SEQ ID NO 80
<211> LENGTH: 47
<212> TYPE: DNA
<213> ORGANISM: Artificial Sequence
<220> FEATURE:
<223> OTHER INFORMATION: edited miR-10b genome sequence

<400> SEQUENCE: 80
ttgtgtagaa ccgaatttgt gtggtatccg tatagtcaca gattcga 47

<210> SEQ ID NO 81
<211> LENGTH: 31
<212> TYPE: DNA
<213> ORGANISM: Artificial Sequence
<220> FEATURE:
<223> OTHER INFORMATION: edited miR-10b genome sequence

<400> SEQUENCE: 81
ttgtgtggta tccgtatagt cacagattcg a 31

<210> SEQ ID NO 82
<211> LENGTH: 50
<212> TYPE: DNA
<213> ORGANISM: Artificial Sequence
<220> FEATURE:
<223> OTHER INFORMATION: edited miR-10b genome sequence

<400> SEQUENCE: 82
ttgtctagta gaaccgaatt tgtgtggtat ccgtatagtc acagattcga 50

<210> SEQ ID NO 83
<211> LENGTH: 11
<212> TYPE: DNA
<213> ORGANISM: Artificial Sequence
<220> FEATURE:
<223> OTHER INFORMATION: edited miR-10b genome sequence

<400> SEQUENCE: 83
ttgtctatat a 11

<210> SEQ ID NO 84
<211> LENGTH: 11
<212> TYPE: DNA
<213> ORGANISM: Artificial Sequence
<220> FEATURE:
<223> OTHER INFORMATION: edited miR-10b genome sequence

<400> SEQUENCE: 84
ttgtctatat a 11

<210> SEQ ID NO 85
<211> LENGTH: 47
<212> TYPE: DNA
<213> ORGANISM: Artificial Sequence
<220> FEATURE:
<223> OTHER INFORMATION: edited miR-10b genome sequence

<400> SEQUENCE: 85
ttgtctatat acgaatttgt gtggtatccg tatagtcaca gattcga 47

<210> SEQ ID NO 86
<211> LENGTH: 60
<212> TYPE: DNA
<213> ORGANISM: Artificial Sequence
<220> FEATURE:
<223> OTHER INFORMATION: edited miR-10b genome sequence

<400> SEQUENCE: 86
ttgtctatat ataccctgta gaaccgaatt tgtgtggtat ccgtatagtc acagattcga 60

<210> SEQ ID NO 87
<211> LENGTH: 50
<212> TYPE: DNA
<213> ORGANISM: Artificial Sequence
<220> FEATURE:
<223> OTHER INFORMATION: edited miR-10b genome sequence

<400> SEQUENCE: 87
ttgtctatat gaaccgaatt tgtgtggtat ccgtatagtc acagattcga 50

<210> SEQ ID NO 88
<211> LENGTH: 60
<212> TYPE: DNA

<213> ORGANISM: Artificial Sequence
<220> FEATURE:
<223> OTHER INFORMATION: edited miR-10b genome sequence

<400> SEQUENCE: 88
ttgtctatat ataccctgta gaaccgaatt tgtgtggtat ccgtatagtc acagattcga 60

<210> SEQ ID NO 89
<211> LENGTH: 47
<212> TYPE: DNA
<213> ORGANISM: Artificial Sequence
<220> FEATURE:
<223> OTHER INFORMATION: edited miR-10b genome sequence

<400> SEQUENCE: 89
ttgtctatat ataccctgta gtggtatccg tatagtcaca gattcga 47

<210> SEQ ID NO 90
<211> LENGTH: 30
<212> TYPE: DNA
<213> ORGANISM: Artificial Sequence
<220> FEATURE:
<223> OTHER INFORMATION: edited miR-10b genome sequence

<400> SEQUENCE: 90
tgtgtggtat ccgtatagtc acagattcga 30

<210> SEQ ID NO 91
<211> LENGTH: 32
<212> TYPE: DNA
<213> ORGANISM: Artificial Sequence
<220> FEATURE:
<223> OTHER INFORMATION: edited miR-10b genome sequence

<400> SEQUENCE: 91
ttgtctatgt atccgtatag tcacagattc ga 32

<210> SEQ ID NO 92
<211> LENGTH: 32
<212> TYPE: DNA
<213> ORGANISM: Artificial Sequence
<220> FEATURE:
<223> OTHER INFORMATION: edited miR-10b genome sequence

<400> SEQUENCE: 92
ttgtctatgt atccgtatag tcacagattc ga 32

<210> SEQ ID NO 93
<211> LENGTH: 45
<212> TYPE: DNA
<213> ORGANISM: Artificial Sequence
<220> FEATURE:
<223> OTHER INFORMATION: edited miR-10b genome sequence

<400> SEQUENCE: 93
ttgtctatat atacctgtgt ggtatccgta tagtcacaga ttcga 45

<210> SEQ ID NO 94
<211> LENGTH: 45
<212> TYPE: DNA
<213> ORGANISM: Artificial Sequence
<220> FEATURE:
<223> OTHER INFORMATION: edited miR-10b genome sequence

<400> SEQUENCE: 94
ttgtctatat atatttgtgt ggtatccgta tagtcacaga ttcga 45

```
<210> SEQ ID NO 95
<211> LENGTH: 58
<212> TYPE: DNA
<213> ORGANISM: Artificial Sequence
<220> FEATURE:
<223> OTHER INFORMATION: edited miR-10b genome sequence

<400> SEQUENCE: 95

ttgtctatat ataccctgta gaaccgaagg tgtggtatcc gtatagtcac agattcga        58

<210> SEQ ID NO 96
<211> LENGTH: 110
<212> TYPE: RNA
<213> ORGANISM: Homo sapiens

<400> SEQUENCE: 96

ccagagguug uaacguuguc uauauauacc cuguagaacc gaauuugugu gguauccgua      60

uagucacaga uucgauucua ggggaauaua uggucgaugc aaaaacuuca                 110

<210> SEQ ID NO 97
<211> LENGTH: 110
<212> TYPE: RNA
<213> ORGANISM: Homo sapiens

<400> SEQUENCE: 97

gaucugucug ucuucuguau auacccugua gauccgaauu uguguaagga auuuuguggu      60

cacaaauucg uaucuagggg aauauguagu ugacauaaac acuccgcucu                 110
```